United States Patent
Stocker et al.

(10) Patent No.: US 6,753,177 B1
(45) Date of Patent: Jun. 22, 2004

(54) P-GLYCOPROTEINS AND USES THEREOF

(75) Inventors: Penny J. Stocker, Jamaica Plain, MA (US); Dorothy T. Steimel-Crespi, Marblehead, MA (US); Charles L. Crespi, Marblehead, MA (US); Timothy C. Reif, Needham, MA (US); Christopher J. Patten, Scituate, MA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 26 days.

(21) Appl. No.: 09/672,725

(22) Filed: Sep. 28, 2000

Related U.S. Application Data

(60) Provisional application No. 60/156,510, filed on Sep. 28, 1999.

(51) Int. Cl.$^7$ .......................... C12P 21/06; C12N 9/00; C12N 1/20; C07H 21/04; C07K 1/00
(52) U.S. Cl. .................. 435/252.3; 435/69.1; 435/183; 435/252; 435/320.1; 536/23.2; 536/23.5; 536/23.7; 530/350
(58) Field of Search ............................... 435/69.1, 183, 435/252.3, 320.1; 536/23.2–23.7; 530/350; 436/87

(56) References Cited

U.S. PATENT DOCUMENTS

| | | |
|---|---|---|
| 5,429,921 A | 7/1995 | Harpold et al. |
| 5,830,697 A | 11/1998 | Sikic et al. |

OTHER PUBLICATIONS

Sharom et al., *Biochem. Pharmacol.* 58:571–586, 1999.
Sugden et al., *Mol. Cell Biol.* 5:410–413, 1985.
Yates et al., *Nature(Lond.)* 313: 812–815, 1985.
Sarkadi et al., *J. Biol. Chem.* 267: 4854–4858, 1992.
Druekes et al., *Anal. Biochem.* 230: 173–177, 1995.
U.S. patent application Ser. No. 09/672,810.
Steingold et al., *Anticancer Res.* 18: 393–400 (1998).
Yang et al., *J. of Biol. Chem.* 264(2): 782–788 (1989).
Chen et al., *J. of Biol. Chem.* 265(1): 506–514 (1990).
Chen et al., *J. of Biol. Chem.* 272(9): 5974–5982 (1997).
Chen et al., *Cell* 47: 381–389 (1986).
Ambudkar et al., *J. of Biol. Chem.* 272(34): 21160–21166 (1997).
Kioka et al., *Biochem. and Biophys. Res. Comm.* 162(1): 224–231 (1989).
Sharom et al., *Chem. Abstracts* 131(17): abstract No. 223128, no page given (1999).
Ma et al., *Proc. of the Amer. Assoc. for Cancer Res. Ann.* 41: 765 (2000).

*Primary Examiner*—Manjunath Rao
(74) *Attorney, Agent, or Firm*—Wolf, Greenfield and Sacks, P.C.

(57) ABSTRACT

The invention pertains to dog P-glycoproteins and related P-glycoproteins which include dog-specific amino acids, as well as nucleic acids which encode those polypeptides. The present invention also includes fragments and biologically functional variants of the dog P-glycoprotein. The invention further relates to methods of using such dog P-glycoprotein nucleic acids and polypeptides, especially in methods for determining bioavailability of drugs and for screening for inhibitors of dog PGP. Also included are dog PGP inhibitors which inhibit dog PGP activity by inhibiting the expression or function of dog PGP.

5 Claims, No Drawings

P-GLYCOPROTEINS AND USES THEREOF

RELATED APPLICATIONS

This application claims priority under 35 U.S.C. §119 from U.S. provisional patent application No. 60/156,510, filed Sep. 28, 1999.

FIELD OF THE INVENTION

The invention pertains to P-glycoproteins of dog (*Canis familiaris*).

BACKGROUND OF THE INVENTION

P-glycoprotein (PGP; also known as multidrug transporter, MDR1) is a member of the ABC transporter superfamily and is expressed in the human intestine, liver and other tissues. This enzyme serves as an efflux pump exporting small molecules across the cell membrane. It has been known for several years that high level expression of PGP is a mechanism for tumor resistance to cancer chemotherapy. Intestinal expression of PGP may affect the oral bioavailability of drug molecules that are substrates for this transporter. PGP can efficiently efflux drugs back into the intestinal lumen and thus reduce the amount of drug that enters into circulation.

The measurement of interaction with PGP can provide a better understanding of the reasons why particular drugs demonstrate low or high bioavailability. Interaction with PGP can be studied using either direct assays of drug transport in polarized cell systems or with indirect assays such as drug-stimulated ATPase activity and inhibition of the transport of fluorescent substrates.

Therefore there is a need for additional PGP polypeptides, preferably which are closely related to the human PGP, for use in the foregoing drug assays.

SUMMARY OF THE INVENTION

Nucleic acids encoding P-glycoprotein of dog (*Canis familiaris*) have now been identified, isolated, cloned and sequenced. This PGP is closely related (has a high degree of identity) to the human PGP. The invention provides isolated nucleic acid molecules, unique fragments of those molecules, expression vectors containing the foregoing, and host cells transfected with those molecules. The invention also provides isolated polypeptides and inhibitors of the foregoing nucleic acids and polypeptides which reduce drug transport. The PGP nucleic acids and polypeptides are useful in assays for evaluating bioavailability of drugs, as well as for the optimization or discovery of drugs. In addition, the foregoing can be used in the diagnosis or treatment of conditions characterized by PGP activity and can be used in methods in which it is therapeutically useful to increase or decrease PGP activity.

According to one aspect of the invention, an isolated nucleic acid molecule is provided which is selected from the group consisting of (a) nucleic acid molecules that code for the amino acid sequence of SEQ ID NO:2, (b) allelic variants of (a), wherein the allelic variants exclude SEQ ID NO:3 and SEQ ID NO:5, and (c) complements of (a) or (b). Preferred allelic variants include nucleic acid molecules that encode an amino acid sequence selected from the group consisting of SEQ ID NO:23, SEQ ID NO:25 and SEQ ID NO:27, particularly nucleotide sequences selected from the group consisting of SEQ ID NO:22, SEQ ID NO:24 and SEQ ID NO:26. In preferred embodiments the isolated nucleic acid molecule codes for SEQ ID NO:2, or comprises the nucleotide sequence of SEQ ID NO:1. In particularly preferred embodiments, the nucleic acid molecules comprise or consist of the coding region of the aforementioned nucleotide sequences.

According to other aspects of the invention, isolated P-glycoprotein polypeptides or fragments thereof are provided. The polypeptides include at least one amino acid of a dog P-glycoprotein selected from the group consisting of amino acids 25, 192, 197, 212, 288, 329, 532, 696,1273 and 1355 of SEQ ID NO:2; amino acid 25 of SEQ ID NO:23; and amino acids 25 and 1148 of SEQ ID NO:25. Other isolated P-glycoprotein polypeptides or fragments thereof include at least one amino acid of a dog P-glycoprotein selected from the group consisting of amino acids 3, 6, 8, 10, 12, 14–26, 36, 38, 48, 52, 56, 64, 74, 78, 84–92, 94, 96, 98, 99, 101, 103, 104, 106, 108, 112, 115, 147, 187, 197, 199, 233, 288, 321, 326, 347, 397, 450, 454, 455, 467, 472, 520, 633, 637, 643, 644, 650, 657, 658, 661, 666, 667, 674–677, 679, 685, 689, 691, 693, 694, 703, 707, 717, 731, 736, 740, 744, 745, 756, 759, 763, 853, 914, 920, 942, 943, 946, 968–970, 972, 974, 983, 1005, 1010, 1017, 1025, 1026, 1029, 1040, 1095, 1098, 1105, 1144, 1148, 1149, 1158, 1162, 1165, 1168, 1170, 1252 and 1279 of SEQ ID NO:2; and amino acid 329 of SEQ ID NO:27, wherein the P-glycoprotein is identical to a human P-glycoprotein except for the at least one amino acid of a dog P-glycoprotein. In certain embodiments, the human P-glycoprotein is selected from the group of SEQ ID NO:7 and SEQ ID NO:8. Still other isolated P-glycoprotein polypeptides or fragments thereof include at least one amino acid of a dog P-glycoprotein that is different from a cynomologous P-glycoprotein, wherein the P-glycoprotein is identical to a cynomologous monkey P-glycoprotein except for the at least one amino acid of a dog P-glycoprotein. Yet other polypeptides include combinations of the foregoing dog, human and cynomologous PGP polypeptides. In preferred embodiments, the isolated P-glycoprotein polypeptides or fragments thereof include an amino acid sequence selected from the group consisting of SEQ ID NO:2, SEQ ID NO:23, SEQ ID NO:25, SEQ ID NO:27, fragments of SEQ ID NO:2, fragments of SEQ ID NO:23, fragments of SEQ ID NO:25 and fragments of SEQ ID NO:27.

According to still other embodiments of the invention, isolated nucleic acid molecules are provide which encode the foregoing isolated P-glycoprotein polypeptides or fragments thereof Also included expression vectors comprising the foregoing isolated nucleic acid molecules operably linked to a promoter, as well as host cells transformed or transfected with the expression vectors.

In another aspect of the invention, agents which selectively binds the isolated PGP polypeptides are provided. Preferably the agent does not bind a human or dog P-glycoprotein, except those provided herein. In certain embodiments, the agent is a polypeptide preferably one selected from the group consisting of monoclonal antibodies, polyclonal antibodies, Fab antibody fragments, F(ab)$_2$ antibody fragments and antibody fragments including a CDR3 region. Also provided are agents which selectively binds the foregoing isolated nucleic acid molecules, preferably antisense nucleic acid molecules which selectively binds to the isolated nucleic acid molecule.

According to another aspect of the invention, methods for predicting the bioavailability of a compound are provided. The methods include measuring the transmembrane transport of a test compound by a first P-glycoprotein, comparing the transmembrane transport of the test compound by the first P-glycoprotein and a second P-glycoprotein to predict the bioavailability of the test compound, wherein the relative amount or rate of transport by the first P-glycoprotein and the second P-glycoprotein is predictive of bioavailability of the test compound. In certain embodiments the first P-glycoprotein is selected from the group consisting of dog P-glycoproteins and primate P-glycoproteins, preferably one of the foregoing polypeptides. In other embodiments the second P-glycoprotein is a human P-glycoprotein.

In still other aspects of the invention, methods for inhibiting P-glycoprotein transporter activity in a mammalian cell are provided. The methods include contacting the mammalian cell with an amount of one of the foregoing agents effective to inhibit P-glycoprotein transporter activity in the mammalian cell.

Also included in the invention are methods for increasing bioavailability of a drug in a subject. The methods include administering to a subject in need of such treatment one of the foregoing agents in an amount effective to increasing bioavailability of a drug. The inhibitor can be administered prior to administering the drug, or concurrently with the drug.

Also provided are methods for increasing P-glycoprotein transporter activity in a cell. These methods include contacting the cell with a molecule selected from the group consisting of the foregoing nucleic acid molecules, in an amount effective to increase P-glycoprotein transporter activity in the cell. The cell can be contacted under conditions whereby the P-glycoprotein is expressed.

According to yet another aspect of the invention, methods for identifying lead compounds for a pharmacological agent useful in the treatment of disease associated with P-glycoprotein transporter activity are provided. The methods include providing a cell or other membrane-encapsulated space comprising a P-glycoprotein as provided herein; contacting the cell or other membrane-encapsulated space with a candidate pharmacological agent under conditions which, in the absence of the candidate pharmacological agent, cause a first amount of P-glycoprotein transporter activity; and determining a second amount of P-glycoprotein transporter activity as a measure of the effect of the pharmacological agent on the P-glycoprotein transporter activity, wherein a second amount of P-glycoprotein transporter activity which is less than the first amount indicates that the candidate pharmacological agent is a lead compound for a pharmacological agent which reduces P-glycoprotein transporter activity and wherein a second amount of P-glycoprotein transporter activity which is greater than the first amount indicates that the candidate pharmacological agent is a lead compound for a pharmacological agent which increases P-glycoprotein transporter activity. The methods can further include a step of loading the cell or other membrane-encapsulated space with a detectable compound, wherein the compound is detected as a measure of the P-glycoprotein transporter activity.

Also included are methods for identifying compounds which selectively bind a P-glycoprotein. The methods include contacting a P-glycoprotein provided herein with a compound, and determining the binding of the compound to the P-glycoprotein. The methods can further include determining the effect of the compound on the P-glycoprotein transporter activity of the P-glycoprotein or determining the effect of the compound on the ATPase activity of the P-glycoprotein.

Additional methods provided according to the invention include methods for determining ATPase activity of a P-glycoprotein. The methods include contacting a host cell as provided above, or a membrane fraction thereof, with a test drug, and measuring ATPase activity of the P-glycoprotein. In certain embodiments, the step of measuring ATPase activity is performed at least twice at different times. Also provided methods for determining transmembrane transport of a compound by a P-glycoprotein. The methods include contacting a host cell provided above, or a membrane fraction thereof, with a test drug, and measuring transport of the test drug under sink conditions in at least one direction of transport selected from the group consisting of the apical to basolateral direction and the basolateral to apical direction. In certain embodiments the step of measuring transport of the test drug is performed at least twice at different times.

These and other aspects of the invention are described in greater detail below.

BRIEF DESCRIPTION OF THE SEQUENCES

SEQ ID NO:1 is the nucleotide sequence encoding dog P-glycoprotein (Genotype C).

SEQ ID NO:2 is the amino acid sequence of a dog P-glycoprotein encoded by SEQ ID NO:1.

SEQ ID NO:3 is the nucleotide sequence encoding a prior art dog P-glycoprotein (GenBank accession number AF045016).

SEQ ID NO:4 is the amino acid sequence of a dog P-glycoprotein encoded by SEQ ID NO:3.

SEQ ID NO:5 is the nucleotide sequence encoding another prior art dog P-glycoprotein (GenBank accession number AF092810).

SEQ ID NO:6 is the amino acid sequence of a dog P-glycoprotein encoded by SEQ ID NO:5.

SEQ ID NO:7 is the amino acid sequence of a prior art human P-glycoprotein, having Genbank accession number M14758.

SEQ ID NO:8 is the amino acid sequence of a second prior art human P-glycoprotein, having Genbank accession numbers AF016535 or NM_000927.

SEQ ID NO:9 is the nucleotide sequence of a PCR primer homologous to human PGP1.

SEQ ID NO:10 is the nucleotide sequence of a PCR primer homologous to dog PGP2.

SEQ ID NO:11 is the nucleotide sequence of a PCR primer homologous to dog PGP1.

SEQ ID NO:12 is the nucleotide sequence of a PCR primer homologous to human PGP1.

SEQ ID NO:13 is the nucleotide sequence of a PCR primer homologous to dog PGP1.

SEQ ID NO:14 is the nucleotide sequence of a PCR primer homologous to human PGP1.

SEQ ID NO:15 is the nucleotide sequence of a PCR primer homologous to dog PGP1.

SEQ ID NO:16 is the nucleotide sequence of a PCR primer homologous to human PGP1.

SEQ ID NO:17 is the nucleotide sequence of a PCR primer homologous to dog PGP1.

SEQ ID NO:18 is the nucleotide sequence of a PCR primer homologous to vector.

SEQ ID NO:19 is the nucleotide sequence of a PCR primer homologous to dog PGP1.

SEQ ID NO:20 is the nucleotide sequence of a PCR primer homologous to human PGP1.

SEQ ID NO:21 is the nucleotide sequence of a PCR primer homologous to dog PGP1.

SEQ ID NO:22 is the nucleotide sequence encoding dog P-glycoprotein (Genotype A).

SEQ ID NO:23 is the amino acid sequence of a dog P-glycoprotein encoded by SEQ ID NO:22.

SEQ ID NO:24 is the nucleotide sequence encoding dog P-glycoprotein (Genotype B).

SEQ ID NO:25 is the amino acid sequence of a dog P-glycoprotein encoded by SEQ ID NO:24.

SEQ ID NO:26 is the nucleotide sequence encoding dog P-glycoprotein (Genotype D).

SEQ ID NO:27 is the amino acid sequence of a dog P-glycoprotein encoded by SEQ ID NO:25.

SEQ ID NO:28 is the nucleotide sequence of the cDNA synthesis primer from the Marathon cDNA Amplification Kit.

SEQ ID NO:29 is the nucleotide sequence of the cDNA Adapter Primer 1 from the Marathon cDNA Amplification Kit.

SEQ ID NO:30 is the nucleotide sequence of a PCR primer homologous to dog PGP1.

SEQ ID NO:31 is the nucleotide sequence of a PCR primer homologous to dog PGP1.

SEQ ID NO:32 is the nucleotide sequence of a PCR primer homologous to dog PGP1.

DETAILED DESCRIPTION OF THE INVENTION

The present invention in one aspect involves the identification of novel cDNAs encoding dog P-glycoproteins, referred to herein as dog PGP. The nucleotide sequence of a dog PGP (termed "Genotype C") is presented as SEQ ID NO:1, and the amino acid sequence of this dog PGP is presented as SEQ ID NO:2.

Three allelic variants of Genotype C dog PGP were isolated ("Genotype A", "Genotype B" and "Genotype D"). The nucleotide and amino acid sequences of Genotype A are presented as SEQ ID NOs:20 and 21, respectively. The amino acid sequence of Genotype A differs from the amino acid sequence of Genotype C at amino acid 197 (histidine→glutamine) based on a C→A change at nucleotide 607 of SEQ ID NO:2. The nucleotide and amino acid sequences of Genotype B are presented as SEQ ID NOs:22 and 23, respectively. The amino acid sequence of Genotype B differs from the amino acid sequence of Genotype C at amino acid 25 (asparagine→lysine) based on a T→A change at nucleotide 91 of SEQ ID NO:2, and at amino acid 197 (histidine→glutamine) based on a C→A change at nucleotide 607 of SEQ ID NO:2. The nucleotide and amino acid sequences of Genotype D are presented as SEQ ID NOs:24 and 25, respectively. The amino acid sequence of Genotype D differs from the amino acid sequence of Genotype C at amino acid 25 (asparagine→lysine) based on a T→A change at nucleotide 91 of SEQ ID NO:2, at amino acid 197 (histidine→glutamine) based on a C→A change at nucleotide 607 of SEQ ID NO:2, at amino acid 329 (serine→threonine) based on a T→A change at nucleotide 1001 of SEQ ID NO:2, and at amino acid 1148 (methionine→valine) based on a A→G change at nucleotide 3458 of SEQ ID NO:2.

Two closely related dog PGP sequence were deposited in GenBank under accession numbers AF045016 (complete cDNA) and AF092810 (partial cDNA). Whereas much of the polypeptides presented herein is identical to the known dog PGPs, the dog PGPs of the invention (SEQ ID NOs:2, 21, 23 and 25) have several single amino acid differences from the prior art sequences, including at least one deletion. These allelic differences in the very highly conserved protein domains of the P-glycoprotein are entirely unexpected.

The invention involves in one aspect dog PGP nucleic acids and polypeptides, as well as therapeutics relating thereto. The invention also embraces isolated functionally equivalent variants, useful analogs and fragments of the foregoing nucleic acids and polypeptides; complements of the foregoing nucleic acids; and molecules which selectively bind the foregoing nucleic acids and polypeptides.

The dog PGP nucleic acids and polypeptides of the invention are isolated. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

As used herein a dog PGP nucleic acid refers to an isolated nucleic acid molecule which codes for a dog PGP polypeptide. Such nucleic acid molecules code for dog PGP polypeptides which include the amino acid sequences of SEQ ID NO:2, 23, 25, 27 and fragments thereof The nucleic acid molecules include the nucleotide sequences of SEQ ID NO:1, and nucleotide sequences which differ from the sequences of SEQ ID NO:1, in codon sequence due to the degeneracy of the genetic code. The dog PGP nucleic acids of the invention also include alleles (e.g., SEQ ID Nos:22, 24, 26) of the foregoing nucleic acids (except those of previously known dog PGP alleles, e.g., SEQ ID NOS:3 and 5), and encoded polypeptides, as well as fragments of the foregoing nucleic acids and polypeptides. Such fragments can be used, for example, as probes in hybridization assays and as primers in a polymerase chain reaction (PCR). Preferred dog PGP nucleic acids include the nucleic acid sequences of SEQ ID NOs:1, 22, 24, 26 and fragments thereof. Complements of the foregoing nucleic acids also are embraced by the invention.

As used herein "dog PGP activity" refers to an ability of a PGP polypeptide to export small molecules across the cell membrane. A molecule which inhibits dog PGP activity (an antagonist) is one which inhibits export of small molecules via PGP and a molecule which increases dog PGP activity (an agonist) is one which increases export of small molecules via PGP. Changes in dog PGP activity can be measured by assays such as those disclosed herein, including efflux of fluorescent compounds from cells.

Alleles of the dog PGP nucleic acids of the invention can be identified by conventional techniques. For example, alleles of dog PGP can be isolated by hybridizing a probe which includes at least a fragment of SEQ ID NO:1 under stringent conditions with a cDNA library and selecting positive clones. Thus, an aspect of the invention is those nucleic acid sequences which code for dog PGP polypeptides and which hybridize to a nucleic acid molecule consisting of SEQ ID NO:1 under stringent conditions (except those of previously known dog PGP alleles, e.g., SEQ ID NOS:3 and 5). The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1–0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of alleles of dog PGP nucleic acids of the invention. The skilled artisan also is familiar with the methodology for screening cells and libraries for expression of such molecules which then are routinely isolated, followed by isolation of the pertinent nucleic acid molecule and sequencing.

In screening for dog PGP nucleic acids, a Southern blot may be performed using the foregoing stringent conditions, together with a radioactive probe. After washing the membrane to which the DNA is finally transferred, the membrane can be placed against X-ray film to detect the radioactive signal.

The dog PGP nucleic acids of the invention also include degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating dog PGP polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as transporter activity, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated fragments of SEQ ID NO:1. The fragments can be used as probes in Southern blot assays to identify such nucleic acids, or can be used in amplification assays such as those employing PCR. Smaller fragments are those comprising 12, 13, 14, 15, 16, 17, 18, 20, 22, 25, 30, 40, 50, or 75 nucleotides, and every integer therebetween, and are useful e.g. as primers for nucleic acid amplification procedures. As known to those skilled in the art, larger probes such as 200, 250, 300, 400 or more nucleotides are preferred for certain uses such as Southern blots, while smaller fragments will be preferred for uses such as PCR. Fragments also can be used to produce fusion proteins for generating antibodies or determining binding of the polypeptide fragments. Likewise, fragments can be employed to produce non-fused fragments of the dog PGP polypeptides, useful, for example, in the preparation of antibodies, in immunoassays, and the like. The foregoing nucleic acid fragments further can be used as antisense molecules to inhibit the expression of dog PGP nucleic acids and polypeptides, particularly for therapeutic purposes as described in greater detail below.

The invention also includes functionally equivalent variants of the dog PGP, which include variant nucleic acids and polypeptides which retain one or more of the functional properties of the dog PGP. For example, variants include a fusion protein which includes the extracellular and transmembrane domains of the dog PGP which retains the ability to transport molecules. Still other functionally equivalent variants include truncations, deletions, point mutations, or additions of amino acids to the sequence of SEQ ID NO:1 which retains functions of SEQ ID NOs:2, e.g., the alleles presented herein. Functionally equivalent variants also include a dog PGP which has had a portion of the N-terminus removed or replaced by a similar domain from another P-glycoprotein (e.g. a "domain-swapping" variant). Other functionally equivalent variants will be known to one of ordinary skill in the art, as will methods for preparing such variants. The activity of a functionally equivalent variant can be determined using the methods provided herein, and in references that have described assays using P-glycoproteins of other species. Such variants are useful, inter alia, for evaluating bioavailability of drugs, in assays for identification of compounds which bind and/or regulate the transporter function of the dog PGP, and for determining the portions of the dog PGP which are required for transporter activity.

Variants which are non-functional also can be prepared as described above. Such variants are useful, for example, as negative controls in experiments testing transporter activity.

A dog PGP nucleic acid, in one embodiment, is operably linked to a gene expression sequence which directs the expression of the dog PGP nucleic acid within a eukaryotic or prokaryotic cell. The "gene expression sequence" is any regulatory nucleotide sequence, such as a promoter sequence or promoter-enhancer combination, which facilitates the efficient transcription and translation of the dog PGP nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney murine leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined dog PGP nucleic acid. The gene expression sequences optionally includes enhancer sequences or upstream activator sequences as desired.

The dog PGP nucleic acid sequence and the gene expression sequence are said to be "operably linked" when they are covalently linked in such a way as to place the transcription and/or translation of the dog PGP coding sequence under the influence or control of the gene expression sequence. If it is desired that the dog PGP sequence be translated into a functional protein, two DNA sequences are said to be operably linked if induction of a promoter in the 5' gene expression sequence results in the transcription of the dog PGP sequence and if the nature of the linkage between the two DNA sequences does not (1) result in the introduction of a frame-shift mutation, (2) interfere with the ability of the promoter region to direct the transcription of the dog PGP sequence, or (3) interfere with the ability of the corresponding RNA transcript to be translated into a protein. Thus, a gene expression sequence would be operably linked to a dog PGP nucleic acid sequence if the gene expression sequence were capable of effecting transcription of that dog PGP nucleic acid sequence such that the resulting transcript might be translated into the desired protein or polypeptide.

The dog PGP nucleic acid molecules and the dog PGP polypeptides (including the dog PGP inhibitors described below) of the invention can be delivered to the eukaryotic or prokaryotic cell alone or in association with a vector. In its broadest sense, a "vector" is any vehicle capable of facilitating: (1) delivery of a dog PGP nucleic acid or polypeptide to a target cell, (2) uptake of a dog PGP nucleic acid or polypeptide by a target cell, or (3) expression of a dog PGP nucleic acid molecule or polypeptide in a target cell. Preferably, the vectors transport the dog PGP nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor (e.g. a receptor, an antigen recognized by an antibody) for the targeting ligand. In this manner, the vector (containing a dog PGP nucleic acid or a dog PGP polypeptide) can be selectively delivered to a specific cell. In general, the vectors useful in the invention are divided into two classes: biological vectors and chemical/physical vectors. Biological vectors are more useful for delivery/uptake of dog PGP nucleic acids to/by a target cell. Chemical/physical vectors are more useful for delivery/uptake of dog PGP nucleic acids or dog PGP proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be linnked to the nucleic acid sequences of the invention. Viral vectors are a preferred type of biological vector and include, but are not limited to, nucleic acid sequences from the following viruses: retroviruses, such as Moloney murine leukemia virus; Harvey murine sarcoma virus; murine mammary tumor virus; Rous sarcoma virus; adenovirus; adeno-associated virus; SV40-type viruses; polyoma viruses; poxviruses; retroviruses; Epstein-Barr viruses; papilloma viruses; herpes virus; vaccinia virus; and polio virus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual*," W. H. Freeman C. O., New York (1990) and Murry, E. J. Ed. "*Methods in Molecular Biology*," vol. 7, Humana Press, Inc., Clifton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Expression vectors containing all the necessary elements for expression are commercially available and known to those skilled in the art See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a dog PGP polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992).

In addition to the biological vectors, chemical/physical vectors may be used to deliver a dog PGP nucleic acid or polypeptide to a target cell and facilitate uptake thereby. As used herein, a "chemical/physical vector" refers to a natural or synthetic molecule, other than those derived from bacteriological or viral sources, capable of delivering the isolated dog PGP nucleic acid or polypeptide to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vesicles which are useful as a delivery vector in vivo or in vitro. It has been shown that large unilamellar vesicles (LUV), which range in size from 0.2–4.0μ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the dog PGP nucleic acid to the nucleus of the host cell.

Liposomes are commercially available from Gibco BRL, for example, as LIPOFECTINT™ and LIPOFECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications.

Other exemplary compositions that can be used to facilitate uptake by a target cell of the dog PGP nucleic acids include calcium phosphate and other chemical mediators of intracellular transport, microinjection compositions, electroporation and homologous recombination compositions (e.g., for integrating a dog PGP nucleic acid into a preselected location within a target cell chromosome).

The invention also embraces so-called expression kits, which allow the artisan to prepare a desired expression vector or vectors. Such expression kits include at least separate portions of the previously discussed coding sequences. Other components may be added, as desired, as long as the previously mentioned sequences, which are required, are included.

It will also be recognized that the invention embraces the use of the dog PGP cDNA sequences in expression vectors, as well as to transfect host cells and cell lines, be these prokaryotic (e.g., *E. coli*), or eukaryotic (e.g., COS cells, yeast expression systems and recombinant baculovirus expression in insect cells). Especially useful are mammalian cells such as human, pig, goat, primate, etc. They may be of a wide variety of tissue types, and include primary cells and cell lines. Specific examples include intestinal cells and liver cells. The expression vectors require that the pertinent sequence, i.e., those nucleic acids described supra, be operably linked to a promoter.

The invention also provides isolated dog PGP polypeptides which include the amino acid sequence of SEQ ID NO:2, and fragments thereof, encoded by the dog PGP nucleic acids described above. Dog PGP polypeptides also embrace alleles, such as SEQ ID NOs:23, 25 and 27 (except not SEQ ID NOS:3 and 5), functionally equivalent variants and analogs (those non-allelic polypeptides which vary in amino acid sequence from the disclosed dog PGP polypeptides by 1, 2, 3, 4, 5, or more amino acids) provided that such polypeptides retain dog PGP activity. Non-functional variants also are embraced by the invention; these are useful as antagonists of transporter function, as negative controls in assays, and the like. Such alleles, variants, analogs and fragments are useful, for example, alone or as fusion proteins for a variety of purposes including as a component of assays.

Fragments of a polypeptide preferably are those fragments which retain a distinct functional capability of the dog PGP polypeptide, in particular as a transporter of various molecules. Other functional capabilities which can be retained in a fragment of a dog PGP polypeptide include interaction with antibodies and interaction with other polypeptides (such as would be found in a protein complex). Those skilled in the art are well versed in methods for selecting fragments which retain a functional capability of the dog PGP. Confirmation of the functional capability of the fragment can be carried out by synthesis of the fragment and testing of the capability according to standard methods. For example, to test the transporter activity of a dog PGP fragment, one inserts or expresses the fragment in a cell in which molecular transport can be measured. Such methods, which are standard in the art, are described further herein.

The invention embraces variants of the dog PGP polypeptides described above. As used herein, a "variant" of a dog PGP polypeptide is a polypeptide which contains one or more modifications to the primary amino acid sequence of a dog PGP polypeptide. Modifications which create a dog PGP variant can be made to a dog PGP polypeptide for a variety of reasons, including 1) to reduce or eliminate an activity of a dog PGP polypeptide, such as transport; 2) to enhance a property of a dog PGP polypeptide, such as protein stability in an expression system or the stability of protein-protein binding; 3) to provide a novel activity or property to a dog PGP polypeptide, such as addition of an antigenic epitope or addition of a detectable moiety; or 4) to establish that an amino acid substitution does or does not affect molecular transport activity. Modifications to a dog PGP polypeptide are typically made to the nucleic acid which encodes the dog PGP polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the dog PGP amino acid sequence. One of skill in the art will be familiar with methods for predicting the effect on protein conformation of a change in protein sequence, and can thus "design" a variant dog PGP according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a dog PGP polypeptide can be proposed and tested to determine whether the variant retains a desired conformation.

Variants include dog PGP polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a dog PGP polypeptide by eliminating proteolysis by proteases in an expression system (e.g., dibasic amino acid residues in yeast expression systems in which KEX2 protease activity is present).

Mutations of a nucleic acid which encode a dog PGP polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with a desired property. Further mutations can be made to variants (or to non-variant dog PGP polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a dog PGP gene or cDNA clone to enhance expression of the polypeptide.

The activity of variants of dog PGP polypeptides can be tested by cloning the gene encoding the variant dog PGP polypeptide into a bacterial or mammalian expression vector, introducing the vector into an appropriate host cell, expressing the variant dog PGP polypeptide, and testing for a functional capability of the dog PGP polypeptides as disclosed herein. For example, the variant dog PGP polypeptide can be tested for ability to provide molecular transport (e.g., efflux), as set forth below in the examples. Preparation of other variant polypeptides may favor testing of other activities, as will be known to one of ordinary skill in the art.

The skilled artisan will also realize that conservative amino acid substitutions may be made in dog PGP polypeptides to provide functionally equivalent variants of the foregoing polypeptides, i.e, variants which retain the functional capabilities of the dog PGP polypeptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecu-*

*lar Biology*, F. M. Ausubel, et al., eds., John Wiley & Sons, Inc., New York. Exemplary functionally equivalent variants of the dog PGP polypeptides include conservative amino acid substitutions of SEQ ID NO:2 or SEQ ID NO:4. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of dog PGP polypeptide to produce functionally equivalent variants of dog PGP typically are made by alteration of the nucleic acid sequence encoding dog PGP polypeptides (e.g., SEQ ID NO:1). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad Sci. U.S.A.* 82: 488–492, 1985), or by chemical synthesis of a gene encoding a dog PGP polypeptide. The activity of functionally equivalent fragments of dog PGP polypeptides can be tested by cloning the gene encoding the altered dog PGP polypeptide into a bacterial or mammalian expression vector, introducing the vector into an appropriate host cell, expressing the altered dog PGP polypeptide, and testing for the ability of the dog PGP polypeptide to mediate transmembrane transport of compounds. Peptides which are chemically synthesized can be tested directly for function.

A variety of methodologies well-known to the skilled practitioner can be utilized to obtain isolated dog PGP molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating dog PGP polypeptides. These include, but are not limited to, immunochromatography, HPLC, size-exclusion chromatography, ion-exchange chromatography and immune-affinity chromatography.

The invention as described herein has a number of uses, some of which are described elsewhere herein. For example, the invention permits isolation of the dog PGP polypeptide molecules by e.g., expression of a recombinant nucleic acid to produce large quantities of polypeptide which may be isolated using standard protocols. As another example, the isolation of the dog PGP gene makes it possible for dog PGP to be used in methods for assaying of molecular transport, such as drug bioavailability studies. These methods involve determining transport of a drug by a first species' PGP (e.g., dog) in comparison to transport of the drug by other species' PGP (e.g. human) as a method for determining or predicting the bioavailability of the drug. Thus the results of whole animal studies on the metabolism of a drug can be evaluated in view of the relative rates or amounts of P-glycoprotein transport of the drug. For example, if a drug administered to a dog has good oral bioavailability and low transport by dog PGP, one can predict that the oral bioavailability of the drug in humans will be good if the transport by human PGP is also low. Conversely, if the transport of the drug by human PGP is high, then the bioavailability of the drug would be predicted to be low.

The invention also embraces agents which bind selectively to the dog PGP nucleic acid molecules or polypeptides as well as agents which bind to variants and fragments of the polypeptides and nucleic acids as described herein. The agents include polypeptides which bind to dog PGP, and antisense nucleic acids, both of which are described in greater detail below. The agents can inhibit or increase dog PGP activity (antagonists and agonists, respectively).

Some of the agents are inhibitors. A dog PGP inhibitor is an agent that inhibits dog PGP mediated transport of molecules across a cell membrane. Efflux assays can be performed to screen and/or determine whether a dog PGP inhibitor has the ability to inhibit dog PGP activity, and whether the inhibition is selective. An exemplary assay of efflux is described below in the Examples.

In one embodiment the dog PGP inhibitor is an antisense oligonucleotide that selectively binds to a dog PGP nucleic acid molecule, to reduce the expression of dog PGP (or other species' PGPs) in a cell. This is desirable in virtually any medical condition wherein a reduction of PGP transporter activity is desirable, e.g., to increase retention of cytotoxic agents in a cell.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, or upon allelic (except SEQ ID NOS:3 and 5)or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which polypeptides are not expected to bind. Thus, the present invention also provides for antisense oligonucleotides which are complementary to allelic (except SEQ ID NOS:3 and 5) or homologous cDNAs and genomic DNAs corresponding to a dog PGP nucleic acid containing SEQ ID NO:1.

In one set of embodiments, the antisense oligonucleotides of the invention may be composed of "natural" deoxyribonucleotides, ribonucleotides, or any combination thereof That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding dog PGP polypeptides, together with pharmaceutically acceptable carriers.

Agents which bind dog PGP also include binding peptides and other molecules which bind to the dog PGP polypeptide and complexes containing the dog PGP polypeptide. When the binding molecules are inhibitors, the molecules bind to and inhibit the activity of dog PGP. To determine whether a dog PGP binding agent binds to dog PGP any known binding assay may be employed. For example, the binding agent may be immobilized on a surface and then contacted with a labeled dog PGP polypeptide. The amount of dog PGP which interacts with the dog PGP binding agent or the amount which does not bind to the dog PGP binding agent may then be quantitated to determine whether the dog PGP binding agent binds to dog PGP.

The dog PGP binding agents include molecules of numerous size and type that bind selectively or preferentially to dog PGP polypeptides, and complexes of both dog PGP polypeptides and their binding partners. These molecules may be derived from a variety of sources. For example, dog PGP binding agents can be provided by screening degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the dog PGP polypeptide. This process can be repeated through several cycles of reselection of phage that bind to the dog PGP polypeptide. Repeated rounds lead to enrichment of phage bearing particular sequences. DNA sequence analysis can be conducted to identify the sequences of the expressed polypeptides. The minimal linear portion of the sequence that binds to the dog PGP polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the dog PGP polypeptides. Thus, the dog PGP polypeptides of the invention, or a fragment thereof, can be used to screen peptide libraries, including phage display libraries, to identify and select peptide binding partners of the dog PGP polypeptides of the invention. Such molecules can be used, as described, for screening assays, for purification protocols, for interfering directly with the functioning of dog PGP and for other purposes that will be apparent to those of ordinary skill in the art.

Therefore the invention generally provides efficient methods of identifying pharmacological agents or lead compounds for agents useful in the treatment of conditions associated with aberrant PGP activity and the compounds and agents so identified. Generally, the screening methods involve assaying for compounds which inhibit or enhance transport of molecules through dog PGP. Such methods are adaptable to automated, high throughput screening of compounds. Examples of such methods are described in U.S. Pat. No. 5,429,921.

A variety of assays for pharmacological agents are provided, including, labeled in vitro protein binding assays, efflux assays using detectable molecules, etc. For example, protein binding screens are used to rapidly examine the binding of candidate pharmacological agents to a dog PGP. The candidate pharmacological agents can be derived from, for example, combinatorial peptide libraries. Convenient reagents for such assays are known in the art. An exemplary cell-based assay of efflux involves contacting a cell having a dog PGP with a candidate pharmacological agent under conditions whereby the efflux of a detectably labeled molecule can occur. Specific conditions are well known in the art and are described, for example, in Sharom et al., *Biochem. Pharmacol.* 58:571–586, 1999, and references cited therein. A reduction in the efflux in the presence of the candidate pharmacological agent indicates that the candidate pharmacological agent reduces the efflux activity of dog PGP. An increase in the efflux in the presence of the candidate pharmacological agent indicates that the candidate pharmacological agent increases the efflux activity of dog PGP.

Dog PGP used in the methods of the invention can be added to an assay mixture as an isolated polypeptide (where binding of a candidate pharmaceutical agent is to be measured) or as a cell or other membrane-encapsulated space which includes a dog PGP polypeptide. In the latter assay configuration, the cell or other membrane-encapsulated space can contain the dog PGP as a preloaded polypeptide or as a nucleic acid (e.g. a cell transfected with an expression vector containing a dog PGP). In the assays described herein, the dog PGP polypeptide can be produced recombinantly, or isolated from biological extracts, but preferably is synthesized in vitro. Dog PGP polypeptides encompass chimeric proteins comprising a fusion of a dog PGP polypeptide with another polypeptide, e.g., a polypeptide capable of providing or enhancing protein-protein binding, or enhancing stability of the dog PGP polypeptide under assay conditions. A polypeptide fused to a dog PGP polypeptide or fragment thereof may also provide means of readily detecting the fusion protein, e.g., by immunological recognition or by fluorescent labeling.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500. Candidate agents comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

Therefore, a source of candidate agents are libraries of molecules based on known P-glycoprotein inhibitors, in which the structure of the inhibitor is changed at one or more positions of the molecule to contain more or fewer chemical moieties or different chemical moieties. The structural changes made to the molecules in creating the libraries of analog inhibitors can be directed, random, or a combination of both directed and random substitutions and/or additions. One of ordinary skill in the art in the preparation of combinatorial libraries can readily prepare such libraries based on existing P-glycoprotein inhibitors.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, anti-microbial agents, and the like may also be used.

The mixture of the foregoing assay materials is incubated under conditions whereby, but for the presence of the candidate pharmacological agent, the dog PGP mediates the efflux of a control amount of a compound such as a drug. For determining the binding of a candidate pharmaceutical agent to a dog PGP, the mixture is incubated under conditions which permit binding. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of efflux or the level of specific binding between the dog PGP polypeptide and the candidate pharmaceutical agent is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as a transmembrane transport assay. The transport of a directly or indirectly detectable product, e.g., a fluorescent molecule such as calcein AM or rhodamine 123, is preferred. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a dog PGP polypeptide or the candidate pharmacological agent.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The dog PGP binding agent may also be an antibody or a functionally active antibody fragment. Antibodies are well known to those of ordinary skill in the science of immunology. As used herein, the term "antibody" means not only intact antibody molecules but also fragments of antibody molecules retaining dog PGP binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J Nucl. Med.* 24:316–325 (1983)).

Monoclonal antibodies may be made by any of the methods known in the art utilizing dog PGP, or a fragment thereof, as an immunogen. Alternatively the antibody may be a polyclonal antibody specific for dog PGP which inhibits dog PGP activity. The preparation and use of polyclonal antibodies is also known to one of ordinary skill in the art.

Significantly, as is well known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3) The CDRs, and in particular the CDR3 regions, and more particularly the heavy chain CDR3, are largely responsible for antibody specificity.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$," fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to antigen epitopes.

The sequences of the antigen-binding Fab' portion of the anti-dog PGP monoclonal antibodies identified as being useful according to the invention in the assays provided above, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit dog PGP activity are identified. These non-human animal antibodies can be humanized for use in the treatment of a human subject in the methods according to the invention. Examples of methods for humanizing a murine antibody are provided in U.S. Pat. Nos. 4,816,567, 5,225,539, 5,585,089, 5,693,762 and 5,859,205. Other antibodies, including fragments of intact antibodies with antigen-binding ability, are often referred to as "chimeric" antibodies.

Thus, as will be apparent to one of ordinary skill in the art, the present invention also provides for F(ab')$_2$, and Fab fragments of an anti-dog PGP monoclonal antibody; chimeric antibodies in which the Fc and/or FR and/or CDR1 and/or CDR2 and/or light chain CDR3 regions of an anti-dog PGP antibody have been replaced by homologous human or non-human sequences; chimeric F(ab')$_2$ fragment antibodies in which the FR and/or CDR1 and/or CDR2 and/or light chain CDR3 regions of an anti-dog PGP antibody have been replaced by homologous human or non-human sequences; and chimeric Fab fragment antibodies in which the FR and/or CDR1 and/or CDR2 and/or light chain CDR3 regions have been replaced by homologous human or non-human sequences.

According to the invention dog PGP inhibitors also include "dominant negative" polypeptides derived from SEQ ID NOs:2. A dominant negative polypeptide is an inactive variant of a polypeptide, which, by interacting with the cellular machinery, displaces an active polypeptide from its interaction with the cellular machinery or competes with the active polypeptide, thereby reducing the effect of the active polypeptide. For example, a dominant negative receptor which binds a ligand but does not transmit a signal in response to binding of the ligand can reduce the biological effect of expression of the ligand.

The end result of the expression of a dominant negative dog PGP polypeptide of the invention in a cell is a reduction in PGP activity such as molecular transport. One of ordinary skill in the art can assess the potential for a dominant negative variant of a dog PGP polypeptide, and using standard mutagenesis techniques to create one or more dominant negative variant polypeptides. For example, given the teachings contained herein of a dog PGP polypeptide, one of ordinary skill in the art can modify the sequence of the dog PGP polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in dog PGP activity and/or for retention of such an activity. Other similar methods for creating and testing dominant negative variants of a dog PGP polypeptide will be apparent to one of ordinary skill in the art.

Each of the compositions of the invention is useful for a variety of therapeutic and non-therapeutic purposes. For example, the dog PGP nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an anti-sense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning, A Laboratory Manual*, 2d ed., Cold Spring Harbor Laboratory Press, Plainview, N.Y. (1989). To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well-developed in the field of nucleic acid hybridization and, in general, many labels useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad Sci. (USA)* 80:4045 (1983); Renz, M. et al., *Nucl. Acids Res.* 12:3435 (1984); and Renz, M., *EMBO J.* 6:817 (1983).

Additionally, complements of the dog PGP nucleic acids can be useful as antisense oligonucleotides, e.g., by delivering the antisense oligonucleotide to an animal to induce a dog PGP "knockout" phenotype. The administration of antisense RNA probes to block gene expression is discussed in Lichtenstein, C., *Nature* 333:801–802 (1988).

Alternatively, the dog PGP nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of dog PGP knockout and transgenic animals as models for the study of disorders involving tranport of molecules across cell membranes. A variety of methods known to one of ordinary skill in the art are available for the production of transgenic animals associated with this invention.

Inactivation or replacement of the endogenous PGP/MDR1 gene can be achieved by a homologous recombination system using embryonic stem cells. The resultant transgenic non-human mammals having a $PGP^{\nu-}$ knockout phenotype may be made transgenic for the dog PGP and used as a model for screening compounds as modulators (agonists or antagonists/inhibitors) of the dog PGP. In this manner, such therapeutic drugs can be identified.

Additionally, a normal or mutant version of dog PGP can be inserted into the germ line to produce transgenic animals which constitutively or inducibly express the normal or mutant form of dog PGP. These animals are useful in studies to define the role and function of dog PGP in cells.

The compositions of the invention are also useful for therapeutic purposes. Accordingly the invention encompasses a method for inhibiting dog PGP activity in a mammalian cell. The invention further provides methods for reducing or increasing dog PGP activity in a cell. In one embodiment, the method involves contacting the mammalian cell with an amount of a dog PGP nucleic acid or polypeptide effective to inhibit molecular transport out of the mammalian cell. Such methods are useful in vitro for the purpose of, for example, elucidating the mechanisms involved in drug resistance and reduced drug bioavailability.

The invention also encompasses a method for increasing PGP expression in a cell or subject. The amount of dog PGP can be increased in such cell or subject by contacting the cell with, or administering to the subject, a PGP nucleic acid or a PGP polypeptide of the invention to the subject in an amount effective to increase transmembrane transport in the cell or the subject. An increase in PGP activity can be measured by the assays described herein, e.g., assays of transmembrane transport.

The preparations of the invention are administered in effective amounts. An effective amount is that amount of a pharmaceutical preparation that alone, or together with further doses, produces the desired response. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Generally, doses of active compounds would be from about 0.01 mg/kg per day to 1000 mg/kg per day. It is expected that doses ranging from 50–500 mg/kg will be suitable and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compound, although fewer doses typically will be given when compounds are prepared as slow release or sustained release medications.

When administered, the pharmaceutical preparations of the invention are applied in pharmaceutically-acceptable amounts and in pharmaceutically-acceptably compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The dog PGP inhibitors or dog PGP nucleic acids and polypeptides useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, or parenteral routes. The term "parenteral" includes subcutaneous, intravenous, intrathecal, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the dog PGP inhibitor or dog PGP nucleic acids and polypeptides, which is preferably isotonic with the blood of the recipient This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intrathecal, intramuscular, etc. administrations can be found in Remington's Pharmaceutical Sciences, Mack Publishing Co., Easton, Pa.

Other delivery systems can include time-release, delayed release or sustained release delivery systems such as the biological/chemical vectors is discussed above. Such systems can avoid repeated administrations of the active compound, increasing convenience to the subject and the physician. Many types of release delivery systems are available and known to those of ordinary skill in the art Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

EXAMPLES

Example 1

Isolation of Dog P-glycoprotein cDNA libraries were prepared using dog (*Canis familiaris*) mRNA according to standard procedures. The libraries were screened for P-glycoprotein clones using a human P-glycoprotein DNA probe. Clones were isolated, purified and sequenced in accordance with standard procedures, as described below.

Liver and lung tissue was excised from Beagle dog tissue samples and flash frozen in liquid nitrogen.

A 890bp fragment of dog PGP1 was PCRed out of a lambda gt11 vector cDNA library custom made by Stratagene. PCR was done using reagents from Clontech. Primers were custom designed, one specific for sequence homologous to human PGP1, the other homologous to dog PGP2.

| Primer name | sequence | size | SEQ NO: | homology |
|---|---|---|---|---|
| Dp1216F | 5'-gaa ctg tga ttg cgt ttg gag gac-3' | 24 mer | 9 | human PGP1 |
| Dp2133R | 5'-ttc agg gcc gcc tgt acc tct g-3' | 22 mer | 10 | dog PGP2 |

PCR was performed with a Perkin Elmer 9700 thermocycler. PCR was done at 94° C. for 2 minutes, followed by 40 cycles of 94° C. for 30 seconds, 40° C. for 20 seconds and 72° C. for 2 minutes and 30 seconds, and then incubated at 72° C. for 3 minutes. The PCR product was run on a 1% agarose gel, and stained with EtBr. The DNA band at 917 bp was cut out, and purified using the QIAquick Gel Extraction kit from Qiagen Inc.

The DNA was then ligated to the vector pCR2.1 using the Original TA Cloning kit from Invitrogen. INValphaF' cells were transformed with the ligation retain, a colony was selected, grown up in 100 mL of L broth with ampicillin. DNA purification was done using the Plasmid Midi purification kit from Qiagen. The insert was sequenced using an ABI 377 sequencer. This sequence corresponds to an 890 bp fragment of dog PGP, from base 816 to base 1706 in the open reading frame.

Five other fragments were isolated, cloned and sequenced using the same method as stated above, with any differences in procedure stated below.

RNA extraction from dog lung tissue was performed using Nucliobond RNA Maxi Prep. purification kit from Clontech. cDNA was synthesized from the RNA preparation using Superscript Preamplification System for First Strand cDNA Synthesis from Life Technologies.

Fragment 1: cDNA source - dog lung cDNA library prep.

| Primer name | sequence | size | SEQ NO: | homology |
|---|---|---|---|---|
| Dm1766F | 5'-ccc cac aga tgg cat ggt ctg t-3' | 22 mer | 11 | dog PGP1 |
| Dp2769R | 5'-cgc ttg gtg agg atc tct cca gc-3' | 23 mer | 12 | human PGP1 |

This corresponds to a 981 bp fragment of dog PGP from base 1364 to base 2345 in the open reading frame.

Fragment 2: cDNA source dog - lung cDNA library prep.

| Primer name | sequence | size | SEQ NO: | homology |
|---|---|---|---|---|
| Dm2037F | 5'-aga aac aga gaa tcg cca ttg ctc-3' | 24 mer | 13 | dog PGP1 |
| Dp3793R | 5'-gct gca gtc aaa cag gat ggg ct-3' | 23 mer | 14 | human PGP1 |

This corresponds to a 1728 bp fragment of dog PGP from base 1635 to base 3362 in the open reading frame.

Fragment 3: cDNA source dog - lung cDNA prep

| Primer name | sequence | size | SEQ NO: | homology |
|---|---|---|---|---|
| Dm3411F | 5'-agt tca ttt gct cct gac tat gcc-3' | 24 mer | 15 | dog PGP1 |
| Dp4214R | 5'-gat gcc ttt ctg ggc cag cag c-3' | 22 mer | 16 | human PGP1 |

This corresponds to a 779 bp fragment of dog PGP from base 3004 to base 3783 in the open reading frame.

An RNA preparation from dog liver tissue was performed using the same method as used previously. cDNA was made from it using the SMART RACE cDNA Amplification Kit from Clontech using SMART II oligonucleotide. PCR conditions were changed to 94° C. for 5 minutes, followed by 5 cycles of 94° C. for 30 seconds and 72° C. for 2 minutes. Five cycles of 94° C. for 30 seconds, 70° C. for 45 seconds and 72° C. for 2 minutes were performed next. The final 30 cycles were at 94° C. for 30 seconds, 68° C. for 45 seconds and 72° C. for 2 minutes. The PCR was concluded with 72° C. for 7 minutes.

| Fragment 4: cDNA source - dog liver cDNA (SMART RACE) prep. | | | | |
|---|---|---|---|---|
| Primer name | sequence | size | SEQ NO: | homology |
| Dm3612FL | 5'-gag gtg aag aag ggc cag acg ctg gcc ctc-3' | 30 mer | 17 | dog PGP1 |
| RACE | 5'-cta ata cga ctc act ata ggg caa gca gtg gta aca acg cag agt 3' | | 18 | vector |

This corresponds to a 3' end fragment of dog PGP from base 3212 to base 4264 in the open reading frame.

An RNA preparation from dog liver tissue was performed using the same method as used previously. cDNA was made from it using the SMART RACE cDNA Amplification Kit from Clontech using the gene specific Primer DM1680RL 5'-cgc agc cac tgt tcc caa cca gcg cca ct-3', 29 mer, SEQ ID NO:19, dog PGP1.

| Fragment 5: cDNA source - dog liver cDNA (SMART RACE with internal primer) prep. | | | | |
|---|---|---|---|---|
| Primer name | sequence | size | SEQ NO: | homology |
| Dp409F | 5'-gga gcg cga ggt cgg gat gga tc-3' | 23 mer | 20 | human PGP1 |
| Dm1355RL | 5'-gga gag gac caa gga ggt ccc ata cca gaa a-3' | 31 mer | 21 | dog PGP1 |

This corresponds to an ATG fragment of dog PGP from base −15 to base 945 in the open reading frame.

Assembly of Clones

1 Kb fragment (890 bp) and 981 bp fragment

DNA preps were made of each fragment. Both fragments were cut with NcoI restriction enzyme. The 1 Kb fragment was also cut with EcoRI. The 981 bp fragment was also cut with BamHI. Each fragment was purified, ligated together, then the ends were cut, the cut molecule was gel purified and ligated into pUC19 cut with EcoRI and BamHI.

1 Kb fragment (890 bp)/981 bp fragment and 1728 bp fragment

These fragments were assembled as above except that both fragments were cut with BamHI and the 1728 bp fragment was also cut with XbaI.

1 Kb fragment (890 bp)/981 bp fragment/1728 bp fragment and ATG fragment 3'end and 779 bp fragment 1 Kb fragment (890 bp)/981 bp fragment/1728 bp fragment ATG fragment and 3'end/779bp fragment All of these fragments were assembled as above except that, in some cases, the fragments were cut with different restriction enzymes according to their nucleotide sequences.

The nucleotide sequence of a dog P-glycoprotein is presented as SEQ ID NO:1. The coding sequence consists of nucleotides 17–3859, producing a polypeptide of 1281 amino acids (SEQ ID NO:2).

Example 2

Activity of Dog P-glycoprotein

Materials and Methods

Dog PGP cDNA (SEQ ID NO:1) is introduced into a clonal population of LLC-PK1 cells in a vector that confers resistance to hygromycin B. LLC-PK1 cells are obtained from the American Type Culture Collections and are propagated in Medium 199 supplemented to 7% with fetal bovine serum. LLC-PK1 cells are recloned prior to transfection in order to assure homogeneity of the cell population. Briefly, dog PGP cDNA is incorporated into the p222CMV vector. This vector is derived from the p220.2 episomal vector system based on the OriP sequences for Epstein Barr virus and the EBNA-1 gene product (Sugden et al., *Mol. Cell Biol.* 5:410–413, 1985; Yates et al., *Nature* (Lond.) 313: 812–815, 1985). The PGP cDNA is under the control of the cytomegalovirus (CMV) immediate early promoter. The vector confers resistance to hygromycin B. Cells (in 0.4 mL) and DNA (10 to 20 $\mu$g) were transfected by electroporation using a BTX Electro cell manipulator model 600 using a 2 mm gap cell, 100V, 2500 $\mu$F capacitance and 72 ohm resistance.

After electroporation, the cells are plated in multiwell plates (48 well, Corning Costar) at 10% of confluence. One to two days after transfection hygromycin B is introduced at a final concentration of 400 to 600 $\mu$g/ml. Cells are refed every 2 to 4 days and are propagated in 400 to 600 $\mu$g/ml hygromycin B for 6 to 8 days at which point the bulk of the wild type cells are detached. The hygromycin B is reduced to 100 $\mu$g/ml and maintained in this concentration of hygromycin B. After 14 to 18 days the wells are inspected and wells containing single colonies are trypsinized and scaled up to bulk cultures. Expression of PGP is measured by the polarization of vinblastine (0.1 uM) transport in Transwells™.

LLC-PK1 cell based transport studies are conducted in 24 well Transwells™ (Corning Costar, Catalog number 3415). Transwells™ are prepared by the addition of 0.6 mL media to the basolateral space and 0.1 mL media to the apical space. Cells are seeded at $4\times10^4$ cells per insert (typically in 0.05 mL to 0.15 mL), refed with fresh media every 2 to 4 days and used for transport studies 4 to 8 days post seeding. Transport assays are conducted in Hank's balanced saline (HBSS) buffered with 10 mM HEPES (pH 7 to 7.2). Cell monolayers are rinsed with HBSS prior to use in transport assays. Transport is measured under sink conditions in both the apical to basolateral (A to B) and basolateral to apical (B to A) directions. At least duplicate monolayers are used per determination. At the desired time points, samples are withdrawn from the receiver chamber (apical or basolateral chambers). Quantitation of the amount of compound transported is by liquid scintillation counting (vinblastine) or HPLC with UV or mass spectrometric detection.

Dog PGP cDNA is expressed in insect cells using a baculovirus vector. Membranes are prepared according to the method of (Sarkadi et al., *J Biol. Chem.* 267: 4854–4858, 1992) and stored at −80° C. until use. ATPase assays are conducted in 96 well microtiter plates. The assays are conducted using a modification of the methods of (Sarkadi et al., 1992 and Druekes et al., *Anal. Biochem.* 230: 173–177, 1995).

A detailed method for each well of a 96 well plate is contained below: A 0.06 ml reaction mixture containing 40 µg membranes, 20 µM Verapamil (positive control) or test drug, and 3–5 mM MgATP, in buffer containing 50 mM Tris-MES, 2 mM EGTA, 50 mM KCl, 2 mM dithiothreitol, and 5 mM sodium azide, is incubated at 37° C. for 20 min. An identical reaction mixture containing 100 µM sodium orthovanadate is assayed in parallel. Orthovanadate inhibits PGP by trapping MgADP in the nucleotide binding site. Thus, ATPase activity measured in the presence of orthovanadate represents non-PGP ATPase activity and can be subtracted from the activity generated without orthovanadate to yield vanadate-sensitive ATPase activity. The reaction is stopped by the addition of 30 µl of 10% SDS+ Antifoam A. Two additional reaction mixtures (+and− orthovanadate) but without MgATP, are also prepared and incubated with the others, and then supplemented with SDS and MgATP, to represent time=0 min of reaction. The incubations are followed with addition of 200 µl of 35 mM ammonium molybdate in 15 mM zinc acetate:10% ascorbic acid (1:4) and incubated for an additional 20 min at 37° C. The liberation of inorganic phosphate is detected by its absorbance at 800 nm and quantitated by comparing the absorbance to a phosphate standard curve.

Ligand binding assays and assays for measuring inhibition of fluorescent dye uptake are preformed as described by Sharom et al. (*Biochem. Pharmacol.* 58:571–586, 1999).

I. Stable PGP Expression in LLC-PK1 Cells.

Functional expression of dog PGP is measured by the polarization of transport of vinblastine. Control cells typically demonstrate a B to A/A to B ratio of between 1 and 3. PGP transfected cells demonstrate a much higher ratio. The expression of cDNA-derived dog is stable.

II Activation of ATPase Activity in PGP Membranes.

The stimulation of ATPase assay provides a rapid measure of the concentration dependence of any interaction of a drug with PGP. The liberated inorganic phosphate is measured by a simple spectrophotometric assay performed in a microtiter plate format. The testing of multiple drug concentrations allows estimation of the affinity of the drug for PGP and whether saturation of the response was observed.

III. Drug Transport Across Cell Monolayers.

The ATPase assay does not directly measure drug transport. In order to examine the concordance between activation of ATPase and actual transport, the rates of transport of the drugs are measured in control LLC-PK1 and dog PGP cell monolayers. For each drug concentration, four measurements are made:

| A: | A to B | Control cells |
|---|---|---|
| B: | B to A | Control cells |
| C: | A to B | PGP cells |
| D: | B to A | PGP cells |

The polarization of transport is calculated in control cells (B/A) and PGP cells (D/C). The intrinsic activity (IA) of PGP is calculated as the sum of the amount PGP facilitated B to A transport in PGP cells relative to control cells (D minus B) and the amount that PGP impeded A to B transport in PGP cells relative to control cells (A minus C). The intrinsic clearance of PGP is calculated from a plot of the concentration dependence data by either calculating the slope of the line under non-saturating conditions or from the calculated apparent Km and Vmax values when saturation is observed. Intrinsic clearance is expressed as mL/m²/min.

The ATPase data provides useful concentration response data. For example, the apparent Km values for some compounds are in good agreement between the ATPase and transport systems. However, other drugs activate ATPase activity but transport by PGP is not detectable. At the least, ATPase assay can identify a concentration range below which the response to transport by PGP was linear with respect to drug concentration. This should allow simplification of the experimental design for measuring the intrinsic clearance of PGP, an important consideration if large numbers of compounds are to be tested.

IV Bioavailability

Bioavailability studies are performed by performing one or more of the assays described above with two or more different PGP types. The different PGP types can by different species (e.g., dog and human, cynomologous monkey and human, dog and cynomologous monkey, etc.) or can be different alleles of the same species. The results of these assays are compared to determine or estimate the bioavailability of a drug in individuals of the different species or in individuals that express different PGP alleles. The results of one determination also may be compared to a previously determined value of, e.g., ATPase or transport, as an historical control.

Protocols and Procedures

Isolation of RNA

Frozen beagle liver tissue was ground up using a mortar and pestle. Pulverized tissue (300 mg) was transferred to a dounce homogenizer. TRIsol Reagent (3 mL; Cat. #15596 from Life Technologies) was added and the tissue was homogenized then incubated for 15 minutes at room temperature. Aliquots (1 mL) of the solution were transferred to three microfuge tubes and 200 µL of chloroform were added to each tube. Each tube was vortexed at a high setting for 15 seconds, then incubated at room temperature for 3 minutes before being centrifuged at 10 000 g for 15 minutes at 4° C. The upper "aqueous" phase was transferred to a new microfuge tube while the remaining lower and inter phases were discarded. 500 µL of Isopropanol was added to each of the new tubes and mixed by inverting the tube several times. Each tube was then incubated at room temperature for 10 minutes before being centrifuged at 10 000 g for 10 more minutes at 4° C. A small white pellet was observed and the supernatant was discarded. 1 mL of 75% ethanol was added to each tube. The tubes were vortexed briefly then centrifuged at 10 000 g for 10 minutes at 4° C. The supernatant was discarded and the pellet dried for 5 minutes at room temperature. 50 µL of DEPC treated sterile deionized water was added to each tube. Each pellet was resuspended and the contents of each tube were pooled.

Optical density of the resuspended pellet was analyzed using a Hitachi U3010 spectrophotometer to determine the quantity of RNA that was isolated. The RNA was then diluted using DEPC treated sterile deionized water to a concentration of 0.55 µg/µL. 2 mL of this RNA was split evenly into 2 microfuge tubes. Next, 100 µL of 5 M NaCl was added to each tube. Both tubes were heated to 65° C. for 15 minutes, then put on ice for 5 minutes. 500 µL of Oligo (dT) Cellulose Suspension from the MessageMaker mRNA Isolation System (Cat. # 10551-018 from Life Technologies) were added to both tubes. The tubes were then incubated at 37° C. for 10 minutes. The contents of the tubes were transferred to the Filter Syringe provided with the MessageMaker mRNA Isolation System. After expelling the liquid contents, the pellet in the syringe was washed using Wash Buffer 1 and Wash Buffer 2 according to the manufacturer's instructions. The RNA pellet in the syringe was resuspended in 1 mL of DEPC treated sterile deionized water (65° C), followed by the addition of 2.5 µL of 50 µg/mL glycogen and 100 µL of 7.5M ammonium acetate and mixing by inversion. The contents of the tube were then transferred to a two microfuge tubes and 1 mL of ethanol was added to each tube. The contents of both tubes were mixed by inversion, followed by incubation at −20° C. overnight.

The tubes were centrifuged at 10 000 g for 30 minutes at 4° C. The supernatant was discarded and 200 µL of 75% ethanol was added to each tube. The tubes were vortexed for 10 seconds followed by centrifugation at 10 000 g for 15 minutes at 4° C. The supernatant was discarded and all remaining liquid was carefully pipetted off. The pellet was resuspended in 10 µL of DEPC treated sterile deionized water.

Preparation of cDNA cDNA was prepared using the Marathon cDNA Amplification Kit (Cat. # K1802-1 from Clontech Laboratories, Inc., Palo Alto, Calif.) as follows. Four microliters of the resuspended mRNA were transferred to a new microfuge tube, and 1 µL of one of the following primers at 10 µM concentration was added: Dm1680RL cgc age cac tgt tcc caa cca gcg cca ct (SEQ ID NO:19; custom designed, synthesized by Operon Technologies, Inc.) or cDNA Synthesis Primer, nnt ttt ttt ttt ttt ttt ttt ttt ttt ttt ttc gcc ggc gac tta aga tct t (SEQ ID NO:28), from the Marathon cDNA Amplification Kit. Tubes were incubated at 70° C. for 2 minutes then placed on ice for 5 minutes. 2 µL of 5×First-Strand Buffer, 1 µL of 10 mM dNTP Mix and 1 µL of 20 U/µL AMV Reverse Transcriptase were added to each tube and gently mixed. The tubes were incubated at 42° C. for 1 hour, then placed on ice. 2 µL of each single stranded cDNA were used as template in PCR (see below, "PCR conditions"). 48.4 µL of DEPC treated deionized water, 16 µL of 5×Second-Strand Buffer, 1.6 µL of 10 mM dNTP Mix and 4 µL of 20×Second-Strand Enzyme Cocktail were added to the remaining cDNA sample. The tube was incubated at 16° C. for 1.5 hours. 2 uL of 5U/uL T4 DNA Polymerase was added to the tube, which was then incubated at 16° C. for an additional 45 minutes. 20×EDTA/Glycogen Mix (4 µL) was added followed by 430 µL of Buffer PN from the QIAquick Nucleotide Removal Kit (Cat. #28304 from QIAGEN Inc., Valencia, Calif.). The sample was then loaded into a QIAquick Spin Column and centrifuged at 10 000 g for 1 minute. The collection tube was emptied and 750 µL of PE Buffer (QIAGEN) were added to the QIAquick Spin Column which was again centrifuged at 10 000 g for 1 minute. The collection tube was once again emptied and the QIAquick Spin Column was centrifuged at 10 000 g for 1 minute to dry the column membrane. 50 µL of sterile deionized water heated to 50° C. was added to the QIAquick Spin Column and incubated at room temperature for 1 minute before being centrifuged at 10 000 g for 1 minute into a clean microfuge tube.

To precipitate nucleic acid, 10.8 µL 7.5M ammonium acetate and 144 µL ethanol were added to the tube before it was centrifuged at 10 000 g for 20 minutes. The supernatant was removed, then 300 µL of 75% ethanol was added. The tube was vortexed and centrifuged at 10 000 g for 20 minutes. The supernatant was removed and the sample was resuspended in 12 µL of sterile deionized water. 5 µL of this cDNA were placed in a clean microfuge tube. 2 µL of 10 µM Marathon cDNA Adapter, 2 µL 5×DNA Ligation Buffer and 1 µL of 400U/µL T4 DNA Ligase, from the Marathon cDNA Amplification Kit, were added to the cDNA and mixed gently. This mixture was incubated over night at 16° C. The ligase was heat inactivated at 70° C. for 5 minutes. PCR was done using this sample as a template.

PCR Conditions

PCR was performed using reagents supplied with the Clontech Advantage 2 kit (Clontech, palo Alto, Calif.). Briefly, 2 µL of cDNA was placed in a 200 µL MicroAmp reaction tube (Cat. # N801-0540, PE Biosystems), then 34 µL of sterile deionized water, 5 µL of 10×Clontech Advantage 2 Polymerase Mix (Cat. #4700-1 Clontech Laboratories, Inc.), 3 µL of 10 mM Advantage UltraPure PCR Deoxynucleotide Mix (Cat. #8430-1 Clontech Laboratories, Inc.) and 2 µL each of a forward and reverse primer at 10 mM concentration were added. Primers were either Marathon cDNA Adapter Primer 1, cca tcc taa tac gac tca ctg tag ggc (SEQ ID NO:29), from the Marathon cDNA Amplification Kit or various custom gene specific primers made by Operon Technologies Inc. Custom primers include (all listed as 5'-3'): Dm409FL: gga gcg cga ggt cgg gat gga tc (SEQ ID NO:20), Dm1455RL: gca aat gct tca atg ctt ggg gat gcc tgt cca a (SEQ ID NO:30), Dm2037F: aga aac aga gaa tcg cca ttg ctc (SEQ ID NO:13), Dm3920RL: gag ctg ggt tcc ttt gtc tcc tac tct ggt gtt (SEQ ID NO:31), Dp1216F: gaa ctg tga ttg cgt ttg gag gac (SEQ ID NO:9), and Dp2587R: gca aat gct ggt tgc agg cct cc (SEQ ID NO:32).

Thermocycling was done using a Perkin Elmer 9700 at 94° C. for 30 seconds followed by 2 cycles of 94° C. for 5 seconds and 72° C. for 4 minutes, followed by 16 cycles of 94° C. for 5 seconds and 68° C. for 4 minutes.

Four fragments were acquired by PCR for each Genotype. Fragment 1 was generated using primers Marathon cDNA Adapter Primer 1 and Dm1455RL. Fragment 2 was generated using primers Dp1216F and Dp2587R. Fragment 3 was generated using primers Dm2037F and Dm3920RL. Fragment 4 was generated using primers Dp3612FL and Marathon cDNA Adapter Primer 1.

Post PCR Sample Processing

Electrophoresis was performed on all PCR products using 10×Gel-loading Buffer IV (*Molecular Cloning: A Laboratory Manual*, J. Sambrook, et al., eds., Second Edition, Cold Spring Harbor Laboratory Press, Cold Spring Harbor, N.Y., 1989, page 6.12), on a 1% agarose gel in 0.5×TBE buffer (Sambrook, et al., page B-23) containing EtBr. Fragments of gel containing the PCR products were cut out and placed in 2 mL microfuge tubes. The mass of each fragment was determined and 3 µL/mg of Buffer QX1 from QIAquick Gel Extraction Kit (Cat. #28704 from QIAGEN Inc.) was added. Each tube was then incubated for 10 minutes at 50° C. with mixture every two minutes. 1 µL/mg of isopropanol was added to each tube and mixed. The resulting solution was transferred to a QIAquick spin column from the QIAquick Gel Extraction Kit. These columns were centrifuged for 1 minute at 10 000 g at room temperature. 750 μL of Buffer PE from the QIAquick Gel Extraction Kit were added to each column followed by centrifugation for 1 minute at 10 000 g at room temperature. Each column was centrifuged again for 1 minute at 10 000 g at room temperature to remove any residual buffer. 30 μL of sterile deionized water at 50° C. were added to each column and incubated for 1 minute at room temperature. Each column was then placed in a microfuge tube and centrifuged for 1 minute at 10 000 g.

Next, 6 μL of purified PCR product was transferred to a clean microfuge tube and 1 pL of 10×Ligation Buffer, 2 μL of pCR 2.1 vector and 1 uL of T4 DNA Ligase (all from the Original TA Cloning Kit (Cat. #K2000-J10) Invitrogen, Carlsbad, Calif.) were added to the microfuge tube and mixed. The reaction was incubated over night at 16° C.

One 50 μL vial of frozen One Shot competent cells (Invitrogen) was thawed on ice for each ligation reaction. 3.5 uL of ligation reaction mixture was added to the competent cells and gently mixed. The cells incubated on ice for 30 minutes, followed by a 30 second "heat shock" at 42° C. After cooling on ice again, 250 μL of SOC medium (Invitrogen) was added to each vial and the vials were put directly into a 37° C. water bath for 1 hour. 50 μL and 200 μL aliquots of each transformation reaction were plated on Luria-Bertani Medium (Sambrook et al., page A-1) containing 1% agarose, 1 mg/mL glucose, 50 ng/mL ampicillin and 1.6 ng/mL X-gal. The inoculated plates were then incubated at 37° C. overnight. White colored colonies were selected and used to inoculate separate 100 mL cultures of L-B Medium containing 50 ng/mL ampicillin which were incubated at 37° C. overnight while being stirred at 100 rpm.

Plasmid DNA was prepared using QIAGEN Midi Plasmid Kit (Cat. #12143 from QIAGEN Inc.), according to the manufacturer's instructions, as follows. Each 100 mL culture was aliquoted into two 50 mL conical vials and centrifuged at 3 000 g for 10 minutes at 4° C. The supernatant was poured off and 4 mL of Buffer P1 were used to resuspend the pellet in one of the two vials. This suspension was transferred to the other tube and used to resuspend that pellet. Buffer P2 (4 mL) was added, mixed and the suspension was incubated at room temperature for 5 minutes. Buffer P3 (4 mL) was added, mixed and the suspension was incubated at 4° C. for 15 minutes. The samples were centrifuged at 3 000 g for 15 minutes at 4° C. All of the supernatant was transferred to a QIAgen-tip 100 that had been previously treated with 4 mL of Buffer QBT. The supernatant was allowed to drain through the column. Buffer QC (10 mL) was added to the column and allowed to drain. Another 10 mL of Buffer QC was added and allowed to drain. Finally 4 mL of Buffer QF was added to the column and allowed to drain into a clean 15 mL conical vial. 2.8 mL of isopropanol was added and mixed with this solution. This was aliquoted into microfuge tubes, incubated at 4° C. for 10 minutes and centrifuged at 10 000 g for 15 minutes at 4° C. The supernatant was removed, then 1 mL of 70% ethanol was added to each microfuge tube. Each tube was vortexed briefly, then centrifuged at 10 000 g for 15 minutes at 4° C. The supernatant was removed and 100 μL of sterile 1×TE buffer (Sambrook et al., page B-20) were added.

Restriction digests were performed on the purified DNA. Enzymes used to cut fragments out were: fragment 1, KpnI (Cat. #R0142S from New England Biolabs, Inc., Beverly, Mass.) and NsiI (Cat. #R0127S from New England Biolabs, Inc.); fragment 2, NsiI and HindIII (Cat. #R0104S from New England Biolabs, Inc.); fragment 3, HindIII and PstI (Cat. #V0279S from New England Biolabs, Inc.); and fragment 4, PstI and NotI (Cat. #R0189S from New England Biolabs, Inc.). All restriction digests were preformed at 37° C. in digestion buffers recommended by New England Biolabs.

Electrophoresis was performed on all restriction digest products using 10×gel-loading buffer IV (Sambrook et al., page 6.12), on a 1% agarose gel in 0.5×TBE buffer (Sambrook et al., page B-23) containing EtBr. Fragments of gel containing the restriction digest products were cut out and placed in 2 mL microfuge tubes. DNA fragments were extracted from the gel slices using a QIAquick Gel Extraction Kit (Cat. #28704 from QIAGEN Inc.) according to the manufacturer's instructions. The mass of each fragment was determined and 3 μL/mg of Buffer QX1 was added. Each tube was then incubated for 10 minutes at 50° C. with mixture every two minutes. One volume of isopropanol was added to each tube and mixed. The resulting solution was transferred to a QIAquick spin column and centrifuged for 1 minute at 10 000 g at room temperature. Buffer PE (750 μL) was added to each column followed by centrifugation for 1 minute at 10 000 g at room temperature. Each column was centrifuged again for 1 minute at 10 000 g at room temperature to remove any residual buffer. 30 μL of sterile deionized water at 50° C. was added to each column and incubated for 1 minute at room temperature. Each column was then placed in a microfuge tube and centrifuged for 1 minute at 10 000 g.

Two microliters of each fragment was added to a microfuge tube as well as 1 μL of 10×Ligation Buffer and 1 μL of T4 DNA Ligase (Cat. #M0202S from New England Biolabs, Inc.). This reaction was incubated at 16° C. overnight. Restriction enzymes KpnI and NotI (1 μL each) were added to the reaction and incubated at 37° C. for 1 hour. Electrophoresis was performed using 10×Gel-loading Buffer IV on a 1% agarose gel in 0.5×TBE buffer containing EtBr. The fragment of gel containing the assembled product was cut out and the DNA fragment was extracted using a QIAquick Gel Extraction Kit as described above.

The fragment was ligated into a vector using an Original TA Cloning Kit, as follows: 6 μL of purified DNA were transferred to a clean microfuge tube and 1 uL of 10×Ligation Buffer, 2 μL of pCR 2.1 vector (previously digested with KpnI and NotI), and 1 μL of T4 DNA Ligase were added and mixed. The reaction was incubated over night at 16° C. The ligation reaction mixture (3.5 μL) was used to transform One Shot competent cells as described above, 50 uL and 200 uL aliquots of the transformation reaction were plated on Luria-Bertani Medium containing 1% agarose, 1 mg/mL Glucose, 50 ng/mL Ampicillin and 1.6 ng/mL X-gal and grown as described above. White colored colonies were selected and grown as described above. Plasmid DNA was isolated and purified using a QIAGEN Midi Plasmid Kit as described above. DNA was resuspended in 100 μL of sterile 1×TE buffer. This DNA was then sequenced using ABI 100 DNA sequencer (from ABI) by Tufts University Core Facility.

Identification of Four Genotypes of Dog P-glycoprotein

The dog P-glycoprotein identified in Example 1 is now termed genotype C. Sequencing of the DNA isolated from beagle liver as described in this example permitted the identification of three additional allelic variants of dog P-glycoprotein, termed genotypes A, B and D. the allelic differences in DNA sequence are set forth in Table 1 below.

TABLE 1

Nucleotide and Amino Acid Differences Between Dog P-glycoprotein Genotypes (Allelic Variants)

| SEQ ID NO: | | | Nucleotide position | | | | Amino acid position | | | |
|---|---|---|---|---|---|---|---|---|---|---|
| DNA | Protein | Genotype | 91 | 607 | 1001 | 3458 | 25 | 197 | 329 | 1148 |
| 22 | 23 | A | T | A | T | A | N | Q | S | M |
| 24 | 25 | B | A | A | T | A | K | Q | S | M |
| 1 | 2 | C | T | C | T | A | N | H | S | M |
| 26 | 27 | D | A | A | A | G | K | Q | T | V |

Genotype A has a different nucleotide at base number 607 relative to SEQ ID NO:2. This is a base change from C to A in the DNA sequence which causes an amino acid change from Histidine to Glutamine at amino acid 197. Genotype B has different nucleotides at base number 91 and 607 relative to SEQ ID NO:2. The base change at position 91 is from T to A and causes an amino acid change from Asparagine to Lysine at amino acid 25. Base change at position 607 is identical to that in Genotype A. Genotype D has different nucleotides at base number 91, 607, 1001 and 3458 relative to SEQ ID NO:2. Base changes at position 91 and 607 are identical to that in Genotype B. The base change at position 1001 is from T to A and causes an amino acid change from Serine to Threonine at amino acid 329. The base change at position 3458 is from A to G and causes an amino acid change from Methionine to Valine at amino acid 1148.

A previously identified dog P-glycoprotein (SEQ ID NOs:3 and 4; GenBank Accession number AF045016), has 13 nucleotide differences from the genotype C dog P-glycoprotein nucleotide sequence (SEQ ID NO:1). There is a 3 base deletion at base 89 to base 91 (relative to SEQ ID NO:1) leaving out AAT which causes a deletion of amino acid 25 Asparagine. There is a base change from A to G at position 590 which causes an amino acid change from Isoleucine to Valine at amino acid 192. There is a base change from C to A at position 607 which causing an amino acid change from Histidine to Glutamine at amino acid 197. There is a base change from G to C at position 651 which causes an amino acid change from Arginine to Proline at amino acid 212. There is a base change from G to A at position 878 which causes an amino acid change from Glycine to Arginine at amino acid 288. There is, a base change from T to A at position 1001 which causes an amino acid change from Serine to Threonine at amino acid 329. There is a base change from A to G at position 1012 which does not cause an amino acid change. This is a silent point mutation at Glutamine, amino acid 332. There is a base change from A to G at position 1611 which causes an amino acid change from Glutamine to Arginine at amino acid 532. There is a base change from A to T at position 2098 which does not cause an amino acid change. This is a silent point mutation at Valine, amino acid 694. There is a base change from C to T at position 2102 which causes an amino acid change from Proline to Serine at amino acid 696. There is a base change from C to T at position 3808 which does not cause an amino acid change. This is a silent point mutation at Alanine, amino acid 1264. There is a base change from G to A at position 3833 which causes an amino acid change from Valine to Isoleucine at amino acid 1273. There is a base change from C to T at position 4080 which causes an amino acid change from Threonine to Isoleucine at amino acid 1355.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. An isolated nucleic acid molecule that codes for the amino acid sequence of SEQ ID NO:2 and complements thereof.

2. An isolated nucleic acid molecule that codes for the amino acid sequence of SEQ ID NO:2, wherein the isolated nucleic acid comprises the nucleotide sequence of SEQ ID NO:1.

3. An isolated nucleic acid molecule that codes for the amino acid sequence of SEQ ID NO:2, wherein the isolated nucleic acid comprises the coding region of SEQ ID NO:1.

4. An expression vector comprising the isolated nucleic acid molecule of claim 1 operably linked to a promoter.

5. A host cell transformed or transfected with the expression vector of claim 4.

* * * * *

SEQUENCE LISTING

<160> NUMBER OF SEQ ID NOS: 32

<210> SEQ ID NO 1
<211> LENGTH: 4279
<212> TYPE: DNA
<213> ORGANISM: Canis familiaris
<220> FEATURE:
<221> NAME/KEY: CDS
<222> LOCATION: (17)...(3859)

<400> SEQUENCE: 1

```
ggagcgcgag gtcggg atg gat cct gaa gga ggc cgt aag ggg agt gca gag      52
               Met Asp Pro Glu Gly Gly Arg Lys Gly Ser Ala Glu
                 1               5                  10 aag aac ttc tgg aaa atg ggc aaa aaa agt aaa aaa aat gag aag aaa      100
Lys Asn Phe Trp Lys Met Gly Lys Lys Ser Lys Lys Asn Glu Lys Lys
         15                  20                  25
```

```
gaa aag aaa cca act gtc agc acg ttt gca atg ttt cgc tat tca aat      148
Glu Lys Lys Pro Thr Val Ser Thr Phe Ala Met Phe Arg Tyr Ser Asn
     30                  35                  40 tgg ctt gat agg ttg tat atg ttg gtg ggg aca atg gct gcc atc atc      196
Trp Leu Asp Arg Leu Tyr Met Leu Val Gly Thr Met Ala Ala Ile Ile
 45                  50                  55                  60 cat gga gct gca ctc cct ctc atg atg ctg gtt ttt gga aac atg aca      244
His Gly Ala Ala Leu Pro Leu Met Met Leu Val Phe Gly Asn Met Thr
                 65                  70                  75 gat agc ttt gca aat gca gga att tca aga aac aaa act ttt cca gtt      292
Asp Ser Phe Ala Asn Ala Gly Ile Ser Arg Asn Lys Thr Phe Pro Val
             80                  85                  90 ata att aat gaa agt att acg aac aat aca caa cat ttc atc aac cat      340
Ile Ile Asn Glu Ser Ile Thr Asn Asn Thr Gln His Phe Ile Asn His
         95                 100                 105 ctg gag gag gaa atg acc acg tat gcc tat tat tac agt ggg atc ggt      388
Leu Glu Glu Glu Met Thr Thr Tyr Ala Tyr Tyr Tyr Ser Gly Ile Gly
    110                 115                 120 gct ggc gtg ctg gtg gct gct tac atc cag gtt tca ttc tgg tgc ctg      436
Ala Gly Val Leu Val Ala Ala Tyr Ile Gln Val Ser Phe Trp Cys Leu
125                 130                 135                 140 gca gca gga aga cag ata ctc aaa att aga aaa caa ttt ttt cat gct      484
Ala Ala Gly Arg Gln Ile Leu Lys Ile Arg Lys Gln Phe Phe His Ala
                145                 150                 155 atc atg cga cag gag att ggc tgg ttt gac gtg cat gac gtt ggg gag      532
Ile Met Arg Gln Glu Ile Gly Trp Phe Asp Val His Asp Val Gly Glu
            160                 165                 170 ctt aac acc cgg ctc aca gac gat gtc tcc aaa atc aat gaa gga att      580
Leu Asn Thr Arg Leu Thr Asp Asp Val Ser Lys Ile Asn Glu Gly Ile
        175                 180                 185 ggc gac aaa att gga atg ttc ttt cac tca ata gca aca ttt ttc acc      628
Gly Asp Lys Ile Gly Met Phe Phe His Ser Ile Ala Thr Phe Phe Thr
190                 195                 200 ggt ttt ata gtg ggg ttt aca cgt ggt tgg aag cta acc ctt gtg att      676
Gly Phe Ile Val Gly Phe Thr Arg Gly Trp Lys Leu Thr Leu Val Ile
205                 210                 215                 220 ttg gcc atc agc cct gtt ctt gga ctt tca gcc gcc atc tgg gca aag      724
Leu Ala Ile Ser Pro Val Leu Gly Leu Ser Ala Ala Ile Trp Ala Lys
                225                 230                 235 ata cta tct tca ttt act gat aaa gaa ctc ttg gcc tat gca aaa gct      772
Ile Leu Ser Ser Phe Thr Asp Lys Glu Leu Leu Ala Tyr Ala Lys Ala
            240                 245                 250 gga gca gta gct gaa gaa gtc tta gca gca atc aga act gtg att gcc      820
Gly Ala Val Ala Glu Glu Val Leu Ala Ala Ile Arg Thr Val Ile Ala
        255                 260                 265 ttt gga gga caa aag aaa gaa ctt gaa agg tac aac aaa aat tta gaa      868
Phe Gly Gly Gln Lys Lys Glu Leu Glu Arg Tyr Asn Lys Asn Leu Glu
270                 275                 280 gaa gct aaa gga att ggg ata aag aaa gct atc acg gcc aac att tct      916
Glu Ala Lys Gly Ile Gly Ile Lys Lys Ala Ile Thr Ala Asn Ile Ser
285                 290                 295                 300 att ggt gcc gct ttc tta ttg atc tat gca tca tat gct ctg gct ttc      964
Ile Gly Ala Ala Phe Leu Leu Ile Tyr Ala Ser Tyr Ala Leu Ala Phe
                305                 310                 315 tgg tat ggg acc tcc ttg gtc ctc tcc agt gaa tat tct att gga caa     1012
Trp Tyr Gly Thr Ser Leu Val Leu Ser Ser Glu Tyr Ser Ile Gly Gln
            320                 325                 330 gta ctc act gtc ttc ttt tct gta tta att ggg gct ttt agt att gga     1060
Val Leu Thr Val Phe Phe Ser Val Leu Ile Gly Ala Phe Ser Ile Gly
```

```
                    335                 340                 345
cag gca tcc cca agc att gaa gca ttt gca aac gca aga gga gca gct     1108
Gln Ala Ser Pro Ser Ile Glu Ala Phe Ala Asn Ala Arg Gly Ala Ala
350                 355                 360 tat gaa atc ttc aag ata att gac aat aaa cca agc att gac agc tat     1156
Tyr Glu Ile Phe Lys Ile Ile Asp Asn Lys Pro Ser Ile Asp Ser Tyr
365                 370                 375                 380 tcg aag agt gga cat aaa cca gat aat att aag gga aat ttg gaa ttc     1204
Ser Lys Ser Gly His Lys Pro Asp Asn Ile Lys Gly Asn Leu Glu Phe
                    385                 390                 395 aaa aat gtt cac ttc agt tac cct tct cga aaa gaa gtt aag atc tta     1252
Lys Asn Val His Phe Ser Tyr Pro Ser Arg Lys Glu Val Lys Ile Leu
                400                 405                 410 aag ggt ctc aac ctg aag gtt cag agt ggg cag aca gtg gcg ctg gtt     1300
Lys Gly Leu Asn Leu Lys Val Gln Ser Gly Gln Thr Val Ala Leu Val
            415                 420                 425 ggg aac agt ggc tgc ggg aag agc acg acc gtg cag ctg atg cag agg     1348
Gly Asn Ser Gly Cys Gly Lys Ser Thr Thr Val Gln Leu Met Gln Arg
        430                 435                 440 ctc tat gac ccc aca gat ggc atg gtc tgt att gat gga cag gac att     1396
Leu Tyr Asp Pro Thr Asp Gly Met Val Cys Ile Asp Gly Gln Asp Ile
445                 450                 455                 460 agg acc ata aat gta agg cat ctt cgg gaa att act ggt gtg gtg agt     1444
Arg Thr Ile Asn Val Arg His Leu Arg Glu Ile Thr Gly Val Val Ser
                    465                 470                 475 cag gag cct gtg ttg ttt gcc acc acg ata gct gaa aac att cgc tat     1492
Gln Glu Pro Val Leu Phe Ala Thr Thr Ile Ala Glu Asn Ile Arg Tyr
                480                 485                 490 ggc cgc gaa aat gtc acc atg gat gag att gag aaa gct gtt aag gaa     1540
Gly Arg Glu Asn Val Thr Met Asp Glu Ile Glu Lys Ala Val Lys Glu
            495                 500                 505 gcc aat gcc tat gat ttt atc atg aaa cta cct aat aaa ttt gac act     1588
Ala Asn Ala Tyr Asp Phe Ile Met Lys Leu Pro Asn Lys Phe Asp Thr
        510                 515                 520 ctg gtt gga gag aga ggg gcc cag ctg agt ggt gga cag aaa cag aga     1636
Leu Val Gly Glu Arg Gly Ala Gln Leu Ser Gly Gly Gln Lys Gln Arg
525                 530                 535                 540 atc gcc att gct cgg gcc ctg gtt cgc aac ccc aag att ctt ctg ctg     1684
Ile Ala Ile Ala Arg Ala Leu Val Arg Asn Pro Lys Ile Leu Leu Leu
                    545                 550                 555 gat gag gca acg tca gct ctg gac act gaa agt gaa gca gtg gtt cag     1732
Asp Glu Ala Thr Ser Ala Leu Asp Thr Glu Ser Glu Ala Val Val Gln
                560                 565                 570 gtg gcc ctg gat aag gcc aga aaa ggc cgg act acc att gtg ata gct     1780
Val Ala Leu Asp Lys Ala Arg Lys Gly Arg Thr Thr Ile Val Ile Ala
            575                 580                 585 cat cgt ttg tct aca gtt cgt aat gcc gat gtc att gct ggt ttt gat     1828
His Arg Leu Ser Thr Val Arg Asn Ala Asp Val Ile Ala Gly Phe Asp
        590                 595                 600 gat gga gtc att gtg gag aaa gga aat cat gat gaa ctc atg aaa gag     1876
Asp Gly Val Ile Val Glu Lys Gly Asn His Asp Glu Leu Met Lys Glu
605                 610                 615                 620 aag ggc att tac ttc aaa ctt gtc aca atg cag aca aga gga aat gaa     1924
Lys Gly Ile Tyr Phe Lys Leu Val Thr Met Gln Thr Arg Gly Asn Glu
                    625                 630                 635 att gag tta gaa aat gcc act ggt gaa tcc aaa agt gaa agt gat gcc     1972
Ile Glu Leu Glu Asn Ala Thr Gly Glu Ser Lys Ser Glu Ser Asp Ala
                640                 645                 650 ttg gaa atg tct cca aaa gat tca ggg tcc agt tta ata aaa aga aga     2020
```

```
                                                        -continued

Leu Glu Met Ser Pro Lys Asp Ser Gly Ser Ser Leu Ile Lys Arg Arg
            655                 660                 665 tca act cgc agg agt ata cat gca cca caa ggc caa gac aga aag ctt    2068
Ser Thr Arg Arg Ser Ile His Ala Pro Gln Gly Gln Asp Arg Lys Leu
        670                 675                 680 ggt aca aaa gag gac ttg aat gag aat gta cct cca gtt tcc ttc tgg    2116
Gly Thr Lys Glu Asp Leu Asn Glu Asn Val Pro Pro Val Ser Phe Trp
685                 690                 695                 700 agg att ctg aag ctg aac tca act gaa tgg cct tat ttt gtg gtt ggt    2164
Arg Ile Leu Lys Leu Asn Ser Thr Glu Trp Pro Tyr Phe Val Val Gly
                705                 710                 715 ata ttt tgt gct att ata aac gga ggc ctg caa cca gca ttt tca ata    2212
Ile Phe Cys Ala Ile Ile Asn Gly Gly Leu Gln Pro Ala Phe Ser Ile
            720                 725                 730 ata ttt tca agg att ata ggg atc ttt acc cga gat gag gat cct gaa    2260
Ile Phe Ser Arg Ile Ile Gly Ile Phe Thr Arg Asp Glu Asp Pro Glu
        735                 740                 745 aca aaa cga cag aat agt aac atg ttt tct gta ttg ttt cta gtc ctt    2308
Thr Lys Arg Gln Asn Ser Asn Met Phe Ser Val Leu Phe Leu Val Leu
    750                 755                 760 gga att att tct ttt att aca ttt ttc ctc cag ggc ttc aca ttt ggc    2356
Gly Ile Ile Ser Phe Ile Thr Phe Phe Leu Gln Gly Phe Thr Phe Gly
765                 770                 775                 780 aaa gct ggg gag atc ctc act aag cgg ctt cga tac atg gtt ttc aga    2404
Lys Ala Gly Glu Ile Leu Thr Lys Arg Leu Arg Tyr Met Val Phe Arg
                785                 790                 795 tcc atg ctg aga cag gat gtc agc tgg ttt gat gac cct aaa aac acc    2452
Ser Met Leu Arg Gln Asp Val Ser Trp Phe Asp Asp Pro Lys Asn Thr
            800                 805                 810 act gga gca ttg aca acc agg ctt gcc aat gat gcg gct caa gtt aaa    2500
Thr Gly Ala Leu Thr Thr Arg Leu Ala Asn Asp Ala Ala Gln Val Lys
        815                 820                 825 ggg gct ata ggt tcc agg ctt gct gtc att acc cag aat ata gca aat    2548
Gly Ala Ile Gly Ser Arg Leu Ala Val Ile Thr Gln Asn Ile Ala Asn
    830                 835                 840 ctt ggg aca ggc att att ata tcc tta atc tat ggt tgg caa tta aca    2596
Leu Gly Thr Gly Ile Ile Ile Ser Leu Ile Tyr Gly Trp Gln Leu Thr
845                 850                 855                 860 ctt tta ctc tta gca att gta ccc atc att gca ata gca gga gtt gtt    2644
Leu Leu Leu Leu Ala Ile Val Pro Ile Ile Ala Ile Ala Gly Val Val
                865                 870                 875 gaa atg aaa atg ttg tct gga caa gca ctg aaa gat aag aaa gag cta    2692
Glu Met Lys Met Leu Ser Gly Gln Ala Leu Lys Asp Lys Lys Glu Leu
            880                 885                 890 gaa gga gct ggg aag att gct aca gaa gcc atc gaa aac ttc cga act    2740
Glu Gly Ala Gly Lys Ile Ala Thr Glu Ala Ile Glu Asn Phe Arg Thr
        895                 900                 905 gtt gtt tct ttg act cgg gag cag aag ttt gaa tac atg tat gca cag    2788
Val Val Ser Leu Thr Arg Glu Gln Lys Phe Glu Tyr Met Tyr Ala Gln
    910                 915                 920 agt ttg caa gta cca tac aga aac tct ttg agg aaa gca cac atc ttc    2836
Ser Leu Gln Val Pro Tyr Arg Asn Ser Leu Arg Lys Ala His Ile Phe
925                 930                 935                 940 ggg gtc tca ttt tct atc acc cag gca atg atg tat ttt tcc tat gct    2884
Gly Val Ser Phe Ser Ile Thr Gln Ala Met Met Tyr Phe Ser Tyr Ala
                945                 950                 955 ggc tgt ttc cgg ttt ggt gcc tac ttg gtg gca aat gag ttc atg aac    2932
Gly Cys Phe Arg Phe Gly Ala Tyr Leu Val Ala Asn Glu Phe Met Asn
            960                 965                 970
```

```
                                                              -continued ttt cag gat gtt ctt ttg gta ttc tca gct att gtc ttt ggt gcc atg    2980
Phe Gln Asp Val Leu Leu Val Phe Ser Ala Ile Val Phe Gly Ala Met
            975                 980                 985 gca gtg ggg cag gtc agt tca ttt gct cct gac tat gcc aaa gcc aaa    3028
Ala Val Gly Gln Val Ser Ser Phe Ala Pro Asp Tyr Ala Lys Ala Lys
        990                 995                1000 gta tca gca gcc cac gtc atc atg atc att gaa aaa agc cct ctg att    3076
Val Ser Ala Ala His Val Ile Met Ile Ile Glu Lys Ser Pro Leu Ile
1005                1010                1015                1020 gac agc tac agc cct cac ggc ctc aag cca aat acg ttg gaa gga aat    3124
Asp Ser Tyr Ser Pro His Gly Leu Lys Pro Asn Thr Leu Glu Gly Asn
                1025                1030                1035 gtg aca ttt aat gag gtc gtg ttc aac tat ccc act cga cca gac atc    3172
Val Thr Phe Asn Glu Val Val Phe Asn Tyr Pro Thr Arg Pro Asp Ile
            1040                1045                1050 ccc gtg ctc cag ggg ctg agc ctc gag gtg aag aag ggc cag acg ctg    3220
Pro Val Leu Gln Gly Leu Ser Leu Glu Val Lys Lys Gly Gln Thr Leu
        1055                1060                1065 gcc ctc gta ggt agc agt ggc tgt ggg aag agc aca gtt gtt cag ctc    3268
Ala Leu Val Gly Ser Ser Gly Cys Gly Lys Ser Thr Val Val Gln Leu
    1070                1075                1080 cta gag cgc ttc tat gac ccc ttg gct ggt tca gtg cta att gat ggc    3316
Leu Glu Arg Phe Tyr Asp Pro Leu Ala Gly Ser Val Leu Ile Asp Gly
1085                1090                1095                1100 aaa gag ata aag cac ctg aat gtc cag tgg ctc cga gca cac ctg ggc    3364
Lys Glu Ile Lys His Leu Asn Val Gln Trp Leu Arg Ala His Leu Gly
                1105                1110                1115 atc gtg tct cag gag ccc atc ctg ttt gac tgc agc att gcc gag aac    3412
Ile Val Ser Gln Glu Pro Ile Leu Phe Asp Cys Ser Ile Ala Glu Asn
            1120                1125                1130 att gcc tat gga gac aac agc cgg gtc gta tca cat gaa gag att atg    3460
Ile Ala Tyr Gly Asp Asn Ser Arg Val Val Ser His Glu Glu Ile Met
        1135                1140                1145 cag gca gcc aag gag gcc aac ata cac cac ttc atc gag aca ctc cct    3508
Gln Ala Ala Lys Glu Ala Asn Ile His His Phe Ile Glu Thr Leu Pro
    1150                1155                1160 gag aaa tac aac acc aga gta gga gac aaa gga acc cag ctc tct ggt    3556
Glu Lys Tyr Asn Thr Arg Val Gly Asp Lys Gly Thr Gln Leu Ser Gly
1165                1170                1175                1180 ggc cag aaa cag cgc att gcc ata gct cgc gct ctt gtt aga cag cct    3604
Gly Gln Lys Gln Arg Ile Ala Ile Ala Arg Ala Leu Val Arg Gln Pro
                1185                1190                1195 cat att ttg ctt ttg gat gaa gct aca tca gct ctg gat aca gaa agt    3652
His Ile Leu Leu Leu Asp Glu Ala Thr Ser Ala Leu Asp Thr Glu Ser
            1200                1205                1210 gaa aag gtt gtc caa gaa gcc ctg gac aaa gcc aga gaa ggc cgc acc    3700
Glu Lys Val Val Gln Glu Ala Leu Asp Lys Ala Arg Glu Gly Arg Thr
        1215                1220                1225 tgc att gtg atc gcc cac cgc ttg tcc acc atc cag aat gca gat tta    3748
Cys Ile Val Ile Ala His Arg Leu Ser Thr Ile Gln Asn Ala Asp Leu
    1230                1235                1240 ata gtg gtg ttt cag aat ggc aaa gtc aag gag cat ggc aca cat caa    3796
Ile Val Val Phe Gln Asn Gly Lys Val Lys Glu His Gly Thr His Gln
1245                1250                1255                1260 cag ctg ctg gcc cag aaa ggc atc tat ttt tcc atg gtc agt gtc cag    3844
Gln Leu Leu Ala Gln Lys Gly Ile Tyr Phe Ser Met Val Ser Val Gln
                1265                1270                1275 gct gga gca aag cgc tagtgaactg tggccatatg agctgttaaa tattttttaa    3899
Ala Gly Ala Lys Arg
            1280
```

-continued

```
tatttgtgtt aaaacatggc atttaatcaa agttaaaagg tgagcactta ctggaaaaac    3959
tatgtagaac tacctgttta acatttcttg ctgcaactga agatcattcc accaagttca    4019
gagtcttcag attttataat taaaggaacc aaaagaaaca ttatctgatg gaataaaata    4079
ctggtgttaa ttgcattata aaattataga gtaattcaaa gtagattttg ttaataaatt    4139
gtataatttt tgtttatatt ttatttgtaa cttactgctt tgctgaaaga ttatagaagt    4199
ggtaaaaagt actgaatgtt tgaataaagt gctagctata ataaaactaa acttttatat    4259
caaaaaaaaa aaaaaaaaaa                                                4279
```

<210> SEQ ID NO 2
<211> LENGTH: 1281
<212> TYPE: PRT
<213> ORGANISM: Canis familiaris

<400> SEQUENCE: 2

```
Met Asp Pro Glu Gly Gly Arg Lys Gly Ser Ala Glu Lys Asn Phe Trp
  1               5                  10                  15

Lys Met Gly Lys Lys Ser Lys Lys Asn Glu Lys Lys Glu Lys Lys Pro
             20                  25                  30

Thr Val Ser Thr Phe Ala Met Phe Arg Tyr Ser Asn Trp Leu Asp Arg
         35                  40                  45

Leu Tyr Met Leu Val Gly Thr Met Ala Ala Ile Ile His Gly Ala Ala
     50                  55                  60

Leu Pro Leu Met Met Leu Val Phe Gly Asn Met Thr Asp Ser Phe Ala
 65                  70                  75                  80

Asn Ala Gly Ile Ser Arg Asn Lys Thr Phe Pro Val Ile Ile Asn Glu
                 85                  90                  95

Ser Ile Thr Asn Asn Thr Gln His Phe Ile Asn His Leu Glu Glu Glu
            100                 105                 110

Met Thr Thr Tyr Ala Tyr Tyr Ser Gly Ile Gly Ala Gly Val Leu
        115                 120                 125

Val Ala Ala Tyr Ile Gln Val Ser Phe Trp Cys Leu Ala Ala Gly Arg
    130                 135                 140

Gln Ile Leu Lys Ile Arg Lys Gln Phe His Ala Ile Met Arg Gln
145                 150                 155                 160

Glu Ile Gly Trp Phe Asp Val His Asp Val Gly Glu Leu Asn Thr Arg
                165                 170                 175

Leu Thr Asp Asp Val Ser Lys Ile Asn Glu Gly Ile Gly Asp Lys Ile
            180                 185                 190

Gly Met Phe Phe His Ser Ile Ala Thr Phe Thr Gly Phe Ile Val
        195                 200                 205

Gly Phe Thr Arg Gly Trp Lys Leu Thr Leu Val Ile Leu Ala Ile Ser
    210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
            260                 265                 270

Lys Lys Glu Leu Glu Arg Tyr Asn Lys Asn Leu Glu Glu Ala Lys Gly
        275                 280                 285

Ile Gly Ile Lys Lys Ala Ile Thr Ala Asn Ile Ser Ile Gly Ala Ala
    290                 295                 300
```

```
Phe Leu Leu Ile Tyr Ala Ser Tyr Ala Leu Ala Phe Trp Tyr Gly Thr
305                 310                 315                 320

Ser Leu Val Leu Ser Ser Glu Tyr Ser Ile Gly Gln Val Leu Thr Val
            325                 330                 335

Phe Phe Ser Val Leu Ile Gly Ala Phe Ser Ile Gly Gln Ala Ser Pro
            340                 345                 350

Ser Ile Glu Ala Phe Ala Asn Ala Arg Gly Ala Ala Tyr Glu Ile Phe
    355                 360                 365

Lys Ile Ile Asp Asn Lys Pro Ser Ile Asp Ser Tyr Ser Lys Ser Gly
370                 375                 380

His Lys Pro Asp Asn Ile Lys Gly Asn Leu Glu Phe Lys Asn Val His
385                 390                 395                 400

Phe Ser Tyr Pro Ser Arg Lys Glu Val Lys Ile Leu Lys Gly Leu Asn
                405                 410                 415

Leu Lys Val Gln Ser Gly Gln Thr Val Ala Leu Val Gly Asn Ser Gly
            420                 425                 430

Cys Gly Lys Ser Thr Thr Val Gln Leu Met Gln Arg Leu Tyr Asp Pro
            435                 440                 445

Thr Asp Gly Met Val Cys Ile Asp Gly Gln Asp Ile Arg Thr Ile Asn
        450                 455                 460

Val Arg His Leu Arg Glu Ile Thr Gly Val Val Ser Gln Glu Pro Val
465                 470                 475                 480

Leu Phe Ala Thr Thr Ile Ala Glu Asn Ile Arg Tyr Gly Arg Glu Asn
                485                 490                 495

Val Thr Met Asp Glu Ile Glu Lys Ala Val Lys Glu Ala Asn Ala Tyr
            500                 505                 510

Asp Phe Ile Met Lys Leu Pro Asn Lys Phe Asp Thr Leu Val Gly Glu
        515                 520                 525

Arg Gly Ala Gln Leu Ser Gly Gly Gln Lys Gln Arg Ile Ala Ile Ala
530                 535                 540

Arg Ala Leu Val Arg Asn Pro Lys Ile Leu Leu Leu Asp Glu Ala Thr
545                 550                 555                 560

Ser Ala Leu Asp Thr Glu Ser Glu Ala Val Val Gln Val Ala Leu Asp
                565                 570                 575

Lys Ala Arg Lys Gly Arg Thr Thr Ile Val Ile Ala His Arg Leu Ser
            580                 585                 590

Thr Val Arg Asn Ala Asp Val Ile Ala Gly Phe Asp Asp Gly Val Ile
        595                 600                 605

Val Glu Lys Gly Asn His Asp Glu Leu Met Lys Glu Lys Gly Ile Tyr
610                 615                 620

Phe Lys Leu Val Thr Met Gln Thr Arg Gly Asn Glu Ile Glu Leu Glu
625                 630                 635                 640

Asn Ala Thr Gly Glu Ser Lys Ser Glu Ser Asp Ala Leu Glu Met Ser
                645                 650                 655

Pro Lys Asp Ser Gly Ser Ser Leu Ile Lys Arg Arg Ser Thr Arg Arg
            660                 665                 670

Ser Ile His Ala Pro Gln Gly Gln Asp Arg Lys Leu Gly Thr Lys Glu
        675                 680                 685

Asp Leu Asn Glu Asn Val Pro Pro Val Ser Phe Trp Arg Ile Leu Lys
    690                 695                 700

Leu Asn Ser Thr Glu Trp Pro Tyr Phe Val Val Gly Ile Phe Cys Ala
705                 710                 715                 720
```

-continued

```
Ile Ile Asn Gly Gly Leu Gln Pro Ala Phe Ser Ile Ile Phe Ser Arg
            725                 730                 735
Ile Ile Gly Ile Phe Thr Arg Asp Glu Asp Pro Glu Thr Lys Arg Gln
        740                 745                 750
Asn Ser Asn Met Phe Ser Val Leu Phe Leu Val Leu Gly Ile Ile Ser
            755                 760                 765
Phe Ile Thr Phe Phe Leu Gln Gly Phe Thr Phe Gly Lys Ala Gly Glu
770                 775                 780
Ile Leu Thr Lys Arg Leu Arg Tyr Met Val Phe Arg Ser Met Leu Arg
785                 790                 795                 800
Gln Asp Val Ser Trp Phe Asp Pro Lys Asn Thr Thr Gly Ala Leu
            805                 810                 815
Thr Thr Arg Leu Ala Asn Asp Ala Ala Gln Val Lys Gly Ala Ile Gly
            820                 825                 830
Ser Arg Leu Ala Val Ile Thr Gln Asn Ile Ala Asn Leu Gly Thr Gly
            835                 840                 845
Ile Ile Ile Ser Leu Ile Tyr Gly Trp Gln Leu Thr Leu Leu Leu Leu
850                 855                 860
Ala Ile Val Pro Ile Ile Ala Ile Ala Gly Val Val Glu Met Lys Met
865                 870                 875                 880
Leu Ser Gly Gln Ala Leu Lys Asp Lys Lys Glu Leu Glu Gly Ala Gly
            885                 890                 895
Lys Ile Ala Thr Glu Ala Ile Glu Asn Phe Arg Thr Val Val Ser Leu
            900                 905                 910
Thr Arg Glu Gln Lys Phe Glu Tyr Met Tyr Ala Gln Ser Leu Gln Val
            915                 920                 925
Pro Tyr Arg Asn Ser Leu Arg Lys Ala His Ile Phe Gly Val Ser Phe
            930                 935                 940
Ser Ile Thr Gln Ala Met Met Tyr Phe Ser Tyr Ala Gly Cys Phe Arg
945                 950                 955                 960
Phe Gly Ala Tyr Leu Val Ala Asn Glu Phe Met Asn Phe Gln Asp Val
            965                 970                 975
Leu Leu Val Phe Ser Ala Ile Val Phe Gly Ala Met Ala Val Gly Gln
            980                 985                 990
Val Ser Ser Phe Ala Pro Asp Tyr Ala Lys Ala Lys Val Ser Ala Ala
            995                 1000                1005
His Val Ile Met Ile Ile Glu Lys Ser Pro Leu Ile Asp Ser Tyr Ser
    1010                1015                1020
Pro His Gly Leu Lys Pro Asn Thr Leu Glu Gly Asn Val Thr Phe Asn
1025                1030                1035                1040
Glu Val Val Phe Asn Tyr Pro Thr Arg Pro Asp Ile Pro Val Leu Gln
                1045                1050                1055
Gly Leu Ser Leu Glu Val Lys Lys Gly Gln Thr Leu Ala Leu Val Gly
                1060                1065                1070
Ser Ser Gly Cys Gly Lys Ser Thr Val Val Gln Leu Leu Glu Arg Phe
        1075                1080                1085
Tyr Asp Pro Leu Ala Gly Ser Val Leu Ile Asp Gly Lys Glu Ile Lys
        1090                1095                1100
His Leu Asn Val Gln Trp Leu Arg Ala His Leu Gly Ile Val Ser Gln
1105                1110                1115                1120
Glu Pro Ile Leu Phe Asp Cys Ser Ile Ala Glu Asn Ile Ala Tyr Gly
            1125                1130                1135
Asp Asn Ser Arg Val Val Ser His Glu Glu Ile Met Gln Ala Ala Lys
```

```
                    1140              1145              1150
Glu Ala Asn Ile His His Phe Ile Glu Thr Leu Pro Glu Lys Tyr Asn
        1155              1160              1165

Thr Arg Val Gly Asp Lys Gly Thr Gln Leu Ser Gly Gly Gln Lys Gln
    1170              1175              1180

Arg Ile Ala Ile Ala Arg Ala Leu Val Arg Gln Pro His Ile Leu Leu
1185              1190              1195              1200

Leu Asp Glu Ala Thr Ser Ala Leu Asp Thr Glu Ser Glu Lys Val Val
                1205              1210              1215

Gln Glu Ala Leu Asp Lys Ala Arg Glu Gly Arg Thr Cys Ile Val Ile
            1220              1225              1230

Ala His Arg Leu Ser Thr Ile Gln Asn Ala Asp Leu Ile Val Val Phe
        1235              1240              1245

Gln Asn Gly Lys Val Lys Glu His Gly Thr His Gln Leu Leu Ala
    1250              1255              1260

Gln Lys Gly Ile Tyr Phe Ser Met Val Ser Val Gln Ala Gly Ala Lys
1265              1270              1275              1280

Arg

<210> SEQ ID NO 3
<211> LENGTH: 4317
<212> TYPE: DNA
<213> ORGANISM: Canis familiaris
<220> FEATURE:
<221> NAME/KEY: CDS
<222> LOCATION: (70)...(3912)

<400> SEQUENCE: 3
ctaagtcgga gtatcttctt cccaaattcc cttctcggtg gaggttgcga aggaaagccc    60 gaggtgacg atg gat cct gaa gga ggc cgt aag ggg agt gca gag aag aac   111
          Met Asp Pro Glu Gly Gly Arg Lys Gly Ser Ala Glu Lys Asn
            1               5                  10 ttc tgg aaa atg ggc aaa aaa agt aaa aaa gag aag aaa gaa aag aaa   159
Phe Trp Lys Met Gly Lys Lys Ser Lys Lys Glu Lys Lys Glu Lys Lys
 15                  20                  25                  30 cca act gtc agc acg ttt gca atg ttt cgc tat tca aat tgg ctt gat   207
Pro Thr Val Ser Thr Phe Ala Met Phe Arg Tyr Ser Asn Trp Leu Asp
                 35                  40                  45 agg ttg tat atg ttg gtg ggg aca atg gct gcc atc atc cat gga gct   255
Arg Leu Tyr Met Leu Val Gly Thr Met Ala Ala Ile Ile His Gly Ala
             50                  55                  60 gca ctc cct ctc atg atg ctg gtt ttt gga aac atg aca gat agc ttt   303
Ala Leu Pro Leu Met Met Leu Val Phe Gly Asn Met Thr Asp Ser Phe
 65                  70                  75 gca aat gca gga att tca aga aac aaa act ttt cca gtt ata att aat   351
Ala Asn Ala Gly Ile Ser Arg Asn Lys Thr Phe Pro Val Ile Ile Asn
         80                  85                  90 gaa agt att acg aac aat aca caa cat ttc atc aac cat ctg gag gag   399
Glu Ser Ile Thr Asn Asn Thr Gln His Phe Ile Asn His Leu Glu Glu
 95                  100                 105                 110 gaa atg acc acg tat gcc tat tat tac agt ggg atc ggt gct ggc gtg   447
Glu Met Thr Thr Tyr Ala Tyr Tyr Tyr Ser Gly Ile Gly Ala Gly Val
                 115                 120                 125 ctg gtg gct gct tac atc cag gtt tca ttc tgg tgc ctg gca gca gga   495
Leu Val Ala Ala Tyr Ile Gln Val Ser Phe Trp Cys Leu Ala Ala Gly
             130                 135                 140 aga cag ata ctc aaa att aga aaa caa ttt ttt cat gct atc atg cga   543
Arg Gln Ile Leu Lys Ile Arg Lys Gln Phe Phe His Ala Ile Met Arg
```

```
                    145                 150                 155
cag gag att ggc tgg ttt gac gtg cat gac gtt ggg gag ctt aac acc         591
Gln Glu Ile Gly Trp Phe Asp Val His Asp Val Gly Glu Leu Asn Thr
            160                 165                 170 cgg ctc aca gac gat gtc tcc aaa atc aat gaa gga att ggc gac aaa         639
Arg Leu Thr Asp Asp Val Ser Lys Ile Asn Glu Gly Ile Gly Asp Lys
175                 180                 185                 190 gtt gga atg ttc ttt caa tca ata gca aca ttt ttc acc ggt ttt ata         687
Val Gly Met Phe Phe Gln Ser Ile Ala Thr Phe Phe Thr Gly Phe Ile
                195                 200                 205 gtg ggg ttt aca cct ggt tgg aag cta acc ctt gtg att ttg gcc atc         735
Val Gly Phe Thr Pro Gly Trp Lys Leu Thr Leu Val Ile Leu Ala Ile
            210                 215                 220 agc cct gtt ctt gga ctt tca gcc gcc atc tgg gca aag ata cta tct         783
Ser Pro Val Leu Gly Leu Ser Ala Ala Ile Trp Ala Lys Ile Leu Ser
        225                 230                 235 tca ttt act gat aaa gaa ctc ttg gcc tat gca aaa gct gga gca gta         831
Ser Phe Thr Asp Lys Glu Leu Leu Ala Tyr Ala Lys Ala Gly Ala Val
    240                 245                 250 gct gaa gaa gtc tta gca gca atc aga act gtg att gcc ttt gga gga         879
Ala Glu Glu Val Leu Ala Ala Ile Arg Thr Val Ile Ala Phe Gly Gly
255                 260                 265                 270 caa aag aaa gaa ctt gaa agg tac aac aaa aat tta gaa gaa gct aaa         927
Gln Lys Lys Glu Leu Glu Arg Tyr Asn Lys Asn Leu Glu Glu Ala Lys
                275                 280                 285 aga att ggg ata aag aaa gct atc acg gcc aac att tct att ggt gcc         975
Arg Ile Gly Ile Lys Lys Ala Ile Thr Ala Asn Ile Ser Ile Gly Ala
            290                 295                 300 gct ttc tta ttg atc tat gca tca tat gct ctg gct ttc tgg tat ggg        1023
Ala Phe Leu Leu Ile Tyr Ala Ser Tyr Ala Leu Ala Phe Trp Tyr Gly
        305                 310                 315 acc tcc ttg gtc ctc tcc agt gaa tat act att gga cag gta ctc act        1071
Thr Ser Leu Val Leu Ser Ser Glu Tyr Thr Ile Gly Gln Val Leu Thr
    320                 325                 330 gtc ttc ttt tct gta tta att ggg gct ttt agt att gga cag gca tcc        1119
Val Phe Phe Ser Val Leu Ile Gly Ala Phe Ser Ile Gly Gln Ala Ser
335                 340                 345                 350 cca agc att gaa gca ttt gca aac gca aga gga gca gct tat gaa atc        1167
Pro Ser Ile Glu Ala Phe Ala Asn Ala Arg Gly Ala Ala Tyr Glu Ile
                355                 360                 365 ttc aag ata att gac aat aaa cca agc att gac agc tat tcg aag agt        1215
Phe Lys Ile Ile Asp Asn Lys Pro Ser Ile Asp Ser Tyr Ser Lys Ser
            370                 375                 380 gga cat aaa cca gat aat att aag gga aat ttg gaa ttc aaa aat gtt        1263
Gly His Lys Pro Asp Asn Ile Lys Gly Asn Leu Glu Phe Lys Asn Val
        385                 390                 395 cac ttc agt tac cct tct cga aaa gaa gtt aag atc tta aag ggt ctc        1311
His Phe Ser Tyr Pro Ser Arg Lys Glu Val Lys Ile Leu Lys Gly Leu
    400                 405                 410 aac ctg aag gtt cag agt ggg cag aca gtg gcg ctg gtt ggg aac agt        1359
Asn Leu Lys Val Gln Ser Gly Gln Thr Val Ala Leu Val Gly Asn Ser
415                 420                 425                 430 ggc tgc ggg aag agc acg acc gtg cag ctg atg cag agg ctc tat gac        1407
Gly Cys Gly Lys Ser Thr Thr Val Gln Leu Met Gln Arg Leu Tyr Asp
                435                 440                 445 ccc aca gat ggc atg gtc tgt att gat gga cag gac att agg acc ata        1455
Pro Thr Asp Gly Met Val Cys Ile Asp Gly Gln Asp Ile Arg Thr Ile
            450                 455                 460 aat gta agg cat ctt cgg gaa att act ggt gtg gtg agt cag gag cct        1503
```

-continued

```
                Asn Val Arg His Leu Arg Glu Ile Thr Gly Val Val Ser Gln Glu Pro
                            465                 470                 475 gtg ttg ttt gcc acc acg ata gct gaa aac att cgc tat ggc cgc gaa        1551
Val Leu Phe Ala Thr Thr Ile Ala Glu Asn Ile Arg Tyr Gly Arg Glu
            480                 485                 490 aat gtc acc atg gat gag att gag aaa gct gtt aag gaa gcc aat gcc        1599
Asn Val Thr Met Asp Glu Ile Glu Lys Ala Val Lys Glu Ala Asn Ala
495                 500                 505                 510 tat gat ttt atc atg aaa cta cct aat aaa ttt gac act ctg gtt gga        1647
Tyr Asp Phe Ile Met Lys Leu Pro Asn Lys Phe Asp Thr Leu Val Gly
                515                 520                 525 gag aga ggg gcc cgg ctg agt ggt gga cag aaa cag aga atc gcc att        1695
Glu Arg Gly Ala Arg Leu Ser Gly Gly Gln Lys Gln Arg Ile Ala Ile
            530                 535                 540 gct cgg gcc ctg gtt cgc aac ccc aag att ctt ctg ctg gat gag gca        1743
Ala Arg Ala Leu Val Arg Asn Pro Lys Ile Leu Leu Leu Asp Glu Ala
            545                 550                 555 acg tca gct ctg gac act gaa agt gaa gca gtg gtt cag gtg gcc ctg        1791
Thr Ser Ala Leu Asp Thr Glu Ser Glu Ala Val Val Gln Val Ala Leu
        560                 565                 570 gat aag gcc aga aaa ggc cgg act acc att gtg ata gct cat cgt ttg        1839
Asp Lys Ala Arg Lys Gly Arg Thr Thr Ile Val Ile Ala His Arg Leu
575                 580                 585                 590 tct aca gtt cgt aat gcc gat gtc att gct ggt ttt gat gat gga gtc        1887
Ser Thr Val Arg Asn Ala Asp Val Ile Ala Gly Phe Asp Asp Gly Val
                595                 600                 605 att gtg gag aaa gga aat cat gat gaa ctc atg aaa gag aag ggc att        1935
Ile Val Glu Lys Gly Asn His Asp Glu Leu Met Lys Glu Lys Gly Ile
            610                 615                 620 tac ttc aaa ctt gtc aca atg cag aca aga gga aat gaa att gag tta        1983
Tyr Phe Lys Leu Val Thr Met Gln Thr Arg Gly Asn Glu Ile Glu Leu
            625                 630                 635 gaa aat gcc act ggt gaa tcc aaa agt gaa agt gat gcc ttg gaa atg        2031
Glu Asn Ala Thr Gly Glu Ser Lys Ser Glu Ser Asp Ala Leu Glu Met
            640                 645                 650 tct cca aaa gat tca ggg tcc agt tta ata aaa aga aga tca act cgc        2079
Ser Pro Lys Asp Ser Gly Ser Ser Leu Ile Lys Arg Arg Ser Thr Arg
655                 660                 665                 670 agg agt ata cat gca cca caa ggc caa gac aga aag ctt ggt aca aaa        2127
Arg Ser Ile His Ala Pro Gln Gly Gln Asp Arg Lys Leu Gly Thr Lys
                675                 680                 685 gag gac ttg aat gag aat gtt cct tca gtt tcc ttc tgg agg att ctg        2175
Glu Asp Leu Asn Glu Asn Val Pro Ser Val Ser Phe Trp Arg Ile Leu
            690                 695                 700 aag ctg aac tca act gaa tgg cct tat ttt gtg gtt ggt ata ttt tgt        2223
Lys Leu Asn Ser Thr Glu Trp Pro Tyr Phe Val Val Gly Ile Phe Cys
            705                 710                 715 gct att ata aac gga ggc ctg caa cca gca ttt tca ata ata ttt tca        2271
Ala Ile Ile Asn Gly Gly Leu Gln Pro Ala Phe Ser Ile Ile Phe Ser
        720                 725                 730 agg att ata ggg atc ttt acc cga gat gag gat cct gaa aca aaa cga        2319
Arg Ile Ile Gly Ile Phe Thr Arg Asp Glu Asp Pro Glu Thr Lys Arg
735                 740                 745                 750 cag aat agt aac atg ttt tct gta ttg ttt cta gtc ctt gga att att        2367
Gln Asn Ser Asn Met Phe Ser Val Leu Phe Leu Val Leu Gly Ile Ile
                755                 760                 765 tct ttt att aca ttt ttc ctc cag ggc ttc aca ttt ggc aaa gct ggg        2415
Ser Phe Ile Thr Phe Phe Leu Gln Gly Phe Thr Phe Gly Lys Ala Gly
            770                 775                 780
```

```
gag atc ctc act aag cgg ctt cga tac atg gtt ttc aga tcc atg ctg      2463
Glu Ile Leu Thr Lys Arg Leu Arg Tyr Met Val Phe Arg Ser Met Leu
        785                 790                 795 aga cag gat gtc agc tgg ttt gat gac cct aaa aac acc act gga gca      2511
Arg Gln Asp Val Ser Trp Phe Asp Asp Pro Lys Asn Thr Thr Gly Ala
800                 805                 810 ttg aca acc agg ctt gcc aat gat gcg gct caa gtt aaa ggg gct ata      2559
Leu Thr Thr Arg Leu Ala Asn Asp Ala Ala Gln Val Lys Gly Ala Ile
815                 820                 825                 830 ggt tcc agg ctt gct gtc att acc cag aat ata gca aat ctt ggg aca      2607
Gly Ser Arg Leu Ala Val Ile Thr Gln Asn Ile Ala Asn Leu Gly Thr
                835                 840                 845 ggc att att ata tcc tta atc tat ggt tgg caa tta aca ctt tta ctc      2655
Gly Ile Ile Ile Ser Leu Ile Tyr Gly Trp Gln Leu Thr Leu Leu Leu
        850                 855                 860 tta gca att gta ccc atc att gca ata gca gga gtt gtt gaa atg aaa      2703
Leu Ala Ile Val Pro Ile Ile Ala Ile Ala Gly Val Val Glu Met Lys
865                 870                 875 atg ttg tct gga caa gca ctg aaa gat aag aaa gag cta gaa gga gct      2751
Met Leu Ser Gly Gln Ala Leu Lys Asp Lys Lys Glu Leu Glu Gly Ala
        880                 885                 890 ggg aag att gct aca gaa gcc atc gaa aac ttc cga act gtt gtt tct      2799
Gly Lys Ile Ala Thr Glu Ala Ile Glu Asn Phe Arg Thr Val Val Ser
895                 900                 905                 910 ttg act cgg gag cag aag ttt gaa tac atg tat gca cag agt ttg caa      2847
Leu Thr Arg Glu Gln Lys Phe Glu Tyr Met Tyr Ala Gln Ser Leu Gln
                915                 920                 925 gta cca tac aga aac tct ttg agg aaa gca cac atc ttc ggg gtc tca      2895
Val Pro Tyr Arg Asn Ser Leu Arg Lys Ala His Ile Phe Gly Val Ser
        930                 935                 940 ttt tct atc acc cag gca atg atg tat ttt tcc tat gct ggc tgt ttc      2943
Phe Ser Ile Thr Gln Ala Met Met Tyr Phe Ser Tyr Ala Gly Cys Phe
945                 950                 955 cgg ttt ggt gcc tac ttg gtg gca aat gag ttc atg aac ttt cag gat      2991
Arg Phe Gly Ala Tyr Leu Val Ala Asn Glu Phe Met Asn Phe Gln Asp
        960                 965                 970 gtt ctt ttg gta ttc tca gct att gtc ttt ggt gcc atg gca gtg ggg      3039
Val Leu Leu Val Phe Ser Ala Ile Val Phe Gly Ala Met Ala Val Gly
975                 980                 985                 990 cag gtc agt tca ttt gct cct gac tat gcc aaa gcc aaa gta tca gca      3087
Gln Val Ser Ser Phe Ala Pro Asp Tyr Ala Lys Ala Lys Val Ser Ala
                995                 1000                1005 gcc cac gtc atc atg atc att gaa aaa agc cct ctg att gac agc tac      3135
Ala His Val Ile Met Ile Ile Glu Lys Ser Pro Leu Ile Asp Ser Tyr
        1010                1015                1020 agc cct cac ggc ctc aag cca aat acg ttg gaa gga aat gtg aca ttt      3183
Ser Pro His Gly Leu Lys Pro Asn Thr Leu Glu Gly Asn Val Thr Phe
1025                1030                1035 aat gag gtc gtg ttc aac tat ccc act cga cca gac atc ccc gtg ctc      3231
Asn Glu Val Val Phe Asn Tyr Pro Thr Arg Pro Asp Ile Pro Val Leu
        1040                1045                1050 cag ggg ctg agc ctc gag gtg aag aag ggc cag acg ctg gcc ctc gta      3279
Gln Gly Leu Ser Leu Glu Val Lys Lys Gly Gln Thr Leu Ala Leu Val
1055                1060                1065                1070 ggt agc agt ggc tgt ggg aag agc aca gtt gtt cag ctc cta gag cgc      3327
Gly Ser Ser Gly Cys Gly Lys Ser Thr Val Val Gln Leu Leu Glu Arg
                1075                1080                1085 ttc tat gac ccc ttg gct ggt tca gtg cta att gat ggc aaa gag ata      3375
Phe Tyr Asp Pro Leu Ala Gly Ser Val Leu Ile Asp Gly Lys Glu Ile
        1090                1095                1100
```

-continued

```
aag cac ctg aat gtc cag tgg ctc cga gca cac ctg ggc atc gtg tct        3423
Lys His Leu Asn Val Gln Trp Leu Arg Ala His Leu Gly Ile Val Ser
        1105                1110                1115 cag gag ccc atc ctg ttt gac tgc agc att gcc gag aac att gcc tat        3471
Gln Glu Pro Ile Leu Phe Asp Cys Ser Ile Ala Glu Asn Ile Ala Tyr
    1120                1125                1130 gga gac aac agc cgg gtc gta tca cat gaa gag att atg cag gca gcc        3519
Gly Asp Asn Ser Arg Val Val Ser His Glu Glu Ile Met Gln Ala Ala
1135                1140                1145                1150 aag gag gcc aac ata cac cac ttc atc gag aca ctc cct gag aaa tac        3567
Lys Glu Ala Asn Ile His His Phe Ile Glu Thr Leu Pro Glu Lys Tyr
            1155                1160                1165 aac acc aga gta gga gac aaa gga acc cag ctc tct ggt ggc cag aaa        3615
Asn Thr Arg Val Gly Asp Lys Gly Thr Gln Leu Ser Gly Gly Gln Lys
        1170                1175                1180 cag cgc att gcc ata gct cgc gct ctt gtt aga cag cct cat att ttg        3663
Gln Arg Ile Ala Ile Ala Arg Ala Leu Val Arg Gln Pro His Ile Leu
    1185                1190                1195 ctt ttg gat gaa gct aca tca gct ctg gat aca gaa agt gaa aag gtt        3711
Leu Leu Asp Glu Ala Thr Ser Ala Leu Asp Thr Glu Ser Glu Lys Val
1200                1205                1210 gtc caa gaa gcc ctg gac aaa gcc aga gaa ggc cgc acc tgc att gtg        3759
Val Gln Glu Ala Leu Asp Lys Ala Arg Glu Gly Arg Thr Cys Ile Val
1215                1220                1225                1230 atc gcc cac cgc ttg tcc acc atc cag aat gca gat tta ata gtg gtg        3807
Ile Ala His Arg Leu Ser Thr Ile Gln Asn Ala Asp Leu Ile Val Val
            1235                1240                1245 ttt cag aat ggc aaa gtc aag gag cat ggc aca cat caa cag ctg ctg        3855
Phe Gln Asn Gly Lys Val Lys Glu His Gly Thr His Gln Gln Leu Leu
        1250                1255                1260 gct cag aaa ggc atc tat ttt tcc atg atc agt gtc cag gct gga gca        3903
Ala Gln Lys Gly Ile Tyr Phe Ser Met Ile Ser Val Gln Ala Gly Ala
    1265                1270                1275 aag cgc tag tgaactgtgg ccatatgagc tgttaaatat ttttaatat                 3952
Lys Arg
    1280 ttgtgttaaa acatggcatt taatcaaagt taaaggtga gcacttactg gaaaaactat      4012 gtagaactac ctgtttaaca tttcttgctg caactgaaga tcattccacc aagttcagag      4072 tcttcagatt ttataattaa aggaaccaaa agaaacatta tctgatggaa taaaatattg      4132 gtgttaattg cattataaaa ttatagagta attcaaagta gattttgtta ataaattgta      4192 taatttttgt ttatatttta tttgtaactt actgctttgc tgaaagatta tagaagtggt      4252 aaaaagtact gaatgtttga ataaagtgct agctataata aaactaaact tttatatgaa      4312 aaaaa                                                                   4317

<210> SEQ ID NO 4
<211> LENGTH: 1280
<212> TYPE: PRT
<213> ORGANISM: Canis familiaris

<400> SEQUENCE: 4

Met Asp Pro Glu Gly Gly Arg Lys Gly Ser Ala Glu Lys Asn Phe Trp
 1               5                  10                  15

Lys Met Gly Lys Lys Ser Lys Lys Glu Lys Lys Glu Lys Lys Pro Thr
            20                  25                  30

Val Ser Thr Phe Ala Met Phe Arg Tyr Ser Asn Trp Leu Asp Arg Leu
        35                  40                  45
```

```
Tyr Met Leu Val Gly Thr Met Ala Ala Ile Ile His Gly Ala Ala Leu
         50                  55                  60

Pro Leu Met Met Leu Val Phe Gly Asn Met Thr Asp Ser Phe Ala Asn
 65                  70                  75                  80

Ala Gly Ile Ser Arg Asn Lys Thr Phe Pro Val Ile Ile Asn Glu Ser
                 85                  90                  95

Ile Thr Asn Asn Thr Gln His Phe Ile Asn His Leu Glu Glu Glu Met
                100                 105                 110

Thr Thr Tyr Ala Tyr Tyr Ser Gly Ile Gly Ala Gly Val Leu Val
            115                 120                 125

Ala Ala Tyr Ile Gln Val Ser Phe Trp Cys Leu Ala Ala Gly Arg Gln
130                 135                 140

Ile Leu Lys Ile Arg Lys Gln Phe Phe His Ala Ile Met Arg Gln Glu
145                 150                 155                 160

Ile Gly Trp Phe Asp Val His Asp Val Gly Glu Leu Asn Thr Arg Leu
                165                 170                 175

Thr Asp Asp Val Ser Lys Ile Asn Glu Gly Ile Gly Asp Lys Val Gly
                180                 185                 190

Met Phe Phe Gln Ser Ile Ala Thr Phe Phe Thr Gly Phe Ile Val Gly
        195                 200                 205

Phe Thr Pro Gly Trp Lys Leu Thr Leu Val Ile Leu Ala Ile Ser Pro
    210                 215                 220

Val Leu Gly Leu Ser Ala Ala Ile Trp Ala Lys Ile Leu Ser Ser Phe
225                 230                 235                 240

Thr Asp Lys Glu Leu Leu Ala Tyr Ala Lys Ala Gly Ala Val Ala Glu
                245                 250                 255

Glu Val Leu Ala Ala Ile Arg Thr Val Ile Ala Phe Gly Gly Gln Lys
                260                 265                 270

Lys Glu Leu Glu Arg Tyr Asn Lys Asn Leu Glu Glu Ala Lys Arg Ile
            275                 280                 285

Gly Ile Lys Lys Ala Ile Thr Ala Asn Ile Ser Ile Gly Ala Ala Phe
290                 295                 300

Leu Leu Ile Tyr Ala Ser Tyr Ala Leu Ala Phe Trp Tyr Gly Thr Ser
305                 310                 315                 320

Leu Val Leu Ser Ser Glu Tyr Thr Ile Gly Gln Val Leu Thr Val Phe
                325                 330                 335

Phe Ser Val Leu Ile Gly Ala Phe Ser Ile Gly Gln Ala Ser Pro Ser
                340                 345                 350

Ile Glu Ala Phe Ala Asn Ala Arg Gly Ala Ala Tyr Glu Ile Phe Lys
            355                 360                 365

Ile Ile Asp Asn Lys Pro Ser Ile Asp Ser Tyr Ser Lys Ser Gly His
370                 375                 380

Lys Pro Asp Asn Ile Lys Gly Asn Leu Glu Phe Lys Asn Val His Phe
385                 390                 395                 400

Ser Tyr Pro Ser Arg Lys Glu Val Lys Ile Leu Lys Gly Leu Asn Leu
                405                 410                 415

Lys Val Gln Ser Gly Gln Thr Val Ala Leu Val Gly Asn Ser Gly Cys
            420                 425                 430

Gly Lys Ser Thr Thr Val Gln Leu Met Gln Arg Leu Tyr Asp Pro Thr
            435                 440                 445

Asp Gly Met Val Cys Ile Asp Gly Gln Asp Ile Arg Thr Ile Asn Val
450                 455                 460
```

```
Arg His Leu Arg Glu Ile Thr Gly Val Val Ser Gln Glu Pro Val Leu
465                 470                 475                 480

Phe Ala Thr Thr Ile Ala Glu Asn Ile Arg Tyr Gly Arg Glu Asn Val
                485                 490                 495

Thr Met Asp Glu Ile Glu Lys Ala Val Lys Glu Ala Asn Ala Tyr Asp
            500                 505                 510

Phe Ile Met Lys Leu Pro Asn Lys Phe Asp Thr Leu Val Gly Glu Arg
            515                 520                 525

Gly Ala Arg Leu Ser Gly Gln Lys Gln Arg Ile Ala Ile Ala Arg
530                 535                 540

Ala Leu Val Arg Asn Pro Lys Ile Leu Leu Leu Asp Glu Ala Thr Ser
545                 550                 555                 560

Ala Leu Asp Thr Glu Ser Glu Ala Val Val Gln Val Ala Leu Asp Lys
            565                 570                 575

Ala Arg Lys Gly Arg Thr Thr Ile Val Ile Ala His Arg Leu Ser Thr
            580                 585                 590

Val Arg Asn Ala Asp Val Ile Ala Gly Phe Asp Asp Gly Val Ile Val
            595                 600                 605

Glu Lys Gly Asn His Asp Glu Leu Met Lys Glu Lys Gly Ile Tyr Phe
610                 615                 620

Lys Leu Val Thr Met Gln Thr Arg Gly Asn Glu Ile Glu Leu Glu Asn
625                 630                 635                 640

Ala Thr Gly Glu Ser Lys Ser Glu Ser Asp Ala Leu Glu Met Ser Pro
            645                 650                 655

Lys Asp Ser Gly Ser Ser Leu Ile Lys Arg Arg Ser Thr Arg Arg Ser
            660                 665                 670

Ile His Ala Pro Gln Gly Gln Asp Arg Lys Leu Gly Thr Lys Glu Asp
        675                 680                 685

Leu Asn Glu Asn Val Pro Ser Val Ser Phe Trp Arg Ile Leu Lys Leu
690                 695                 700

Asn Ser Thr Glu Trp Pro Tyr Phe Val Val Gly Ile Phe Cys Ala Ile
705                 710                 715                 720

Ile Asn Gly Gly Leu Gln Pro Ala Phe Ser Ile Ile Phe Ser Arg Ile
                725                 730                 735

Ile Gly Ile Phe Thr Arg Asp Glu Asp Pro Glu Thr Lys Arg Gln Asn
            740                 745                 750

Ser Asn Met Phe Ser Val Leu Phe Leu Val Leu Gly Ile Ile Ser Phe
        755                 760                 765

Ile Thr Phe Phe Leu Gln Gly Phe Thr Phe Gly Lys Ala Gly Glu Ile
        770                 775                 780

Leu Thr Lys Arg Leu Arg Tyr Met Val Phe Arg Ser Met Leu Arg Gln
785                 790                 795                 800

Asp Val Ser Trp Phe Asp Asp Pro Lys Asn Thr Thr Gly Ala Leu Thr
            805                 810                 815

Thr Arg Leu Ala Asn Asp Ala Ala Gln Val Lys Gly Ala Ile Gly Ser
            820                 825                 830

Arg Leu Ala Val Ile Thr Gln Asn Ile Ala Asn Leu Gly Thr Gly Ile
        835                 840                 845

Ile Ile Ser Leu Ile Tyr Gly Trp Gln Leu Thr Leu Leu Leu Leu Ala
        850                 855                 860

Ile Val Pro Ile Ile Ala Ile Ala Gly Val Val Glu Met Lys Met Leu
865                 870                 875                 880

Ser Gly Gln Ala Leu Lys Asp Lys Lys Glu Leu Glu Gly Ala Gly Lys
```

-continued

```
                885                 890                 895
Ile Ala Thr Glu Ala Ile Glu Asn Phe Arg Thr Val Val Ser Leu Thr
            900                 905                 910

Arg Glu Gln Lys Phe Glu Tyr Met Tyr Ala Gln Ser Leu Gln Val Pro
        915                 920                 925

Tyr Arg Asn Ser Leu Arg Lys Ala His Ile Phe Gly Val Ser Phe Ser
    930                 935                 940

Ile Thr Gln Ala Met Met Tyr Phe Ser Tyr Ala Gly Cys Phe Arg Phe
945                 950                 955                 960

Gly Ala Tyr Leu Val Ala Asn Glu Phe Met Asn Phe Gln Asp Val Leu
                965                 970                 975

Leu Val Phe Ser Ala Ile Val Phe Gly Ala Met Ala Val Gly Gln Val
            980                 985                 990

Ser Ser Phe Ala Pro Asp Tyr Ala Lys Ala Lys Val Ser Ala Ala His
        995                 1000                1005

Val Ile Met Ile Ile Glu Lys Ser Pro Leu Ile Asp Ser Tyr Ser Pro
    1010                1015                1020

His Gly Leu Lys Pro Asn Thr Leu Glu Gly Asn Val Thr Phe Asn Glu
1025                1030                1035                1040

Val Val Phe Asn Tyr Pro Thr Arg Pro Asp Ile Pro Val Leu Gln Gly
                1045                1050                1055

Leu Ser Leu Glu Val Lys Lys Gly Gln Thr Leu Ala Leu Val Gly Ser
            1060                1065                1070

Ser Gly Cys Gly Lys Ser Thr Val Val Gln Leu Leu Glu Arg Phe Tyr
        1075                1080                1085

Asp Pro Leu Ala Gly Ser Val Leu Ile Asp Gly Lys Glu Ile Lys His
    1090                1095                1100

Leu Asn Val Gln Trp Leu Arg Ala His Leu Gly Ile Val Ser Gln Glu
1105                1110                1115                1120

Pro Ile Leu Phe Asp Cys Ser Ile Ala Glu Asn Ile Ala Tyr Gly Asp
                1125                1130                1135

Asn Ser Arg Val Val Ser His Glu Glu Ile Met Gln Ala Ala Lys Glu
            1140                1145                1150

Ala Asn Ile His His Phe Ile Glu Thr Leu Pro Glu Lys Tyr Asn Thr
        1155                1160                1165

Arg Val Gly Asp Lys Gly Thr Gln Leu Ser Gly Gly Gln Lys Gln Arg
    1170                1175                1180

Ile Ala Ile Ala Arg Ala Leu Val Arg Gln Pro His Ile Leu Leu Leu
1185                1190                1195                1200

Asp Glu Ala Thr Ser Ala Leu Asp Thr Glu Ser Glu Lys Val Val Gln
                1205                1210                1215

Glu Ala Leu Asp Lys Ala Arg Glu Gly Arg Thr Cys Ile Val Ile Ala
            1220                1225                1230

His Arg Leu Ser Thr Ile Gln Asn Ala Asp Leu Ile Val Val Phe Gln
        1235                1240                1245

Asn Gly Lys Val Lys Glu His Gly Thr His Gln Gln Leu Leu Ala Gln
    1250                1255                1260

Lys Gly Ile Tyr Phe Ser Met Ile Ser Val Gln Ala Gly Ala Lys Arg
1265                1270                1275                1280
```

<210> SEQ ID NO 5
<211> LENGTH: 1107
<212> TYPE: DNA
<213> ORGANISM: Canis familiaris

```
<220> FEATURE:
<221> NAME/KEY: CDS
<222> LOCATION: (1)...(1107)

<400> SEQUENCE: 5 acg tca gct ctg gac act gaa agt gaa gca gtg gtt cag gtg gcc ctg      48
Thr Ser Ala Leu Asp Thr Glu Ser Glu Ala Val Val Gln Val Ala Leu
 1               5                  10                  15 gat aag gcc aga aaa ggc cgg act acc att gtg ata gct cat cgt ttg      96
Asp Lys Ala Arg Lys Gly Arg Thr Thr Ile Val Ile Ala His Arg Leu
                 20                  25                  30 tct aca gtt cgt aat gcc gat gtc att gct ggt ttt gat gat gga gtc     144
Ser Thr Val Arg Asn Ala Asp Val Ile Ala Gly Phe Asp Asp Gly Val
             35                  40                  45 att gtg gag aaa gga aat cat gat gaa ctc atg aaa gag aaa ggc att     192
Ile Val Glu Lys Gly Asn His Asp Glu Leu Met Lys Glu Lys Gly Ile
 50                  55                  60 tac ttc aaa ctt gtc aca atg cag aca aga gga aat gaa att gac tta     240
Tyr Phe Lys Leu Val Thr Met Gln Thr Arg Gly Asn Glu Ile Asp Leu
 65                  70                  75                  80 gaa aat gcc act ggt gaa tcc aaa agt gaa agt gat gcc ttg gaa atg     288
Glu Asn Ala Thr Gly Glu Ser Lys Ser Glu Ser Asp Ala Leu Glu Met
                 85                  90                  95 tct cca aaa gat tca ggg tcc agt tta ata aaa aga aga tca act cgc     336
Ser Pro Lys Asp Ser Gly Ser Ser Leu Ile Lys Arg Arg Ser Thr Arg
                100                 105                 110 agg agt ata cat gca cca caa ggc caa gac aga aag ctt ggt aca aaa     384
Arg Ser Ile His Ala Pro Gln Gly Gln Asp Arg Lys Leu Gly Thr Lys
            115                 120                 125 gag gac ttg aat gag aat gta cct cca gtt tcc ttc tgg agg att ctg     432
Glu Asp Leu Asn Glu Asn Val Pro Pro Val Ser Phe Trp Arg Ile Leu
130                 135                 140 aag ctg aac tca act gaa tgg cct tat ttt gtg gtt ggt ata ttt tgt     480
Lys Leu Asn Ser Thr Glu Trp Pro Tyr Phe Val Val Gly Ile Phe Cys
145                 150                 155                 160 gct att ata aac gga ggc ctg cag cca gca ttt tca ata ata ttt tca     528
Ala Ile Ile Asn Gly Gly Leu Gln Pro Ala Phe Ser Ile Ile Phe Ser
                165                 170                 175 agg att ata ggg atc ttt acc cga gat gag gat cct gaa aca aaa cga     576
Arg Ile Ile Gly Ile Phe Thr Arg Asp Glu Asp Pro Glu Thr Lys Arg
                180                 185                 190 cag att agt aac atg ttt tct gta ttg ttt cta gtc ctt gga att att     624
Gln Ile Ser Asn Met Phe Ser Val Leu Phe Leu Val Leu Gly Ile Ile
            195                 200                 205 tct ttt att aca ttt ttc ctt cag ggt ttc aca ttt ggc aaa gct gga     672
Ser Phe Ile Thr Phe Phe Leu Gln Gly Phe Thr Phe Gly Lys Ala Gly
210                 215                 220 gag atc ctc act aag cgg ctt cga tac atg gtt ttc aga tcc atg ctg     720
Glu Ile Leu Thr Lys Arg Leu Arg Tyr Met Val Phe Arg Ser Met Leu
225                 230                 235                 240 aga cag gat gtc agc tgg ttt gat gac ctt aaa aac acc act gga gca     768
Arg Gln Asp Val Ser Trp Phe Asp Asp Leu Lys Asn Thr Thr Gly Ala
                245                 250                 255 ttg acc acc agg ctt gcc aat gat gct gct caa gtt aaa ggg gct ata     816
Leu Thr Thr Arg Leu Ala Asn Asp Ala Ala Gln Val Lys Gly Ala Ile
                260                 265                 270 ggt tcc agg ctt gct gtc att acc cag aat ata gca aat ctt ggg aca     864
Gly Ser Arg Leu Ala Val Ile Thr Gln Asn Ile Ala Asn Leu Gly Thr
            275                 280                 285 ggc att att ata tcc tta atc tat ggt tgg caa tta aca ctt tta ctc     912
```

```
Gly Ile Ile Ile Ser Leu Ile Tyr Gly Trp Gln Leu Thr Leu Leu Leu
    290                 295                 300 tta gca att gta ccc atc att gca ata gca gga gtt gtt gaa atg aaa      960
Leu Ala Ile Val Pro Ile Ile Ala Ile Ala Gly Val Val Glu Met Lys
305                 310                 315                 320 atg ttg tct gga caa gca ctg aaa gat aag aaa gag cta gaa gga gct     1008
Met Leu Ser Gly Gln Ala Leu Lys Asp Lys Lys Glu Leu Glu Gly Ala
                325                 330                 335 ggg aag att gct aca gaa gcc atc gaa aac ttc cga act gtt gtt tct     1056
Gly Lys Ile Ala Thr Glu Ala Ile Glu Asn Phe Arg Thr Val Val Ser
            340                 345                 350 ttg act cag gag cag aag ttt gaa cac atg tat gca cag agt ttg cag     1104
Leu Thr Gln Glu Gln Lys Phe Glu His Met Tyr Ala Gln Ser Leu Gln
        355                 360                 365 gta                                                                  1107
```

<210> SEQ ID NO 6
<211> LENGTH: 368
<212> TYPE: PRT
<213> ORGANISM: Canis familiaris

<400> SEQUENCE: 6

```
Thr Ser Ala Leu Asp Thr Glu Ser Glu Ala Val Val Gln Val Ala Leu
  1               5                  10                  15

Asp Lys Ala Arg Lys Gly Arg Thr Thr Ile Val Ile Ala His Arg Leu
             20                  25                  30

Ser Thr Val Arg Asn Ala Asp Val Ile Ala Gly Phe Asp Asp Gly Val
         35                  40                  45

Ile Val Glu Lys Gly Asn His Asp Glu Leu Met Lys Glu Lys Gly Ile
 50                  55                  60

Tyr Phe Lys Leu Val Thr Met Gln Thr Arg Gly Asn Glu Ile Asp Leu
 65                  70                  75                  80

Glu Asn Ala Thr Gly Glu Ser Lys Ser Glu Ser Asp Ala Leu Glu Met
                 85                  90                  95

Ser Pro Lys Asp Ser Gly Ser Ser Leu Ile Lys Arg Arg Ser Thr Arg
            100                 105                 110

Arg Ser Ile His Ala Pro Gln Gly Gln Asp Arg Lys Leu Gly Thr Lys
        115                 120                 125

Glu Asp Leu Asn Glu Asn Val Pro Pro Val Ser Phe Trp Arg Ile Leu
    130                 135                 140

Lys Leu Asn Ser Thr Glu Trp Pro Tyr Phe Val Val Gly Ile Phe Cys
145                 150                 155                 160

Ala Ile Ile Asn Gly Gly Leu Gln Pro Ala Phe Ser Ile Ile Phe Ser
                165                 170                 175

Arg Ile Ile Gly Ile Phe Thr Arg Asp Glu Asp Pro Glu Thr Lys Arg
            180                 185                 190

Gln Ile Ser Asn Met Phe Ser Val Leu Phe Leu Val Leu Gly Ile Ile
        195                 200                 205

Ser Phe Ile Thr Phe Phe Leu Gln Gly Phe Thr Phe Gly Lys Ala Gly
    210                 215                 220

Glu Ile Leu Thr Lys Arg Leu Arg Tyr Met Val Phe Arg Ser Met Leu
225                 230                 235                 240

Arg Gln Asp Val Ser Trp Phe Asp Asp Leu Lys Asn Thr Thr Gly Ala
                245                 250                 255

Leu Thr Thr Arg Leu Ala Asn Asp Ala Ala Gln Val Lys Gly Ala Ile
            260                 265                 270
```

-continued

```
Gly Ser Arg Leu Ala Val Ile Thr Gln Asn Ile Ala Asn Leu Gly Thr
        275                 280                 285

Gly Ile Ile Ile Ser Leu Ile Tyr Gly Trp Gln Leu Thr Leu Leu
        290                 295                 300

Leu Ala Ile Val Pro Ile Ile Ala Ile Ala Gly Val Val Glu Met Lys
305                 310                 315                 320

Met Leu Ser Gly Gln Ala Leu Lys Asp Lys Lys Glu Leu Glu Gly Ala
                325                 330                 335

Gly Lys Ile Ala Thr Glu Ala Ile Glu Asn Phe Arg Thr Val Val Ser
                340                 345                 350

Leu Thr Gln Glu Gln Lys Phe Glu His Met Tyr Ala Gln Ser Leu Gln
                355                 360                 365

<210> SEQ ID NO 7
<211> LENGTH: 1280
<212> TYPE: PRT
<213> ORGANISM: Homo sapiens

<400> SEQUENCE: 7

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
```

-continued

```
                275                 280                 285
Ile Lys Lys Ala Ile Thr Ala Asn Ile Ser Ile Gly Ala Ala Phe Leu
            290                 295                 300
Leu Ile Tyr Ala Ser Tyr Ala Leu Ala Phe Trp Tyr Gly Thr Thr Leu
305                 310                 315                 320
Val Leu Ser Gly Glu Tyr Ser Ile Gly Gln Val Leu Thr Val Phe Phe
                325                 330                 335
Ser Val Leu Ile Gly Ala Phe Ser Val Gly Gln Ala Ser Pro Ser Ile
            340                 345                 350
Glu Ala Phe Ala Asn Ala Arg Gly Ala Ala Tyr Glu Ile Phe Lys Ile
                355                 360                 365
Ile Asp Asn Lys Pro Ser Ile Asp Ser Tyr Ser Lys Ser Gly His Lys
370                 375                 380
Pro Asp Asn Ile Lys Gly Asn Leu Glu Phe Arg Asn Val His Phe Ser
385                 390                 395                 400
Tyr Pro Ser Arg Lys Glu Val Lys Ile Leu Lys Gly Leu Asn Leu Lys
                405                 410                 415
Val Gln Ser Gly Gln Thr Val Ala Leu Val Gly Asn Ser Gly Cys Gly
            420                 425                 430
Lys Ser Thr Thr Val Gln Leu Met Gln Arg Leu Tyr Asp Pro Thr Glu
            435                 440                 445
Gly Met Val Ser Val Asp Gly Gln Asp Ile Arg Thr Ile Asn Val Arg
            450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
Met Asp Glu Ile Glu Lys Ala Val Lys Glu Ala Asn Ala Tyr Asp Phe
            500                 505                 510
Ile Met Lys Leu Pro His Lys Phe Asp Thr Leu Val Gly Glu Arg Gly
            515                 520                 525
Ala Gln Leu Ser Gly Gly Gln Lys Gln Arg Ile Ala Ile Ala Arg Ala
530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
            580                 585                 590
Arg Asn Ala Asp Val Ile Ala Gly Phe Asp Asp Gly Val Ile Val Glu
            595                 600                 605
Lys Gly Asn His Asp Glu Leu Met Lys Glu Lys Gly Ile Tyr Phe Lys
610                 615                 620
Leu Val Thr Met Gln Thr Ala Gly Asn Glu Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
            660                 665                 670
Arg Gly Ser Gln Ala Gln Asp Arg Lys Leu Ser Thr Lys Glu Ala Leu
            675                 680                 685
Asp Glu Ser Ile Pro Pro Val Ser Phe Trp Arg Ile Met Lys Leu Asn
            690                 695                 700
```

-continued

```
Leu Thr Glu Trp Pro Tyr Phe Val Gly Val Phe Cys Ala Ile Ile
705                 710                 715                 720

Asn Gly Gly Leu Gln Pro Ala Phe Ala Ile Ile Phe Ser Lys Ile Ile
            725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
                835                 840                 845

Ile Ser Phe Ile Tyr Gly Trp Gln Leu Thr Leu Leu Leu Leu Ala Ile
850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
            965                 970                 975

Val Phe Ser Ala Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu
        1090                1095                1100

Asn Val Gln Trp Leu Arg Ala His Leu Gly Ile Val Ser Gln Glu Pro
1105                1110                1115                1120
```

-continued

```
Ile Leu Phe Asp Cys Ser Ile Ala Glu Asn Ile Ala Tyr Gly Asp Asn
            1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
            1155                1160                1165

Val Gly Asp Lys Gly Thr Gln Leu Ser Gly Gln Lys Gln Arg Ile
            1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
            1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
            1250                1255                1260

Gly Ile Tyr Phe Ser Met Val Ser Val Gln Ala Gly Thr Lys Arg Gln
1265                1270                1275                1280

<210> SEQ ID NO 8
<211> LENGTH: 1279
<212> TYPE: PRT
<213> ORGANISM: Homo sapiens

<400> SEQUENCE: 8

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile His Gly Ala Gly
50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
            85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
            165                 170                 175

Asp Asp Val Ser Lys Ile Asn Glu Gly Ile Gly Asp Lys Ile Gly Met
            180                 185                 190

Phe Phe Gln Ser Met Ala Thr Phe Thr Gly Phe Ile Val Gly Phe
            195                 200                 205

Thr Arg Gly Trp Lys Leu Thr Leu Val Ile Leu Ala Ile Ser Pro Val
210                 215                 220
```

-continued

```
Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
            245                 250                 255

Val Leu Ala Ala Ile Arg Thr Val Ile Ala Phe Gly Gly Gln Lys Lys
        260                 265                 270

Glu Leu Glu Arg Tyr Asn Lys Asn Leu Glu Glu Ala Lys Arg Ile Gly
    275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Ser
            325                 330                 335

Val Leu Ile Gly Ala Phe Ser Val Gly Gln Ala Ser Pro Ser Ile Glu
        340                 345                 350

Ala Phe Ala Asn Ala Arg Gly Ala Ala Tyr Glu Ile Phe Lys Ile Ile
    355                 360                 365

Asp Asn Lys Pro Ser Ile Asp Ser Tyr Ser Lys Ser Gly His Lys Pro
370                 375                 380

Asp Asn Ile Lys Gly Asn Leu Glu Phe Arg Asn Val His Phe Ser Tyr
385                 390                 395                 400

Pro Ser Arg Lys Glu Val Lys Ile Leu Lys Gly Leu Asn Leu Lys Val
            405                 410                 415

Gln Ser Gly Gln Thr Val Ala Leu Val Gly Asn Ser Gly Cys Gly Lys
        420                 425                 430

Ser Thr Thr Val Gln Leu Met Gln Arg Leu Tyr Asp Pro Thr Glu Gly
    435                 440                 445

Met Val Ser Val Asp Gly Gln Asp Ile Arg Thr Ile Asn Val Arg Phe
450                 455                 460

Leu Arg Glu Ile Ile Gly Val Val Ser Gln Glu Pro Val Leu Phe Ala
465                 470                 475                 480

Thr Thr Ile Ala Glu Asn Ile Arg Tyr Gly Arg Glu Asn Val Thr Met
            485                 490                 495

Asp Glu Ile Glu Lys Ala Val Lys Glu Ala Asn Ala Tyr Asp Phe Ile
        500                 505                 510

Met Lys Leu Pro His Lys Phe Asp Thr Leu Val Gly Glu Arg Gly Ala
    515                 520                 525

Gln Leu Ser Gly Gly Gln Lys Gln Arg Ile Ala Ile Ala Arg Ala Leu
530                 535                 540

Val Arg Asn Pro Lys Ile Leu Leu Leu Asp Glu Ala Thr Ser Ala Leu
545                 550                 555                 560

Asp Thr Glu Ser Glu Ala Val Val Gln Val Ala Leu Asp Lys Ala Arg
            565                 570                 575

Lys Gly Arg Thr Thr Ile Val Ile Ala His Arg Leu Ser Thr Val Arg
        580                 585                 590

Asn Ala Asp Val Ile Ala Gly Phe Asp Asp Gly Val Ile Val Glu Lys
    595                 600                 605

Gly Asn His Asp Glu Leu Met Lys Glu Lys Gly Ile Tyr Phe Lys Leu
610                 615                 620

Val Thr Met Gln Thr Ala Gly Asn Glu Val Glu Leu Glu Asn Ala Ala
625                 630                 635                 640
```

-continued

```
Asp Glu Ser Lys Ser Glu Ile Asp Ala Leu Glu Met Ser Ser Asn Asp
            645                 650                 655

Ser Arg Ser Ser Leu Ile Arg Lys Arg Ser Thr Arg Ser Val Arg
        660                 665                 670

Gly Ser Gln Ala Gln Asp Arg Lys Leu Ser Thr Lys Glu Ala Leu Asp
            675                 680                 685

Glu Ser Ile Pro Pro Val Ser Phe Trp Arg Ile Met Lys Leu Asn Leu
690                 695                 700

Thr Glu Trp Pro Tyr Phe Val Gly Val Phe Cys Ala Ile Ile Asn
705                 710                 715                 720

Gly Gly Leu Gln Pro Ala Phe Ala Ile Ile Phe Ser Lys Ile Ile Gly
                725                 730                 735

Val Phe Thr Arg Ile Asp Asp Pro Glu Thr Lys Arg Gln Asn Ser Asn
                740                 745                 750

Leu Phe Ser Leu Leu Phe Leu Ala Leu Gly Ile Ile Ser Phe Ile Thr
            755                 760                 765

Phe Phe Leu Gln Gly Phe Thr Phe Gly Lys Ala Gly Glu Ile Leu Thr
770                 775                 780

Lys Arg Leu Arg Tyr Met Val Phe Arg Ser Met Leu Arg Gln Asp Val
785                 790                 795                 800

Ser Trp Phe Asp Asp Pro Lys Asn Thr Thr Gly Ala Leu Thr Thr Arg
                805                 810                 815

Leu Ala Asn Asp Ala Ala Gln Val Lys Gly Ala Ile Gly Ser Arg Leu
            820                 825                 830

Ala Val Ile Thr Gln Asn Ile Ala Asn Leu Gly Thr Gly Ile Ile Ile
            835                 840                 845

Ser Phe Ile Tyr Gly Trp Gln Leu Thr Leu Leu Leu Ala Ile Val
            850                 855                 860

Pro Ile Ile Ala Ile Ala Gly Val Val Glu Met Lys Met Leu Ser Gly
865                 870                 875                 880

Gln Ala Leu Lys Asp Lys Lys Glu Leu Glu Gly Ala Gly Lys Ile Ala
                885                 890                 895

Thr Glu Ala Ile Glu Asn Phe Arg Thr Val Val Ser Leu Thr Gln Glu
            900                 905                 910

Gln Lys Phe Glu His Met Tyr Ala Gln Ser Leu Gln Val Pro Tyr Arg
            915                 920                 925

Asn Ser Leu Arg Lys Ala His Ile Phe Gly Ile Thr Phe Ser Phe Thr
930                 935                 940

Gln Ala Met Met Tyr Phe Ser Tyr Ala Gly Cys Phe Arg Phe Gly Ala
945                 950                 955                 960

Tyr Leu Val Ala His Lys Leu Met Ser Phe Glu Asp Val Leu Leu Val
                965                 970                 975

Phe Ser Ala Val Val Phe Gly Ala Met Ala Val Gly Gln Val Ser Ser
            980                 985                 990

Phe Ala Pro Asp Tyr Ala Lys Ala Lys Ile Ser Ala Ala His Ile Ile
            995                 1000                1005

Met Ile Ile Glu Lys Thr Pro Leu Ile Asp Ser Tyr Ser Thr Glu Gly
            1010                1015                1020

Leu Met Pro Asn Thr Leu Glu Gly Asn Val Thr Phe Gly Glu Val Val
1025                1030                1035                1040

Phe Asn Tyr Pro Thr Arg Pro Asp Ile Pro Val Leu Gln Gly Leu Ser
            1045                1050                1055

Leu Glu Val Lys Lys Gly Gln Thr Leu Ala Leu Val Gly Ser Ser Gly
```

```
                          1060                1065                1070
        Cys Gly Lys Ser Thr Val Val Gln Leu Leu Glu Arg Phe Tyr Asp Pro
            1075                1080                1085
        Leu Ala Gly Lys Val Leu Leu Asp Gly Lys Glu Ile Lys Arg Leu Asn
            1090                1095                1100
        Val Gln Trp Leu Arg Ala His Leu Gly Ile Val Ser Gln Glu Pro Ile
        1105                1110                1115                1120
        Leu Phe Asp Cys Ser Ile Ala Glu Asn Ile Ala Tyr Gly Asp Asn Ser
                        1125                1130                1135
        Arg Val Val Ser Gln Glu Glu Ile Val Arg Ala Ala Lys Glu Ala Asn
                1140                1145                1150
        Ile His Ala Phe Ile Glu Ser Leu Pro Asn Lys Tyr Ser Thr Lys Val
                    1155                1160                1165
        Gly Asp Lys Gly Thr Gln Leu Ser Gly Gly Gln Lys Gln Arg Ile Ala
                1170                1175                1180
        Ile Ala Arg Ala Leu Val Arg Gln Pro His Ile Leu Leu Leu Asp Glu
        1185                1190                1195                1200
        Ala Thr Ser Ala Leu Asp Thr Glu Ser Glu Lys Val Val Gln Glu Ala
                        1205                1210                1215
        Leu Asp Lys Ala Arg Glu Gly Arg Thr Cys Ile Val Ile Ala His Arg
                    1220                1225                1230
        Leu Ser Thr Ile Gln Asn Ala Asp Leu Ile Val Val Phe Gln Asn Gly
                    1235                1240                1245
        Arg Val Lys Glu His Gly Thr His Gln Gln Leu Leu Ala Gln Lys Gly
            1250                1255                1260
        Ile Tyr Phe Ser Met Val Ser Val Gln Ala Gly Thr Lys Arg Gln
        1265                1270                1275

<210> SEQ ID NO 9
<211> LENGTH: 24
<212> TYPE: DNA
<213> ORGANISM: Homo sapiens

<400> SEQUENCE: 9
gaactgtgat tgcgtttgga ggac                                              24

<210> SEQ ID NO 10
<211> LENGTH: 22
<212> TYPE: DNA
<213> ORGANISM: Canis familiaris

<400> SEQUENCE: 10
ttcagggccg cctgtacctc tg                                                22

<210> SEQ ID NO 11
<211> LENGTH: 22
<212> TYPE: DNA
<213> ORGANISM: Canis familiaris

<400> SEQUENCE: 11
ccccacagat ggcatggtct gt                                                22

<210> SEQ ID NO 12
<211> LENGTH: 23
<212> TYPE: DNA
<213> ORGANISM: Homo sapiens

<400> SEQUENCE: 12
```

```
cgcttggtga ggatctctcc agc                                              23
```

<210> SEQ ID NO 13
<211> LENGTH: 24
<212> TYPE: DNA
<213> ORGANISM: Canis familiaris

<400> SEQUENCE: 13

```
agaaacagag aatcgccatt gctc                                             24
```

<210> SEQ ID NO 14
<211> LENGTH: 23
<212> TYPE: DNA
<213> ORGANISM: Homo sapiens

<400> SEQUENCE: 14

```
gctgcagtca aacaggatgg gct                                              23
```

<210> SEQ ID NO 15
<211> LENGTH: 24
<212> TYPE: DNA
<213> ORGANISM: Canis familiaris

<400> SEQUENCE: 15

```
agttcatttg ctcctgacta tgcc                                             24
```

<210> SEQ ID NO 16
<211> LENGTH: 22
<212> TYPE: DNA
<213> ORGANISM: Homo sapiens

<400> SEQUENCE: 16

```
gatgcctttc tgggccagca gc                                               22
```

<210> SEQ ID NO 17
<211> LENGTH: 30
<212> TYPE: DNA
<213> ORGANISM: Canis familiaris

<400> SEQUENCE: 17

```
gaggtgaaga agggccagac gctggccctc                                       30
```

<210> SEQ ID NO 18
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 18

```
ctaatacgac tcactatagg gcaagcagtg gtaacaacgc agagt                      45
```

<210> SEQ ID NO 19
<211> LENGTH: 29
<212> TYPE: DNA
<213> ORGANISM: Canis familiaris

<400> SEQUENCE: 19

```
cgcagccact gttcccaacc agcgccact                                        29
```

<210> SEQ ID NO 20
<211> LENGTH: 23
<212> TYPE: DNA
<213> ORGANISM: Homo sapiens -continued

```
<400> SEQUENCE: 20
ggagcgcgag gtcgggatgg atc                                                23

<210> SEQ ID NO 21
<211> LENGTH: 31
<212> TYPE: DNA
<213> ORGANISM: Canis familiaris

<400> SEQUENCE: 21
ggagaggacc aaggaggtcc cataccagaa a                                       31

<210> SEQ ID NO 22
<211> LENGTH: 4279
<212> TYPE: DNA
<213> ORGANISM: Canis familiaris
<220> FEATURE:
<221> NAME/KEY: CDS
<222> LOCATION: (17)...(3859)

<400> SEQUENCE: 22
ggagcgcgag gtcggg atg gat cct gaa gga ggc cgt aag ggg agt gca gag        52
               Met Asp Pro Glu Gly Gly Arg Lys Gly Ser Ala Glu
                 1               5                  10 aag aac ttc tgg aaa atg ggc aaa aaa agt aaa aaa aat gag aag aaa         100
Lys Asn Phe Trp Lys Met Gly Lys Lys Ser Lys Lys Asn Glu Lys Lys
         15                  20                  25 gaa aag aaa cca act gtc agc acg ttt gca atg ttt cgc tat tca aat         148
Glu Lys Lys Pro Thr Val Ser Thr Phe Ala Met Phe Arg Tyr Ser Asn
     30                  35                  40 tgg ctt gat agg ttg tat atg ttg gtg ggg aca atg gct gcc atc atc         196
Trp Leu Asp Arg Leu Tyr Met Leu Val Gly Thr Met Ala Ala Ile Ile
 45                  50                  55                  60 cat gga gct gca ctc cct ctc atg atg ctg gtt ttt gga aac atg aca         244
His Gly Ala Ala Leu Pro Leu Met Met Leu Val Phe Gly Asn Met Thr
                 65                  70                  75 gat agc ttt gca aat gca gga att tca aga aac aaa act ttt cca gtt         292
Asp Ser Phe Ala Asn Ala Gly Ile Ser Arg Asn Lys Thr Phe Pro Val
             80                  85                  90 ata att aat gaa agt att acg aac aat aca caa cat ttc atc aac cat         340
Ile Ile Asn Glu Ser Ile Thr Asn Asn Thr Gln His Phe Ile Asn His
         95                 100                 105 ctg gag gag gaa atg acc acg tat gcc tat tat tac agt ggg atc ggt         388
Leu Glu Glu Glu Met Thr Thr Tyr Ala Tyr Tyr Tyr Ser Gly Ile Gly
    110                 115                 120 gct ggc gtg ctg gtg gct gct tac atc cag gtt tca ttc tgg tgc ctg         436
Ala Gly Val Leu Val Ala Ala Tyr Ile Gln Val Ser Phe Trp Cys Leu
125                 130                 135                 140 gca gca gga aga cag ata ctc aaa att aga aaa caa ttt ttt cat gct         484
Ala Ala Gly Arg Gln Ile Leu Lys Ile Arg Lys Gln Phe Phe His Ala
                145                 150                 155 atc atg cga cag gag att ggc tgg ttt gac gtg cat gac gtt ggg gag         532
Ile Met Arg Gln Glu Ile Gly Trp Phe Asp Val His Asp Val Gly Glu
            160                 165                 170 ctt aac acc cgg ctc aca gac gat gtc tcc aaa atc aat gaa gga att         580
Leu Asn Thr Arg Leu Thr Asp Asp Val Ser Lys Ile Asn Glu Gly Ile
        175                 180                 185 ggc gac aaa att gga atg ttc ttt caa tca ata gca aca ttt ttc acc         628
Gly Asp Lys Ile Gly Met Phe Phe Gln Ser Ile Ala Thr Phe Phe Thr
    190                 195                 200 ggt ttt ata gtg ggg ttt aca cgt ggt tgg aag cta acc ctt gtg att         676
```

-continued

```
                Gly Phe Ile Val Gly Phe Thr Arg Gly Trp Lys Leu Thr Leu Val Ile
                205                 210                 215                 220 ttg gcc atc agc cct gtt ctt gga ctt tca gcc gcc atc tgg gca aag        724
Leu Ala Ile Ser Pro Val Leu Gly Leu Ser Ala Ala Ile Trp Ala Lys
                    225                 230                 235 ata cta tct tca ttt act gat aaa gaa ctc ttg gcc tat gca aaa gct        772
Ile Leu Ser Ser Phe Thr Asp Lys Glu Leu Leu Ala Tyr Ala Lys Ala
                240                 245                 250 gga gca gta gct gaa gaa gtc tta gca gca atc aga act gtg att gcc        820
Gly Ala Val Ala Glu Glu Val Leu Ala Ala Ile Arg Thr Val Ile Ala
                255                 260                 265 ttt gga gga caa aag aaa gaa ctt gaa agg tac aac aaa aat tta gaa        868
Phe Gly Gly Gln Lys Lys Glu Leu Glu Arg Tyr Asn Lys Asn Leu Glu
                270                 275                 280 gaa gct aaa gga att ggg ata aag aaa gct atc acg gcc aac att tct        916
Glu Ala Lys Gly Ile Gly Ile Lys Lys Ala Ile Thr Ala Asn Ile Ser
285                 290                 295                 300 att ggt gcc gct ttc tta ttg atc tat gca tca tat gct ctg gct ttc        964
Ile Gly Ala Ala Phe Leu Leu Ile Tyr Ala Ser Tyr Ala Leu Ala Phe
                    305                 310                 315 tgg tat ggg acc tcc ttg gtc ctc tcc agt gaa tat tct att gga caa       1012
Trp Tyr Gly Thr Ser Leu Val Leu Ser Glu Tyr Ser Ile Gly Gln
                320                 325                 330 gta ctc act gtc ttc ttt tct gta tta att ggg gct ttt agt att gga       1060
Val Leu Thr Val Phe Phe Ser Val Leu Ile Gly Ala Phe Ser Ile Gly
                335                 340                 345 cag gca tcc cca agc att gaa gca ttt gca aac gca aga gga gca gct       1108
Gln Ala Ser Pro Ser Ile Glu Ala Phe Ala Asn Ala Arg Gly Ala Ala
                350                 355                 360 tat gaa atc ttc aag ata att gac aat aaa cca agc att gac agc tat       1156
Tyr Glu Ile Phe Lys Ile Ile Asp Asn Lys Pro Ser Ile Asp Ser Tyr
365                 370                 375                 380 tcg aag agt gga cat aaa cca gat aat att aag gga aat ttg gaa ttc       1204
Ser Lys Ser Gly His Lys Pro Asp Asn Ile Lys Gly Asn Leu Glu Phe
                    385                 390                 395 aaa aat gtt cac ttc agt tac cct tct cga aaa gaa gtt aag atc tta       1252
Lys Asn Val His Phe Ser Tyr Pro Ser Arg Lys Glu Val Lys Ile Leu
                400                 405                 410 aag ggt ctc aac ctg aag gtt cag agt ggg cag aca gtg gcg ctg gtt       1300
Lys Gly Leu Asn Leu Lys Val Gln Ser Gly Gln Thr Val Ala Leu Val
                415                 420                 425 ggg aac agt ggc tgc ggg aag agc acg acc gtg cag ctg atg cag agg       1348
Gly Asn Ser Gly Cys Gly Lys Ser Thr Thr Val Gln Leu Met Gln Arg
                430                 435                 440 ctc tat gac ccc aca gat ggc atg gtc tgt att gat gga cag gac att       1396
Leu Tyr Asp Pro Thr Asp Gly Met Val Cys Ile Asp Gly Gln Asp Ile
445                 450                 455                 460 agg acc ata aat gta agg cat ctt cgg gaa att act ggt gtg gtg agt       1444
Arg Thr Ile Asn Val Arg His Leu Arg Glu Ile Thr Gly Val Val Ser
                    465                 470                 475 cag gag cct gtg ttg ttt gcc acc acg ata gct gaa aac att cgc tat       1492
Gln Glu Pro Val Leu Phe Ala Thr Thr Ile Ala Glu Asn Ile Arg Tyr
                480                 485                 490 ggc cgc gaa aat gtc acc atg gat gag att gag aaa gct gtt aag gaa       1540
Gly Arg Glu Asn Val Thr Met Asp Glu Ile Glu Lys Ala Val Lys Glu
                495                 500                 505 gcc aat gcc tat gat ttt atc atg aaa cta cct aat aaa ttt gac act       1588
Ala Asn Ala Tyr Asp Phe Ile Met Lys Leu Pro Asn Lys Phe Asp Thr
510                 515                 520
```

```
ctg gtt gga gag aga ggg gcc cag ctg agt ggt gga cag aaa cag aga    1636
Leu Val Gly Glu Arg Gly Ala Gln Leu Ser Gly Gly Gln Lys Gln Arg
525                 530                 535                 540 atc gcc att gct cgg gcc ctg gtt cgc aac ccc aag att ctt ctg ctg    1684
Ile Ala Ile Ala Arg Ala Leu Val Arg Asn Pro Lys Ile Leu Leu Leu
                545                 550                 555 gat gag gca acg tca gct ctg gac act gaa agt gaa gca gtg gtt cag    1732
Asp Glu Ala Thr Ser Ala Leu Asp Thr Glu Ser Glu Ala Val Val Gln
            560                 565                 570 gtg gcc ctg gat aag gcc aga aaa ggc cgg act acc att gtg ata gct    1780
Val Ala Leu Asp Lys Ala Arg Lys Gly Arg Thr Thr Ile Val Ile Ala
        575                 580                 585 cat cgt ttg tct aca gtt cgt aat gcc gat gtc att gct ggt ttt gat    1828
His Arg Leu Ser Thr Val Arg Asn Ala Asp Val Ile Ala Gly Phe Asp
    590                 595                 600 gat gga gtc att gtg gag aaa gga aat cat gat gaa ctc atg aaa gag    1876
Asp Gly Val Ile Val Glu Lys Gly Asn His Asp Glu Leu Met Lys Glu
605                 610                 615                 620 aag ggc att tac ttc aaa ctt gtc aca atg cag aca aga gga aat gaa    1924
Lys Gly Ile Tyr Phe Lys Leu Val Thr Met Gln Thr Arg Gly Asn Glu
                625                 630                 635 att gag tta gaa aat gcc act ggt gaa tcc aaa agt gaa agt gat gcc    1972
Ile Glu Leu Glu Asn Ala Thr Gly Glu Ser Lys Ser Glu Ser Asp Ala
            640                 645                 650 ttg gaa atg tct cca aaa gat tca ggg tcc agt tta ata aaa aga aga    2020
Leu Glu Met Ser Pro Lys Asp Ser Gly Ser Ser Leu Ile Lys Arg Arg
        655                 660                 665 tca act cgc agg agt ata cat gca cca caa ggc caa gac aga aag ctt    2068
Ser Thr Arg Arg Ser Ile His Ala Pro Gln Gly Gln Asp Arg Lys Leu
    670                 675                 680 ggt aca aaa gag gac ttg aat gag aat gta cct cca gtt tcc ttc tgg    2116
Gly Thr Lys Glu Asp Leu Asn Glu Asn Val Pro Pro Val Ser Phe Trp
685                 690                 695                 700 agg att ctg aag ctg aac tca act gaa tgg cct tat ttt gtg gtt ggt    2164
Arg Ile Leu Lys Leu Asn Ser Thr Glu Trp Pro Tyr Phe Val Val Gly
                705                 710                 715 ata ttt tgt gct att ata aac gga ggc ctg caa cca gca ttt tca ata    2212
Ile Phe Cys Ala Ile Ile Asn Gly Gly Leu Gln Pro Ala Phe Ser Ile
            720                 725                 730 ata ttt tca agg att ata ggg atc ttt acc cga gat gag gat cct gaa    2260
Ile Phe Ser Arg Ile Ile Gly Ile Phe Thr Arg Asp Glu Asp Pro Glu
        735                 740                 745 aca aaa cga cag aat agt aac atg ttt tct gta ttg ttt cta gtc ctt    2308
Thr Lys Arg Gln Asn Ser Asn Met Phe Ser Val Leu Phe Leu Val Leu
    750                 755                 760 gga att att tct ttt att aca ttt ttc ctc cag ggc ttc aca ttt ggc    2356
Gly Ile Ile Ser Phe Ile Thr Phe Phe Leu Gln Gly Phe Thr Phe Gly
765                 770                 775                 780 aaa gct ggg gag atc ctc act aag cgg ctt cga tac atg gtt ttc aga    2404
Lys Ala Gly Glu Ile Leu Thr Lys Arg Leu Arg Tyr Met Val Phe Arg
                785                 790                 795 tcc atg ctg aga cag gat gtc agc tgg ttt gat gac cct aaa aac acc    2452
Ser Met Leu Arg Gln Asp Val Ser Trp Phe Asp Asp Pro Lys Asn Thr
            800                 805                 810 act gga gca ttg aca acc agg ctt gcc aat gat gcg gct caa gtt aaa    2500
Thr Gly Ala Leu Thr Thr Arg Leu Ala Asn Asp Ala Ala Gln Val Lys
        815                 820                 825 ggg gct ata ggt tcc agg ctt gct gtc att acc cag aat ata gca aat    2548
Gly Ala Ile Gly Ser Arg Leu Ala Val Ile Thr Gln Asn Ile Ala Asn
    830                 835                 840
```

-continued

| | |
|---|---|
| ctt ggg aca ggc att att ata tcc tta atc tat ggt tgg caa tta aca<br>Leu Gly Thr Gly Ile Ile Ile Ser Leu Ile Tyr Gly Trp Gln Leu Thr<br>845                        850                  855                    860 | 2596 |
| ctt tta ctc tta gca att gta ccc atc att gca ata gca gga gtt gtt<br>Leu Leu Leu Leu Ala Ile Val Pro Ile Ile Ala Ile Ala Gly Val Val<br>                  865                  870                  875 | 2644 |
| gaa atg aaa atg ttg tct gga caa gca ctg aaa gat aag aaa gag cta<br>Glu Met Lys Met Leu Ser Gly Gln Ala Leu Lys Asp Lys Lys Glu Leu<br>880                        885                  890 | 2692 |
| gaa gga gct ggg aag att gct aca gaa gcc atc gaa aac ttc cga act<br>Glu Gly Ala Gly Lys Ile Ala Thr Glu Ala Ile Glu Asn Phe Arg Thr<br>        895                  900                  905 | 2740 |
| gtt gtt tct ttg act cgg gag cag aag ttt gaa tac atg tat gca cag<br>Val Val Ser Leu Thr Arg Glu Gln Lys Phe Glu Tyr Met Tyr Ala Gln<br>910                        915                  920 | 2788 |
| agt ttg caa gta cca tac aga aac tct ttg agg aaa gca cac atc ttc<br>Ser Leu Gln Val Pro Tyr Arg Asn Ser Leu Arg Lys Ala His Ile Phe<br>925                        930                  935                  940 | 2836 |
| ggg gtc tca ttt tct atc acc cag gca atg atg tat ttt tcc tat gct<br>Gly Val Ser Phe Ser Ile Thr Gln Ala Met Met Tyr Phe Ser Tyr Ala<br>                  945                  950                  955 | 2884 |
| ggc tgt ttc cgg ttt ggt gcc tac ttg gtg gca aat gag ttc atg aac<br>Gly Cys Phe Arg Phe Gly Ala Tyr Leu Val Ala Asn Glu Phe Met Asn<br>                  960                  965                  970 | 2932 |
| ttt cag gat gtt ctt ttg gta ttc tca gct att gtc ttt ggt gcc atg<br>Phe Gln Asp Val Leu Leu Val Phe Ser Ala Ile Val Phe Gly Ala Met<br>        975                  980                  985 | 2980 |
| gca gtg ggg cag gtc agt tca ttt gct cct gac tat gcc aaa gcc aaa<br>Ala Val Gly Gln Val Ser Ser Phe Ala Pro Asp Tyr Ala Lys Ala Lys<br>990                        995                  1000 | 3028 |
| gta tca gca gcc cac gtc atc atg atc att gaa aaa agc cct ctg att<br>Val Ser Ala Ala His Val Ile Met Ile Ile Glu Lys Ser Pro Leu Ile<br>1005                        1010                  1015                  1020 | 3076 |
| gac agc tac agc cct cac ggc ctc aag cca aat acg ttg gaa gga aat<br>Asp Ser Tyr Ser Pro His Gly Leu Lys Pro Asn Thr Leu Glu Gly Asn<br>                  1025                  1030                  1035 | 3124 |
| gtg aca ttt aat gag gtc gtg ttc aac tat ccc act cga cca gac atc<br>Val Thr Phe Asn Glu Val Val Phe Asn Tyr Pro Thr Arg Pro Asp Ile<br>                  1040                  1045                  1050 | 3172 |
| ccc gtg ctc cag ggg ctg agc ctc gag gtg aag aag ggc cag acg ctg<br>Pro Val Leu Gln Gly Leu Ser Leu Glu Val Lys Lys Gly Gln Thr Leu<br>1055                        1060                  1065 | 3220 |
| gcc ctc gta ggt agc agt ggc tgt ggg aag agc aca gtt gtt cag ctc<br>Ala Leu Val Gly Ser Ser Gly Cys Gly Lys Ser Thr Val Val Gln Leu<br>1070                        1075                  1080 | 3268 |
| cta gag cgc ttc tat gac ccc ttg gct ggt tca gtg cta att gat ggc<br>Leu Glu Arg Phe Tyr Asp Pro Leu Ala Gly Ser Val Leu Ile Asp Gly<br>1085                        1090                  1095                  1100 | 3316 |
| aaa gag ata aag cac ctg aat gtc cag tgg ctc cga gca cac ctg ggc<br>Lys Glu Ile Lys His Leu Asn Val Gln Trp Leu Arg Ala His Leu Gly<br>                  1105                  1110                  1115 | 3364 |
| atc gtg tct cag gag ccc atc ctg ttt gac tgc agc att gcc gag aac<br>Ile Val Ser Gln Glu Pro Ile Leu Phe Asp Cys Ser Ile Ala Glu Asn<br>                  1120                  1125                  1130 | 3412 |
| att gcc tat gga gac aac agc cgg gtc gta tca cat gaa gag att atg<br>Ile Ala Tyr Gly Asp Asn Ser Arg Val Val Ser His Glu Glu Ile Met<br>                  1135                  1140                  1145 | 3460 |
| cag gca gcc aag gag gcc aac ata cac cac ttc atc gag aca ctc cct<br>Gln Ala Ala Lys Glu Ala Asn Ile His His Phe Ile Glu Thr Leu Pro | 3508 |

```
                1150              1155              1160
gag aaa tac aac acc aga gta gga gac aaa gga acc cag ctc tct ggt      3556
Glu Lys Tyr Asn Thr Arg Val Gly Asp Lys Gly Thr Gln Leu Ser Gly
1165              1170              1175              1180 ggc cag aaa cag cgc att gcc ata gct cgc gct ctt gtt aga cag cct      3604
Gly Gln Lys Gln Arg Ile Ala Ile Ala Arg Ala Leu Val Arg Gln Pro
            1185              1190              1195 cat att ttg ctt ttg gat gaa gct aca tca gct ctg gat aca gaa agt      3652
His Ile Leu Leu Leu Asp Glu Ala Thr Ser Ala Leu Asp Thr Glu Ser
        1200              1205              1210 gaa aag gtt gtc caa gaa gcc ctg gac aaa gcc aga gaa ggc cgc acc      3700
Glu Lys Val Val Gln Glu Ala Leu Asp Lys Ala Arg Glu Gly Arg Thr
    1215              1220              1225 tgc att gtg atc gcc cac cgc ttg tcc acc atc cag aat gca gat tta      3748
Cys Ile Val Ile Ala His Arg Leu Ser Thr Ile Gln Asn Ala Asp Leu
1230              1235              1240 ata gtg gtg ttt cag aat ggc aaa gtc aag gag cat ggc aca cat caa      3796
Ile Val Val Phe Gln Asn Gly Lys Val Lys Glu His Gly Thr His Gln
1245              1250              1255              1260 cag ctg ctg gcc cag aaa ggc atc tat ttt tcc atg gtc agt gtc cag      3844
Gln Leu Leu Ala Gln Lys Gly Ile Tyr Phe Ser Met Val Ser Val Gln
            1265              1270              1275 gct gga gca aag cgc tagtgaactg tggccatatg agctgttaaa tattttttaa      3899
Ala Gly Ala Lys Arg
            1280 tatttgtgtt aaaacatggc atttaatcaa agttaaaagg tgagcactta ctggaaaaac      3959 tatgtagaac tacctgttta acatttcttg ctgcaactga agatcattcc accaagttca      4019 gagtcttcag attttataat taaaggaacc aaaagaaaca ttatctgatg gaataaaata      4079 ctggtgttaa ttgcattata aaattataga gtaattcaaa gtagattttg ttaataaatt      4139 gtataatttt tgtttatatt ttatttgtaa cttactgctt tgctgaaaga ttatagaagt      4199 ggtaaaaagt actgaatgtt tgaataaagt gctagctata ataaaactaa acttttatat      4259 caaaaaaaaa aaaaaaaaaa                                                  4279

<210> SEQ ID NO 23
<211> LENGTH: 1281
<212> TYPE: PRT
<213> ORGANISM: Canis familiaris

<400> SEQUENCE: 23

Met Asp Pro Glu Gly Gly Arg Lys Gly Ser Ala Glu Lys Asn Phe Trp
1               5                   10                  15

Lys Met Gly Lys Lys Ser Lys Lys Asn Glu Lys Lys Glu Lys Lys Pro
            20                  25                  30

Thr Val Ser Thr Phe Ala Met Phe Arg Tyr Ser Asn Trp Leu Asp Arg
        35                  40                  45

Leu Tyr Met Leu Val Gly Thr Met Ala Ala Ile His Gly Ala Ala
    50                  55                  60

Leu Pro Leu Met Met Leu Val Phe Gly Asn Met Thr Asp Ser Phe Ala
65                  70                  75                  80

Asn Ala Gly Ile Ser Arg Asn Lys Thr Phe Pro Val Ile Ile Asn Glu
            85                  90                  95

Ser Ile Thr Asn Asn Thr Gln His Phe Ile Asn His Leu Glu Glu Glu
            100                 105                 110

Met Thr Thr Tyr Ala Tyr Tyr Tyr Ser Gly Ile Gly Ala Gly Val Leu
        115                 120                 125
```

```
Val Ala Ala Tyr Ile Gln Val Ser Phe Trp Cys Leu Ala Ala Gly Arg
        130                 135                 140

Gln Ile Leu Lys Ile Arg Lys Gln Phe Phe His Ala Ile Met Arg Gln
145                 150                 155                 160

Glu Ile Gly Trp Phe Asp Val His Asp Val Gly Glu Leu Asn Thr Arg
                    165                 170                 175

Leu Thr Asp Val Ser Lys Ile Asn Glu Gly Ile Gly Asp Lys Ile
                180                 185                 190

Gly Met Phe Phe Gln Ser Ile Ala Thr Phe Thr Gly Phe Ile Val
                195                 200                 205

Gly Phe Thr Arg Gly Trp Lys Leu Thr Leu Val Ile Leu Ala Ile Ser
        210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
                260                 265                 270

Lys Lys Glu Leu Glu Arg Tyr Asn Lys Asn Leu Glu Glu Ala Lys Gly
                275                 280                 285

Ile Gly Ile Lys Lys Ala Ile Thr Ala Asn Ile Ser Ile Gly Ala Ala
        290                 295                 300

Phe Leu Leu Ile Tyr Ala Ser Tyr Ala Leu Ala Phe Trp Tyr Gly Thr
305                 310                 315                 320

Ser Leu Val Leu Ser Ser Glu Tyr Ser Ile Gly Gln Val Leu Thr Val
                325                 330                 335

Phe Phe Ser Val Leu Ile Gly Ala Phe Ser Ile Gly Gln Ala Ser Pro
                340                 345                 350

Ser Ile Glu Ala Phe Ala Asn Ala Arg Gly Ala Ala Tyr Glu Ile Phe
        355                 360                 365

Lys Ile Ile Asp Asn Lys Pro Ser Ile Asp Ser Tyr Ser Lys Ser Gly
370                 375                 380

His Lys Pro Asp Asn Ile Lys Gly Asn Leu Glu Phe Lys Asn Val His
385                 390                 395                 400

Phe Ser Tyr Pro Ser Arg Lys Glu Val Lys Ile Leu Lys Gly Leu Asn
                405                 410                 415

Leu Lys Val Gln Ser Gly Gln Thr Val Ala Leu Val Gly Asn Ser Gly
                420                 425                 430

Cys Gly Lys Ser Thr Thr Val Gln Leu Met Gln Arg Leu Tyr Asp Pro
        435                 440                 445

Thr Asp Gly Met Val Cys Ile Asp Gly Gln Asp Ile Arg Thr Ile Asn
        450                 455                 460

Val Arg His Leu Arg Glu Ile Thr Gly Val Val Ser Gln Glu Pro Val
465                 470                 475                 480

Leu Phe Ala Thr Thr Ile Ala Glu Asn Ile Arg Tyr Gly Arg Glu Asn
                485                 490                 495

Val Thr Met Asp Glu Ile Glu Lys Ala Val Lys Glu Ala Asn Ala Tyr
                500                 505                 510

Asp Phe Ile Met Lys Leu Pro Asn Lys Phe Asp Thr Leu Val Gly Glu
                515                 520                 525

Arg Gly Ala Gln Leu Ser Gly Gly Gln Lys Gln Arg Ile Ala Ile Ala
530                 535                 540
```

-continued

```
Arg Ala Leu Val Arg Asn Pro Lys Ile Leu Leu Leu Asp Glu Ala Thr
545                 550                 555                 560

Ser Ala Leu Asp Thr Glu Ser Glu Ala Val Val Gln Val Ala Leu Asp
                565                 570                 575

Lys Ala Arg Lys Gly Arg Thr Thr Ile Val Ile Ala His Arg Leu Ser
            580                 585                 590

Thr Val Arg Asn Ala Asp Val Ile Ala Gly Phe Asp Asp Gly Val Ile
        595                 600                 605

Val Glu Lys Gly Asn His Asp Glu Leu Met Lys Glu Lys Gly Ile Tyr
    610                 615                 620

Phe Lys Leu Val Thr Met Gln Thr Arg Gly Asn Glu Ile Glu Leu Glu
625                 630                 635                 640

Asn Ala Thr Gly Glu Ser Lys Ser Glu Ser Asp Ala Leu Glu Met Ser
                645                 650                 655

Pro Lys Asp Ser Gly Ser Ser Leu Ile Lys Arg Arg Ser Thr Arg Arg
            660                 665                 670

Ser Ile His Ala Pro Gln Gly Gln Asp Arg Lys Leu Gly Thr Lys Glu
        675                 680                 685

Asp Leu Asn Glu Asn Val Pro Pro Val Ser Phe Trp Arg Ile Leu Lys
    690                 695                 700

Leu Asn Ser Thr Glu Trp Pro Tyr Phe Val Val Gly Ile Phe Cys Ala
705                 710                 715                 720

Ile Ile Asn Gly Gly Leu Gln Pro Ala Phe Ser Ile Ile Phe Ser Arg
                725                 730                 735

Ile Ile Gly Ile Phe Thr Arg Asp Glu Asp Pro Glu Thr Lys Arg Gln
            740                 745                 750

Asn Ser Asn Met Phe Ser Val Leu Phe Leu Val Leu Gly Ile Ile Ser
        755                 760                 765

Phe Ile Thr Phe Phe Leu Gln Gly Phe Thr Phe Gly Lys Ala Gly Glu
    770                 775                 780

Ile Leu Thr Lys Arg Leu Arg Tyr Met Val Phe Arg Ser Met Leu Arg
785                 790                 795                 800

Gln Asp Val Ser Trp Phe Asp Asp Pro Lys Asn Thr Thr Gly Ala Leu
                805                 810                 815

Thr Thr Arg Leu Ala Asn Asp Ala Ala Gln Val Lys Gly Ala Ile Gly
            820                 825                 830

Ser Arg Leu Ala Val Ile Thr Gln Asn Ile Ala Asn Leu Gly Thr Gly
        835                 840                 845

Ile Ile Ile Ser Leu Ile Tyr Gly Trp Gln Leu Thr Leu Leu Leu Leu
    850                 855                 860

Ala Ile Val Pro Ile Ile Ala Ile Ala Gly Val Val Glu Met Lys Met
865                 870                 875                 880

Leu Ser Gly Gln Ala Leu Lys Asp Lys Lys Glu Leu Glu Gly Ala Gly
                885                 890                 895

Lys Ile Ala Thr Glu Ala Ile Glu Asn Phe Arg Thr Val Val Ser Leu
            900                 905                 910

Thr Arg Glu Gln Lys Phe Glu Tyr Met Tyr Ala Gln Ser Leu Gln Val
        915                 920                 925

Pro Tyr Arg Asn Ser Leu Arg Lys Ala His Ile Phe Gly Val Ser Phe
    930                 935                 940

Ser Ile Thr Gln Ala Met Met Tyr Phe Ser Tyr Ala Gly Cys Phe Arg
945                 950                 955                 960

Phe Gly Ala Tyr Leu Val Ala Asn Glu Phe Met Asn Phe Gln Asp Val
```

-continued

```
                    965                 970                 975
Leu Leu Val Phe Ser Ala Ile Val Phe Gly Ala Met Ala Val Gly Gln
            980                 985                 990
Val Ser Ser Phe Ala Pro Asp Tyr Ala Lys Ala Lys Val Ser Ala Ala
            995                1000                1005
His Val Ile Met Ile Ile Glu Lys Ser Pro Leu Ile Asp Ser Tyr Ser
           1010                1015                1020
Pro His Gly Leu Lys Pro Asn Thr Leu Glu Gly Asn Val Thr Phe Asn
1025                1030                1035                1040
Glu Val Val Phe Asn Tyr Pro Thr Arg Pro Asp Ile Pro Val Leu Gln
                1045                1050                1055
Gly Leu Ser Leu Glu Val Lys Lys Gly Gln Thr Leu Ala Leu Val Gly
                1060                1065                1070
Ser Ser Gly Cys Gly Lys Ser Thr Val Val Gln Leu Leu Glu Arg Phe
                1075                1080                1085
Tyr Asp Pro Leu Ala Gly Ser Val Leu Ile Asp Gly Lys Glu Ile Lys
                1090                1095                1100
His Leu Asn Val Gln Trp Leu Arg Ala His Leu Gly Ile Val Ser Gln
1105                1110                1115                1120
Glu Pro Ile Leu Phe Asp Cys Ser Ile Ala Glu Asn Ile Ala Tyr Gly
                1125                1130                1135
Asp Asn Ser Arg Val Val Ser His Glu Glu Ile Met Gln Ala Ala Lys
                1140                1145                1150
Glu Ala Asn Ile His His Phe Ile Glu Thr Leu Pro Glu Lys Tyr Asn
                1155                1160                1165
Thr Arg Val Gly Asp Lys Gly Thr Gln Leu Ser Gly Gly Gln Lys Gln
                1170                1175                1180
Arg Ile Ala Ile Ala Arg Ala Leu Val Arg Gln Pro His Ile Leu Leu
1185                1190                1195                1200
Leu Asp Glu Ala Thr Ser Ala Leu Asp Thr Glu Ser Glu Lys Val Val
                1205                1210                1215
Gln Glu Ala Leu Asp Lys Ala Arg Glu Gly Arg Thr Cys Ile Val Ile
                1220                1225                1230
Ala His Arg Leu Ser Thr Ile Gln Asn Ala Asp Leu Ile Val Val Phe
                1235                1240                1245
Gln Asn Gly Lys Val Lys Glu His Gly Thr His Gln Gln Leu Leu Ala
                1250                1255                1260
Gln Lys Gly Ile Tyr Phe Ser Met Val Ser Val Gln Ala Gly Ala Lys
1265                1270                1275                1280
Arg
```

<210> SEQ ID NO 24
<211> LENGTH: 4279
<212> TYPE: DNA
<213> ORGANISM: Canis familiaris
<220> FEATURE:
<221> NAME/KEY: CDS
<222> LOCATION: (17)...(3859)

<400> SEQUENCE: 24

```
ggagcgcgag gtcggg atg gat cct gaa gga ggc cgt aag ggg agt gca gag    52
                Met Asp Pro Glu Gly Gly Arg Lys Gly Ser Ala Glu
                  1               5                  10 aag aac ttc tgg aaa atg ggc aaa aaa agt aaa aaa aaa gag aag aaa   100
Lys Asn Phe Trp Lys Met Gly Lys Lys Ser Lys Lys Lys Glu Lys Lys
         15                  20                  25
```

-continued

```
gaa aag aaa cca act gtc agc acg ttt gca atg ttt cgc tat tca aat      148
Glu Lys Lys Pro Thr Val Ser Thr Phe Ala Met Phe Arg Tyr Ser Asn
 30              35                  40 tgg ctt gat agg ttg tat atg ttg gtg gga aca atg gct gcc atc atc      196
Trp Leu Asp Arg Leu Tyr Met Leu Val Gly Thr Met Ala Ala Ile Ile
 45              50                  55                  60 cat gga gct gca ctc cct ctc atg atg ctg gtt ttt gga aac atg aca      244
His Gly Ala Ala Leu Pro Leu Met Met Leu Val Phe Gly Asn Met Thr
                 65                  70                  75 gat agc ttt gca aat gca gga att tca aga aac aaa act ttt cca gtt      292
Asp Ser Phe Ala Asn Ala Gly Ile Ser Arg Asn Lys Thr Phe Pro Val
             80                  85                  90 ata att aat gaa agt att acg aac aat aca caa cat ttc atc aac cat      340
Ile Ile Asn Glu Ser Ile Thr Asn Asn Thr Gln His Phe Ile Asn His
             95                 100                 105 ctg gag gag gaa atg acc acg tat gcc tat tat tac agt ggg atc ggt      388
Leu Glu Glu Glu Met Thr Thr Tyr Ala Tyr Tyr Tyr Ser Gly Ile Gly
    110                 115                 120 gct ggc gtg ctg gtg gct gct tac atc cag gtt tca ttc tgg tgc ctg      436
Ala Gly Val Leu Val Ala Ala Tyr Ile Gln Val Ser Phe Trp Cys Leu
125                 130                 135                 140 gca gca gga aga cag ata ctc aaa att aga aaa caa ttt ttt cat gct      484
Ala Ala Gly Arg Gln Ile Leu Lys Ile Arg Lys Gln Phe Phe His Ala
                145                 150                 155 atc atg cga cag gag att ggc tgg ttt gac gtg cat gac gtt ggg gag      532
Ile Met Arg Gln Glu Ile Gly Trp Phe Asp Val His Asp Val Gly Glu
            160                 165                 170 ctt aac acc cgg ctc aca gac gat gtc tcc aaa atc aat gaa gga att      580
Leu Asn Thr Arg Leu Thr Asp Asp Val Ser Lys Ile Asn Glu Gly Ile
            175                 180                 185 ggc gac aaa att gga atg ttc ttt caa tca ata gca aca ttt ttc acc      628
Gly Asp Lys Ile Gly Met Phe Phe Gln Ser Ile Ala Thr Phe Phe Thr
190                 195                 200 ggt ttt ata gtg ggg ttt aca cgt ggt tgg aag cta acc ctt gtg att      676
Gly Phe Ile Val Gly Phe Thr Arg Gly Trp Lys Leu Thr Leu Val Ile
205                 210                 215                 220 ttg gcc atc agc cct gtt ctt gga ctt tca gcc gcc atc tgg gca aag      724
Leu Ala Ile Ser Pro Val Leu Gly Leu Ser Ala Ala Ile Trp Ala Lys
                225                 230                 235 ata cta tct tca ttt act gat aaa gaa ctc ttg gcc tat gca aaa gct      772
Ile Leu Ser Ser Phe Thr Asp Lys Glu Leu Leu Ala Tyr Ala Lys Ala
            240                 245                 250 gga gca gta gct gaa gaa gtc tta gca gca atc aga act gtg att gcc      820
Gly Ala Val Ala Glu Glu Val Leu Ala Ala Ile Arg Thr Val Ile Ala
            255                 260                 265 ttt gga gga caa aag aaa gaa ctt gaa agg tac aac aaa aat tta gaa      868
Phe Gly Gly Gln Lys Lys Glu Leu Glu Arg Tyr Asn Lys Asn Leu Glu
        270                 275                 280 gaa gct aaa gga att ggg ata aag aaa gct atc acg gcc aac att tct      916
Glu Ala Lys Gly Ile Gly Ile Lys Lys Ala Ile Thr Ala Asn Ile Ser
285                 290                 295                 300 att ggt gcc gct ttc tta ttg atc tat gca tca tat gct ctg gct ttc      964
Ile Gly Ala Ala Phe Leu Leu Ile Tyr Ala Ser Tyr Ala Leu Ala Phe
                305                 310                 315 tgg tat ggg acc tcc ttg gtc ctc tcc agt gaa tat tct att gga caa     1012
Trp Tyr Gly Thr Ser Leu Val Leu Ser Ser Glu Tyr Ser Ile Gly Gln
            320                 325                 330 gta ctc act gtc ttc ttt tct gta tta att ggg gct ttt agt att gga     1060
Val Leu Thr Val Phe Phe Ser Val Leu Ile Gly Ala Phe Ser Ile Gly
```

```
                    335                 340                 345
cag gca tcc cca agc att gaa gca ttt gca aac gca aga gga gca gct      1108
Gln Ala Ser Pro Ser Ile Glu Ala Phe Ala Asn Ala Arg Gly Ala Ala
    350                 355                 360 tat gaa atc ttc aag ata att gac aat aaa cca agc att gac agc tat      1156
Tyr Glu Ile Phe Lys Ile Ile Asp Asn Lys Pro Ser Ile Asp Ser Tyr
365                 370                 375                 380 tcg aag agt gga cat aaa cca gat aat att aag gga aat ttg gaa ttc      1204
Ser Lys Ser Gly His Lys Pro Asp Asn Ile Lys Gly Asn Leu Glu Phe
                385                 390                 395 aaa aat gtt cac ttc agt tac cct tct cga aaa gaa gtt aag atc tta      1252
Lys Asn Val His Phe Ser Tyr Pro Ser Arg Lys Glu Val Lys Ile Leu
            400                 405                 410 aag ggt ctc aac ctg aag gtt cag agt ggg cag aca gtg gcg ctg gtt      1300
Lys Gly Leu Asn Leu Lys Val Gln Ser Gly Gln Thr Val Ala Leu Val
        415                 420                 425 ggg aac agt ggc tgc ggg aag agc acg acc gtg cag ctg atg cag agg      1348
Gly Asn Ser Gly Cys Gly Lys Ser Thr Thr Val Gln Leu Met Gln Arg
    430                 435                 440 ctc tat gac ccc aca gat ggc atg gtc tgt att gat gga cag gac att      1396
Leu Tyr Asp Pro Thr Asp Gly Met Val Cys Ile Asp Gly Gln Asp Ile
445                 450                 455                 460 agg acc ata aat gta agg cat ctt cgg gaa att act ggt gtg gtg agt      1444
Arg Thr Ile Asn Val Arg His Leu Arg Glu Ile Thr Gly Val Val Ser
                465                 470                 475 cag gag cct gtg ttg ttt gcc acc acg ata gct gaa aac att cgc tat      1492
Gln Glu Pro Val Leu Phe Ala Thr Thr Ile Ala Glu Asn Ile Arg Tyr
            480                 485                 490 ggc cgc gaa aat gtc acc atg gat gag att gag aaa gct gtt aag gaa      1540
Gly Arg Glu Asn Val Thr Met Asp Glu Ile Glu Lys Ala Val Lys Glu
        495                 500                 505 gcc aat gcc tat gat ttt atc atg aaa cta cct aat aaa ttt gac act      1588
Ala Asn Ala Tyr Asp Phe Ile Met Lys Leu Pro Asn Lys Phe Asp Thr
    510                 515                 520 ctg gtt gga gag aga ggg gcc cag ctg agt ggt gga cag aaa cag aga      1636
Leu Val Gly Glu Arg Gly Ala Gln Leu Ser Gly Gly Gln Lys Gln Arg
525                 530                 535                 540 atc gcc att gct cgg gcc ctg gtt cgc aac ccc aag att ctt ctg ctg      1684
Ile Ala Ile Ala Arg Ala Leu Val Arg Asn Pro Lys Ile Leu Leu Leu
                545                 550                 555 gat gag gca acg tca gct ctg gac act gaa agt gaa gca gtg gtt cag      1732
Asp Glu Ala Thr Ser Ala Leu Asp Thr Glu Ser Glu Ala Val Val Gln
            560                 565                 570 gtg gcc ctg gat aag gcc aga aaa ggc cgg act acc att gtg ata gct      1780
Val Ala Leu Asp Lys Ala Arg Lys Gly Arg Thr Thr Ile Val Ile Ala
        575                 580                 585 cat cgt ttg tct aca gtt cgt aat gcc gat gtc att gct ggt ttt gat      1828
His Arg Leu Ser Thr Val Arg Asn Ala Asp Val Ile Ala Gly Phe Asp
    590                 595                 600 gat gga gtc att gtg gag aaa gga aat cat gat gaa ctc atg aaa gag      1876
Asp Gly Val Ile Val Glu Lys Gly Asn His Asp Glu Leu Met Lys Glu
605                 610                 615                 620 aag ggc att tac ttc aaa ctt gtc aca atg cag aca aga gga aat gaa      1924
Lys Gly Ile Tyr Phe Lys Leu Val Thr Met Gln Thr Arg Gly Asn Glu
                625                 630                 635 att gag tta gaa aat gcc act ggt gaa tcc aaa agt gaa agt gat gcc      1972
Ile Glu Leu Glu Asn Ala Thr Gly Glu Ser Lys Ser Glu Ser Asp Ala
            640                 645                 650 ttg gaa atg tct cca aaa gat tca ggg tcc agt tta ata aaa aga aga      2020
```

```
                Leu Glu Met Ser Pro Lys Asp Ser Gly Ser Ser Leu Ile Lys Arg Arg
                            655                 660                 665 tca act cgc agg agt ata cat gca cca caa ggc caa gac aga aag ctt            2068
Ser Thr Arg Arg Ser Ile His Ala Pro Gln Gly Gln Asp Arg Lys Leu
            670                 675                 680 ggt aca aaa gag gac ttg aat gag aat gta cct cca gtt tcc ttc tgg            2116
Gly Thr Lys Glu Asp Leu Asn Glu Asn Val Pro Pro Val Ser Phe Trp
685                 690                 695                 700 agg att ctg aag ctg aac tca act gaa tgg cct tat ttt gtg gtt ggt            2164
Arg Ile Leu Lys Leu Asn Ser Thr Glu Trp Pro Tyr Phe Val Val Gly
                705                 710                 715 ata ttt tgt gct att ata aac gga ggc ctg caa cca gca ttt tca ata            2212
Ile Phe Cys Ala Ile Ile Asn Gly Gly Leu Gln Pro Ala Phe Ser Ile
            720                 725                 730 ata ttt tca agg att ata ggg atc ttt acc cga gat gag gat cct gaa            2260
Ile Phe Ser Arg Ile Ile Gly Ile Phe Thr Arg Asp Glu Asp Pro Glu
            735                 740                 745 aca aaa cga cag aat agt aac atg ttt tct gta ttg ttt cta gtc ctt            2308
Thr Lys Arg Gln Asn Ser Asn Met Phe Ser Val Leu Phe Leu Val Leu
            750                 755                 760 gga att att tct ttt att aca ttt ttc ctc cag ggc ttc aca ttt ggc            2356
Gly Ile Ile Ser Phe Ile Thr Phe Phe Leu Gln Gly Phe Thr Phe Gly
765                 770                 775                 780 aaa gct ggg gag atc ctc act aag cgg ctt cga tac atg gtt ttc aga            2404
Lys Ala Gly Glu Ile Leu Thr Lys Arg Leu Arg Tyr Met Val Phe Arg
                785                 790                 795 tcc atg ctg aga cag gat gtc agc tgg ttt gat gac cct aaa aac acc            2452
Ser Met Leu Arg Gln Asp Val Ser Trp Phe Asp Asp Pro Lys Asn Thr
            800                 805                 810 act gga gca ttg aca acc agg ctt gcc aat gat gcg gct caa gtt aaa            2500
Thr Gly Ala Leu Thr Thr Arg Leu Ala Asn Asp Ala Ala Gln Val Lys
            815                 820                 825 ggg gct ata ggt tcc agg ctt gct gtc att acc cag aat ata gca aat            2548
Gly Ala Ile Gly Ser Arg Leu Ala Val Ile Thr Gln Asn Ile Ala Asn
            830                 835                 840 ctt ggg aca ggc att att ata tcc tta atc tat ggt tgg caa tta aca            2596
Leu Gly Thr Gly Ile Ile Ile Ser Leu Ile Tyr Gly Trp Gln Leu Thr
845                 850                 855                 860 ctt tta ctc tta gca att gta ccc atc att gca ata gca gga gtt gtt            2644
Leu Leu Leu Leu Ala Ile Val Pro Ile Ile Ala Ile Ala Gly Val Val
                865                 870                 875 gaa atg aaa atg ttg tct gga caa gca ctg aaa gat aag aaa gag cta            2692
Glu Met Lys Met Leu Ser Gly Gln Ala Leu Lys Asp Lys Lys Glu Leu
            880                 885                 890 gaa gga gct ggg aag att gct aca gaa gcc atc gaa aac ttc cga act            2740
Glu Gly Ala Gly Lys Ile Ala Thr Glu Ala Ile Glu Asn Phe Arg Thr
            895                 900                 905 gtt gtt tct ttg act cgg gag cag aag ttt gaa tac atg tat gca cag            2788
Val Val Ser Leu Thr Arg Glu Gln Lys Phe Glu Tyr Met Tyr Ala Gln
            910                 915                 920 agt ttg caa gta cca tac aga aac tct ttg agg aaa gca cac atc ttc            2836
Ser Leu Gln Val Pro Tyr Arg Asn Ser Leu Arg Lys Ala His Ile Phe
925                 930                 935                 940 ggg gtc tca ttt tct atc acc cag gca atg atg tat ttt tcc tat gct            2884
Gly Val Ser Phe Ser Ile Thr Gln Ala Met Met Tyr Phe Ser Tyr Ala
                945                 950                 955 ggc tgt ttc cgg ttt ggt gcc tac ttg gtg gca aat gag ttc atg aac            2932
Gly Cys Phe Arg Phe Gly Ala Tyr Leu Val Ala Asn Glu Phe Met Asn
            960                 965                 970
```

```
                                                    -continued ttt cag gat gtt ctt ttg gta ttc tca gct att gtc ttt ggt gcc atg    2980
Phe Gln Asp Val Leu Leu Val Phe Ser Ala Ile Val Phe Gly Ala Met
        975                 980                 985 gca gtg ggg cag gtc agt tca ttt gct cct gac tat gcc aaa gcc aaa    3028
Ala Val Gly Gln Val Ser Ser Phe Ala Pro Asp Tyr Ala Lys Ala Lys
990                 995                 1000 gta tca gca gcc cac gtc atc atg atc att gaa aaa agc cct ctg att    3076
Val Ser Ala Ala His Val Ile Met Ile Ile Glu Lys Ser Pro Leu Ile
1005                1010                1015                1020 gac agc tac agc cct cac ggc ctc aag cca aat acg ttg gaa gga aat    3124
Asp Ser Tyr Ser Pro His Gly Leu Lys Pro Asn Thr Leu Glu Gly Asn
            1025                1030                1035 gtg aca ttt aat gag gtc gtg ttc aac tat ccc act cga cca gac atc    3172
Val Thr Phe Asn Glu Val Val Phe Asn Tyr Pro Thr Arg Pro Asp Ile
        1040                1045                1050 ccc gtg ctc cag ggg ctg agc ctc gag gtg aag aag ggc cag acg ctg    3220
Pro Val Leu Gln Gly Leu Ser Leu Glu Val Lys Lys Gly Gln Thr Leu
    1055                1060                1065 gcc ctc gta ggt agc agt ggc tgt ggg aag agc aca gtt gtt cag ctc    3268
Ala Leu Val Gly Ser Ser Gly Cys Gly Lys Ser Thr Val Val Gln Leu
1070                1075                1080 cta gag cgc ttc tat gac ccc ttg gct ggt tca gtg cta att gat ggc    3316
Leu Glu Arg Phe Tyr Asp Pro Leu Ala Gly Ser Val Leu Ile Asp Gly
1085                1090                1095                1100 aaa gag ata aag cac ctg aat gtc cag tgg ctc cga gca cac ctg ggc    3364
Lys Glu Ile Lys His Leu Asn Val Gln Trp Leu Arg Ala His Leu Gly
            1105                1110                1115 atc gtg tct cag gag ccc atc ctg ttt gac tgc agc att gcc gag aac    3412
Ile Val Ser Gln Glu Pro Ile Leu Phe Asp Cys Ser Ile Ala Glu Asn
        1120                1125                1130 att gcc tat gga gac aac agc cgg gtc gta tca cat gaa gag att atg    3460
Ile Ala Tyr Gly Asp Asn Ser Arg Val Val Ser His Glu Glu Ile Met
    1135                1140                1145 cag gca gcc aag gag gcc aac ata cac cac ttc atc gag aca ctc cct    3508
Gln Ala Ala Lys Glu Ala Asn Ile His His Phe Ile Glu Thr Leu Pro
1150                1155                1160 gag aaa tac aac acc aga gta gga gac aaa gga acc cag ctc tct ggt    3556
Glu Lys Tyr Asn Thr Arg Val Gly Asp Lys Gly Thr Gln Leu Ser Gly
1165                1170                1175                1180 ggc cag aaa cag cgc att gcc ata gct cgc gct ctt gtt aga cag cct    3604
Gly Gln Lys Gln Arg Ile Ala Ile Ala Arg Ala Leu Val Arg Gln Pro
            1185                1190                1195 cat att ttg ctt ttg gat gaa gct aca tca gct ctg gat aca gaa agt    3652
His Ile Leu Leu Leu Asp Glu Ala Thr Ser Ala Leu Asp Thr Glu Ser
        1200                1205                1210 gaa aag gtt gtc caa gaa gcc ctg gac aaa gcc aga gaa ggc cgc acc    3700
Glu Lys Val Val Gln Glu Ala Leu Asp Lys Ala Arg Glu Gly Arg Thr
    1215                1220                1225 tgc att gtg atc gcc cac cgc ttg tcc acc atc cag aat gca gat tta    3748
Cys Ile Val Ile Ala His Arg Leu Ser Thr Ile Gln Asn Ala Asp Leu
1230                1235                1240 ata gtg gtg ttt cag aat ggc aaa gtc aag gag cat ggc aca cat caa    3796
Ile Val Val Phe Gln Asn Gly Lys Val Lys Glu His Gly Thr His Gln
1245                1250                1255                1260 cag ctg ctg gcc cag aaa ggc atc tat ttt tcc atg gtc agt gtc cag    3844
Gln Leu Leu Ala Gln Lys Gly Ile Tyr Phe Ser Met Val Ser Val Gln
            1265                1270                1275 gct gga gca aag cgc tagtgaactg tggccatatg agctgttaaa tatttttaa    3899
Ala Gly Ala Lys Arg
        1280
```

-continued

```
tatttgtgtt aaaacatggc atttaatcaa agttaaaagg tgagcactta ctggaaaaac    3959
tatgtagaac tacctgttta acatttcttg ctgcaactga agatcattcc accaagttca    4019
gagtcttcag attttataat taaaggaacc aaaagaaaca ttatctgatg gaataaaata    4079
ctggtgttaa ttgcattata aaattataga gtaattcaaa gtagattttg ttaataaatt    4139
gtataatttt tgtttatatt ttatttgtaa cttactgctt tgctgaaaga ttatagaagt    4199
ggtaaaaagt actgaatgtt tgaataaagt gctagctata ataaaactaa acttttatat    4259
caaaaaaaaa aaaaaaaaaa                                                4279

<210> SEQ ID NO 25
<211> LENGTH: 1281
<212> TYPE: PRT
<213> ORGANISM: Canis familiaris

<400> SEQUENCE: 25

Met Asp Pro Glu Gly Gly Arg Lys Gly Ser Ala Glu Lys Asn Phe Trp
 1               5                  10                  15

Lys Met Gly Lys Lys Ser Lys Lys Lys Glu Lys Lys Glu Lys Lys Pro
            20                  25                  30

Thr Val Ser Thr Phe Ala Met Phe Arg Tyr Ser Asn Trp Leu Asp Arg
        35                  40                  45

Leu Tyr Met Leu Val Gly Thr Met Ala Ala Ile Ile His Gly Ala Ala
    50                  55                  60

Leu Pro Leu Met Met Leu Val Phe Gly Asn Met Thr Asp Ser Phe Ala
65                  70                  75                  80

Asn Ala Gly Ile Ser Arg Asn Lys Thr Phe Pro Val Ile Ile Asn Glu
                85                  90                  95

Ser Ile Thr Asn Asn Thr Gln His Phe Ile Asn His Leu Glu Glu Glu
            100                 105                 110

Met Thr Thr Tyr Ala Tyr Tyr Ser Gly Ile Gly Ala Gly Val Leu
        115                 120                 125

Val Ala Ala Tyr Ile Gln Val Ser Phe Trp Cys Leu Ala Ala Gly Arg
    130                 135                 140

Gln Ile Leu Lys Ile Arg Lys Gln Phe His Ala Ile Met Arg Gln
145                 150                 155                 160

Glu Ile Gly Trp Phe Asp Val His Asp Val Gly Glu Leu Asn Thr Arg
                165                 170                 175

Leu Thr Asp Asp Val Ser Lys Ile Asn Glu Gly Ile Gly Asp Lys Ile
            180                 185                 190

Gly Met Phe Phe Gln Ser Ile Ala Thr Phe Phe Thr Gly Phe Ile Val
        195                 200                 205

Gly Phe Thr Arg Gly Trp Lys Leu Thr Leu Val Ile Leu Ala Ile Ser
    210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
            260                 265                 270

Lys Lys Glu Leu Glu Arg Tyr Asn Lys Asn Leu Glu Glu Ala Lys Gly
        275                 280                 285

Ile Gly Ile Lys Lys Ala Ile Thr Ala Asn Ile Ser Ile Gly Ala Ala
    290                 295                 300
```

```
Phe Leu Leu Ile Tyr Ala Ser Tyr Ala Leu Ala Phe Trp Tyr Gly Thr
305                 310                 315                 320

Ser Leu Val Leu Ser Ser Glu Tyr Ser Ile Gly Gln Val Leu Thr Val
            325                 330                 335

Phe Phe Ser Val Leu Ile Gly Ala Phe Ser Ile Gly Gln Ala Ser Pro
            340                 345                 350

Ser Ile Glu Ala Phe Ala Asn Ala Arg Gly Ala Ala Tyr Glu Ile Phe
        355                 360                 365

Lys Ile Ile Asp Asn Lys Pro Ser Ile Asp Ser Tyr Ser Lys Ser Gly
    370                 375                 380

His Lys Pro Asp Asn Ile Lys Gly Asn Leu Glu Phe Lys Asn Val His
385                 390                 395                 400

Phe Ser Tyr Pro Ser Arg Lys Glu Val Lys Ile Leu Lys Gly Leu Asn
                405                 410                 415

Leu Lys Val Gln Ser Gly Gln Thr Val Ala Leu Val Gly Asn Ser Gly
            420                 425                 430

Cys Gly Lys Ser Thr Thr Val Gln Leu Met Gln Arg Leu Tyr Asp Pro
        435                 440                 445

Thr Asp Gly Met Val Cys Ile Asp Gly Gln Asp Ile Arg Thr Ile Asn
    450                 455                 460

Val Arg His Leu Arg Glu Ile Thr Gly Val Val Ser Gln Glu Pro Val
465                 470                 475                 480

Leu Phe Ala Thr Thr Ile Ala Glu Asn Ile Arg Tyr Gly Arg Glu Asn
                485                 490                 495

Val Thr Met Asp Glu Ile Glu Lys Ala Val Lys Glu Ala Asn Ala Tyr
            500                 505                 510

Asp Phe Ile Met Lys Leu Pro Asn Lys Phe Asp Thr Leu Val Gly Glu
        515                 520                 525

Arg Gly Ala Gln Leu Ser Gly Gly Gln Lys Gln Arg Ile Ala Ile Ala
    530                 535                 540

Arg Ala Leu Val Arg Asn Pro Lys Ile Leu Leu Leu Asp Glu Ala Thr
545                 550                 555                 560

Ser Ala Leu Asp Thr Glu Ser Glu Ala Val Val Gln Val Ala Leu Asp
                565                 570                 575

Lys Ala Arg Lys Gly Arg Thr Thr Ile Val Ile Ala His Arg Leu Ser
            580                 585                 590

Thr Val Arg Asn Ala Asp Val Ile Ala Gly Phe Asp Asp Gly Val Ile
        595                 600                 605

Val Glu Lys Gly Asn His Asp Glu Leu Met Lys Glu Lys Gly Ile Tyr
    610                 615                 620

Phe Lys Leu Val Thr Met Gln Thr Arg Gly Asn Glu Ile Glu Leu Glu
625                 630                 635                 640

Asn Ala Thr Gly Glu Ser Lys Ser Glu Ser Asp Ala Leu Glu Met Ser
                645                 650                 655

Pro Lys Asp Ser Gly Ser Ser Leu Ile Lys Arg Arg Ser Thr Arg Arg
            660                 665                 670

Ser Ile His Ala Pro Gln Gly Gln Asp Arg Lys Leu Gly Thr Lys Glu
        675                 680                 685

Asp Leu Asn Glu Asn Val Pro Pro Val Ser Phe Trp Arg Ile Leu Lys
    690                 695                 700

Leu Asn Ser Thr Glu Trp Pro Tyr Phe Val Val Gly Ile Phe Cys Ala
705                 710                 715                 720
```

-continued

```
Ile Ile Asn Gly Gly Leu Gln Pro Ala Phe Ser Ile Ile Phe Ser Arg
            725                 730                 735

Ile Ile Gly Ile Phe Thr Arg Asp Glu Asp Pro Glu Thr Lys Arg Gln
            740                 745                 750

Asn Ser Asn Met Phe Ser Val Leu Phe Leu Val Leu Gly Ile Ile Ser
            755                 760                 765

Phe Ile Thr Phe Phe Leu Gln Gly Phe Thr Phe Gly Lys Ala Gly Glu
            770                 775                 780

Ile Leu Thr Lys Arg Leu Arg Tyr Met Val Phe Arg Ser Met Leu Arg
785                 790                 795                 800

Gln Asp Val Ser Trp Phe Asp Pro Lys Asn Thr Thr Gly Ala Leu
                    805                 810                 815

Thr Thr Arg Leu Ala Asn Asp Ala Ala Gln Val Lys Gly Ala Ile Gly
                    820                 825                 830

Ser Arg Leu Ala Val Ile Thr Gln Asn Ile Ala Asn Leu Gly Thr Gly
                    835                 840                 845

Ile Ile Ile Ser Leu Ile Tyr Gly Trp Gln Leu Thr Leu Leu Leu Leu
            850                 855                 860

Ala Ile Val Pro Ile Ile Ala Ile Ala Gly Val Val Glu Met Lys Met
865                 870                 875                 880

Leu Ser Gly Gln Ala Leu Lys Asp Lys Lys Glu Leu Glu Gly Ala Gly
                    885                 890                 895

Lys Ile Ala Thr Glu Ala Ile Glu Asn Phe Arg Thr Val Val Ser Leu
                    900                 905                 910

Thr Arg Glu Gln Lys Phe Glu Tyr Met Tyr Ala Gln Ser Leu Gln Val
            915                 920                 925

Pro Tyr Arg Asn Ser Leu Arg Lys Ala His Ile Phe Gly Val Ser Phe
            930                 935                 940

Ser Ile Thr Gln Ala Met Met Tyr Phe Ser Tyr Ala Gly Cys Phe Arg
945                 950                 955                 960

Phe Gly Ala Tyr Leu Val Ala Asn Glu Phe Met Asn Phe Gln Asp Val
                    965                 970                 975

Leu Leu Val Phe Ser Ala Ile Val Phe Gly Ala Met Ala Val Gly Gln
                    980                 985                 990

Val Ser Ser Phe Ala Pro Asp Tyr Ala Lys Ala Lys Val Ser Ala Ala
            995                 1000                1005

His Val Ile Met Ile Ile Glu Lys Ser Pro Leu Ile Asp Ser Tyr Ser
    1010                1015                1020

Pro His Gly Leu Lys Pro Asn Thr Leu Glu Gly Asn Val Thr Phe Asn
1025                1030                1035                1040

Glu Val Val Phe Asn Tyr Pro Thr Arg Pro Asp Ile Pro Val Leu Gln
                    1045                1050                1055

Gly Leu Ser Leu Glu Val Lys Lys Gly Gln Thr Leu Ala Leu Val Gly
                    1060                1065                1070

Ser Ser Gly Cys Gly Lys Ser Thr Val Val Gln Leu Leu Glu Arg Phe
            1075                1080                1085

Tyr Asp Pro Leu Ala Gly Ser Val Leu Ile Asp Gly Lys Glu Ile Lys
            1090                1095                1100

His Leu Asn Val Gln Trp Leu Arg Ala His Leu Gly Ile Val Ser Gln
1105                1110                1115                1120

Glu Pro Ile Leu Phe Asp Cys Ser Ile Ala Glu Asn Ile Ala Tyr Gly
            1125                1130                1135

Asp Asn Ser Arg Val Val Ser His Glu Glu Ile Met Gln Ala Ala Lys
```

```
                 1140                1145               1150
Glu Ala Asn Ile His His Phe Ile Glu Thr Leu Pro Glu Lys Tyr Asn
            1155                1160                1165

Thr Arg Val Gly Asp Lys Gly Thr Gln Leu Ser Gly Gly Gln Lys Gln
    1170                1175                1180

Arg Ile Ala Ile Ala Arg Ala Leu Val Arg Gln Pro His Ile Leu Leu
1185                1190                1195                1200

Leu Asp Glu Ala Thr Ser Ala Leu Asp Thr Glu Ser Glu Lys Val Val
                1205                1210                1215

Gln Glu Ala Leu Asp Lys Ala Arg Glu Gly Arg Thr Cys Ile Val Ile
            1220                1225                1230

Ala His Arg Leu Ser Thr Ile Gln Asn Ala Asp Leu Ile Val Val Phe
            1235                1240                1245

Gln Asn Gly Lys Val Lys Glu His Gly Thr His Gln Gln Leu Leu Ala
        1250                1255                1260

Gln Lys Gly Ile Tyr Phe Ser Met Val Ser Val Gln Ala Gly Ala Lys
1265                1270                1275                1280

Arg

<210> SEQ ID NO 26
<211> LENGTH: 4279
<212> TYPE: DNA
<213> ORGANISM: Canis familiaris
<220> FEATURE:
<221> NAME/KEY: CDS
<222> LOCATION: (17)...(3859)

<400> SEQUENCE: 26
ggagcgcgag gtcggg atg gat cct gaa gga ggc cgt aag ggg agt gca gag         52
              Met Asp Pro Glu Gly Gly Arg Lys Gly Ser Ala Glu
                1               5                   10 aag aac ttc tgg aaa atg ggc aaa aaa agt aaa aaa aaa gag aag aaa          100
Lys Asn Phe Trp Lys Met Gly Lys Lys Ser Lys Lys Lys Glu Lys Lys
            15                  20                  25 gaa aag aaa cca act gtc agc acg ttt gca atg ttt cgc tat tca aat          148
Glu Lys Lys Pro Thr Val Ser Thr Phe Ala Met Phe Arg Tyr Ser Asn
        30                  35                  40 tgg ctt gat agg ttg tat atg ttg gtg ggg aca atg gct gcc atc atc          196
Trp Leu Asp Arg Leu Tyr Met Leu Val Gly Thr Met Ala Ala Ile Ile
45                  50                  55                  60 cat gga gct gca ctc cct ctc atg atg ctg gtt ttt gga aac atg aca          244
His Gly Ala Ala Leu Pro Leu Met Met Leu Val Phe Gly Asn Met Thr
                65                  70                  75 gat agc ttt gca aat gca gga att tca aga aac aaa act ttt cca gtt          292
Asp Ser Phe Ala Asn Ala Gly Ile Ser Arg Asn Lys Thr Phe Pro Val
            80                  85                  90 ata att aat gaa agt att acg aac aat aca caa cat ttc atc aac cat          340
Ile Ile Asn Glu Ser Ile Thr Asn Asn Thr Gln His Phe Ile Asn His
        95                  100                 105 ctg gag gag gaa atg acc acg tat gcc tat tat tac agt ggg atc ggt          388
Leu Glu Glu Glu Met Thr Thr Tyr Ala Tyr Tyr Tyr Ser Gly Ile Gly
    110                 115                 120 gct ggc gtg ctg gtg gct gct tac atc cag gtt tca ttc tgg tgc ctg          436
Ala Gly Val Leu Val Ala Ala Tyr Ile Gln Val Ser Phe Trp Cys Leu
125                 130                 135                 140 gca gca gga aga cag ata ctc aaa att aga aaa caa ttt ttt cat gct          484
Ala Ala Gly Arg Gln Ile Leu Lys Ile Arg Lys Gln Phe Phe His Ala
                145                 150                 155
```

-continued

| | | |
|---|---|---|
| atc atg cga cag gag att ggc tgg ttt gac gtg cat gac gtt ggg gag<br>Ile Met Arg Gln Glu Ile Gly Trp Phe Asp Val His Asp Val Gly Glu<br>160                            165                         170 | 532 | |
| ctt aac acc cgg ctc aca gac gat gtc tcc aaa atc aat gaa gga att<br>Leu Asn Thr Arg Leu Thr Asp Asp Val Ser Lys Ile Asn Glu Gly Ile<br>     175                         180                          185 | 580 | |
| ggc gac aaa att gga atg ttc ttt caa tca ata gca aca ttt ttc acc<br>Gly Asp Lys Ile Gly Met Phe Phe Gln Ser Ile Ala Thr Phe Phe Thr<br>190                            195                        200 | 628 | |
| ggt ttt ata gtg ggg ttt aca cgt ggt tgg aag cta acc ctt gtg att<br>Gly Phe Ile Val Gly Phe Thr Arg Gly Trp Lys Leu Thr Leu Val Ile<br>205                        210                        215                        220 | 676 | |
| ttg gcc atc agc cct gtt ctt gga ctt tca gcc gcc atc tgg gca aag<br>Leu Ala Ile Ser Pro Val Leu Gly Leu Ser Ala Ala Ile Trp Ala Lys<br>                     225                        230                        235 | 724 | |
| ata cta tct tca ttt act gat aaa gaa ctc ttg gcc tat gca aaa gct<br>Ile Leu Ser Ser Phe Thr Asp Lys Glu Leu Leu Ala Tyr Ala Lys Ala<br>                     240                        245                        250 | 772 | |
| gga gca gta gct gaa gaa gtc tta gca gca atc aga act gtg att gcc<br>Gly Ala Val Ala Glu Glu Val Leu Ala Ala Ile Arg Thr Val Ile Ala<br>                     255                        260                        265 | 820 | |
| ttt gga gga caa aag aaa gaa ctt gaa agg tac aac aaa aat tta gaa<br>Phe Gly Gly Gln Lys Lys Glu Leu Glu Arg Tyr Asn Lys Asn Leu Glu<br>270                            275                        280 | 868 | |
| gaa gct aaa gga att ggg ata aag aaa gct atc acg gcc aac att tct<br>Glu Ala Lys Gly Ile Gly Ile Lys Lys Ala Ile Thr Ala Asn Ile Ser<br>285                            290                        295                        300 | 916 | |
| att ggt gcc gct ttc tta ttg atc tat gca tca tat gct ctg gct ttc<br>Ile Gly Ala Ala Phe Leu Leu Ile Tyr Ala Ser Tyr Ala Leu Ala Phe<br>                     305                        310                        315 | 964 | |
| tgg tat ggg acc tcc ttg gtc ctc tcc agt gaa tat act att gga caa<br>Trp Tyr Gly Thr Ser Leu Val Leu Ser Ser Glu Tyr Thr Ile Gly Gln<br>                     320                        325                        330 | 1012 | |
| gta ctc act gtc ttc ttt tct gta tta att ggg gct ttt agt att gga<br>Val Leu Thr Val Phe Phe Ser Val Leu Ile Gly Ala Phe Ser Ile Gly<br>                     335                        340                        345 | 1060 | |
| cag gca tcc cca agc att gaa gca ttt gca aac gca aga gga gca gct<br>Gln Ala Ser Pro Ser Ile Glu Ala Phe Ala Asn Ala Arg Gly Ala Ala<br>350                            355                        360 | 1108 | |
| tat gaa atc ttc aag ata att gac aat aaa cca agc att gac agc tat<br>Tyr Glu Ile Phe Lys Ile Ile Asp Asn Lys Pro Ser Ile Asp Ser Tyr<br>365                            370                        375                        380 | 1156 | |
| tcg aag agt gga cat aaa cca gat aat att aag gga aat ttg gaa ttc<br>Ser Lys Ser Gly His Lys Pro Asp Asn Ile Lys Gly Asn Leu Glu Phe<br>                     385                        390                        395 | 1204 | |
| aaa aat gtt cac ttc agt tac cct tct cga aaa gaa gtt aag atc tta<br>Lys Asn Val His Phe Ser Tyr Pro Ser Arg Lys Glu Val Lys Ile Leu<br>                     400                        405                        410 | 1252 | |
| aag ggt ctc aac ctg aag gtt cag agt ggg cag aca gtg gcg ctg gtt<br>Lys Gly Leu Asn Leu Lys Val Gln Ser Gly Gln Thr Val Ala Leu Val<br>                     415                        420                        425 | 1300 | |
| ggg aac agt ggc tgc ggg aag agc acg acc gtg cag ctg atg cag agg<br>Gly Asn Ser Gly Cys Gly Lys Ser Thr Thr Val Gln Leu Met Gln Arg<br>430                            435                        440 | 1348 | |
| ctc tat gac ccc aca gat ggc atg gtc tgt att gat gga cag gac att<br>Leu Tyr Asp Pro Thr Asp Gly Met Val Cys Ile Asp Gly Gln Asp Ile<br>445                            450                        455                        460 | 1396 | |
| agg acc ata aat gta agg cat ctt cgg gaa att act ggt gtg gtg agt<br>Arg Thr Ile Asn Val Arg His Leu Arg Glu Ile Thr Gly Val Val Ser<br>                     465                        470                        475 | 1444 | |

-continued

```
cag gag cct gtg ttg ttt gcc acc acg ata gct gaa aac att cgc tat      1492
Gln Glu Pro Val Leu Phe Ala Thr Thr Ile Ala Glu Asn Ile Arg Tyr
            480                 485                 490 ggc cgc gaa aat gtc acc atg gat gag att gag aaa gct gtt aag gaa      1540
Gly Arg Glu Asn Val Thr Met Asp Glu Ile Glu Lys Ala Val Lys Glu
        495                 500                 505 gcc aat gcc tat gat ttt atc atg aaa cta cct aat aaa ttt gac act      1588
Ala Asn Ala Tyr Asp Phe Ile Met Lys Leu Pro Asn Lys Phe Asp Thr
    510                 515                 520 ctg gtt gga gag aga ggg gcc cag ctg agt ggt gga cag aaa cag aga      1636
Leu Val Gly Glu Arg Gly Ala Gln Leu Ser Gly Gly Gln Lys Gln Arg
525                 530                 535                 540 atc gcc att gct cgg gcc ctg gtt cgc aac ccc aag att ctt ctg ctg      1684
Ile Ala Ile Ala Arg Ala Leu Val Arg Asn Pro Lys Ile Leu Leu Leu
                545                 550                 555 gat gag gca acg tca gct ctg gac act gaa agt gaa gca gtg gtt cag      1732
Asp Glu Ala Thr Ser Ala Leu Asp Thr Glu Ser Glu Ala Val Val Gln
            560                 565                 570 gtg gcc ctg gat aag gcc aga aaa ggc cgg act acc att gtg ata gct      1780
Val Ala Leu Asp Lys Ala Arg Lys Gly Arg Thr Thr Ile Val Ile Ala
        575                 580                 585 cat cgt ttg tct aca gtt cgt aat gcc gat gtc att gct ggt ttt gat      1828
His Arg Leu Ser Thr Val Arg Asn Ala Asp Val Ile Ala Gly Phe Asp
    590                 595                 600 gat gga gtc att gtg gag aaa gga aat cat gat gaa ctc atg aaa gag      1876
Asp Gly Val Ile Val Glu Lys Gly Asn His Asp Glu Leu Met Lys Glu
605                 610                 615                 620 aag ggc att tac ttc aaa ctt gtc aca atg cag aca aga gga aat gaa      1924
Lys Gly Ile Tyr Phe Lys Leu Val Thr Met Gln Thr Arg Gly Asn Glu
                625                 630                 635 att gag tta gaa aat gcc act ggt gaa tcc aaa agt gaa agt gat gcc      1972
Ile Glu Leu Glu Asn Ala Thr Gly Glu Ser Lys Ser Glu Ser Asp Ala
            640                 645                 650 ttg gaa atg tct cca aaa gat tca ggg tcc agt tta ata aaa aga aga      2020
Leu Glu Met Ser Pro Lys Asp Ser Gly Ser Ser Leu Ile Lys Arg Arg
        655                 660                 665 tca act cgc agg agt ata cat gca cca caa ggc caa gac aga aag ctt      2068
Ser Thr Arg Arg Ser Ile His Ala Pro Gln Gly Gln Asp Arg Lys Leu
    670                 675                 680 ggt aca aaa gag gac ttg aat gag aat gta cct cca gtt tcc ttc tgg      2116
Gly Thr Lys Glu Asp Leu Asn Glu Asn Val Pro Pro Val Ser Phe Trp
685                 690                 695                 700 agg att ctg aag ctg aac tca act gaa tgg cct tat ttt gtg gtt ggt      2164
Arg Ile Leu Lys Leu Asn Ser Thr Glu Trp Pro Tyr Phe Val Val Gly
                705                 710                 715 ata ttt tgt gct att ata aac gga ggc ctg caa cca gca ttt tca ata      2212
Ile Phe Cys Ala Ile Ile Asn Gly Gly Leu Gln Pro Ala Phe Ser Ile
            720                 725                 730 ata ttt tca agg att ata ggg atc ttt acc cga gat gag gat cct gaa      2260
Ile Phe Ser Arg Ile Ile Gly Ile Phe Thr Arg Asp Glu Asp Pro Glu
        735                 740                 745 aca aaa cga cag aat agt aac atg ttt tct gta ttg ttt cta gtc ctt      2308
Thr Lys Arg Gln Asn Ser Asn Met Phe Ser Val Leu Phe Leu Val Leu
    750                 755                 760 gga att att tct ttt att aca ttt ttc ctc cag ggc ttc aca ttt ggc      2356
Gly Ile Ile Ser Phe Ile Thr Phe Phe Leu Gln Gly Phe Thr Phe Gly
765                 770                 775                 780 aaa gct ggg gag atc ctc act aag cgg ctt cga tac atg gtt ttc aga      2404
Lys Ala Gly Glu Ile Leu Thr Lys Arg Leu Arg Tyr Met Val Phe Arg
```

-continued

```
                785                 790                 795
tcc atg ctg aga cag gat gtc agc tgg ttt gat gac cct aaa aac acc      2452
Ser Met Leu Arg Gln Asp Val Ser Trp Phe Asp Asp Pro Lys Asn Thr
            800                 805                 810 act gga gca ttg aca acc agg ctt gcc aat gat gcg gct caa gtt aaa      2500
Thr Gly Ala Leu Thr Thr Arg Leu Ala Asn Asp Ala Ala Gln Val Lys
        815                 820                 825 ggg gct ata ggt tcc agg ctt gct gtc att acc cag aat ata gca aat      2548
Gly Ala Ile Gly Ser Arg Leu Ala Val Ile Thr Gln Asn Ile Ala Asn
    830                 835                 840 ctt ggg aca ggc att att ata tcc tta atc tat ggt tgg caa tta aca      2596
Leu Gly Thr Gly Ile Ile Ile Ser Leu Ile Tyr Gly Trp Gln Leu Thr
845                 850                 855                 860 ctt tta ctc tta gca att gta ccc atc att gca ata gca gga gtt gtt      2644
Leu Leu Leu Leu Ala Ile Val Pro Ile Ile Ala Ile Ala Gly Val Val
                865                 870                 875 gaa atg aaa atg ttg tct gga caa gca ctg aaa gat aag aaa gag cta      2692
Glu Met Lys Met Leu Ser Gly Gln Ala Leu Lys Asp Lys Lys Glu Leu
            880                 885                 890 gaa gga gct ggg aag att gct aca gaa gcc atc gaa aac ttc cga act      2740
Glu Gly Ala Gly Lys Ile Ala Thr Glu Ala Ile Glu Asn Phe Arg Thr
        895                 900                 905 gtt gtt tct ttg act cgg gag cag aag ttt gaa tac atg tat gca cag      2788
Val Val Ser Leu Thr Arg Glu Gln Lys Phe Glu Tyr Met Tyr Ala Gln
    910                 915                 920 agt ttg caa gta cca tac aga aac tct ttg agg aaa gca cac atc ttc      2836
Ser Leu Gln Val Pro Tyr Arg Asn Ser Leu Arg Lys Ala His Ile Phe
925                 930                 935                 940 ggg gtc tca ttt tct atc acc cag gca atg atg tat ttt tcc tat gct      2884
Gly Val Ser Phe Ser Ile Thr Gln Ala Met Met Tyr Phe Ser Tyr Ala
                945                 950                 955 ggc tgt ttc cgg ttt ggt gcc tac ttg gtg gca aat gag ttc atg aac      2932
Gly Cys Phe Arg Phe Gly Ala Tyr Leu Val Ala Asn Glu Phe Met Asn
            960                 965                 970 ttt cag gat gtt ctt ttg gta ttc tca gct att gtc ttt ggt gcc atg      2980
Phe Gln Asp Val Leu Leu Val Phe Ser Ala Ile Val Phe Gly Ala Met
        975                 980                 985 gca gtg ggg cag gtc agt tca ttt gct cct gac tat gcc aaa gcc aaa      3028
Ala Val Gly Gln Val Ser Ser Phe Ala Pro Asp Tyr Ala Lys Ala Lys
    990                 995                 1000 gta tca gca gcc cac gtc atc atg atc att gaa aaa agc cct ctg att      3076
Val Ser Ala Ala His Val Ile Met Ile Ile Glu Lys Ser Pro Leu Ile
1005                1010                1015                1020 gac agc tac agc cct cac ggc ctc aag cca aat acg ttg gaa gga aat      3124
Asp Ser Tyr Ser Pro His Gly Leu Lys Pro Asn Thr Leu Glu Gly Asn
                1025                1030                1035 gtg aca ttt aat gag gtc gtg ttc aac tat ccc act cga cca gac atc      3172
Val Thr Phe Asn Glu Val Val Phe Asn Tyr Pro Thr Arg Pro Asp Ile
            1040                1045                1050 ccc gtg ctc cag ggg ctg agc ctc gag gtg aag aag ggc cag acg ctg      3220
Pro Val Leu Gln Gly Leu Ser Leu Glu Val Lys Lys Gly Gln Thr Leu
        1055                1060                1065 gcc ctc gta ggt agc agt ggc tgt ggg aag agc aca gtt gtt cag ctc      3268
Ala Leu Val Gly Ser Ser Gly Cys Gly Lys Ser Thr Val Val Gln Leu
    1070                1075                1080 cta gag cgc ttc tat gac ccc ttg gct ggt tca gtg cta att gat ggc      3316
Leu Glu Arg Phe Tyr Asp Pro Leu Ala Gly Ser Val Leu Ile Asp Gly
1085                1090                1095                1100 aaa gag ata aag cac ctg aat gtc cag tgg ctc cga gca cac ctg ggc      3364
```

-continued

```
Lys Glu Ile Lys His Leu Asn Val Gln Trp Leu Arg Ala His Leu Gly
            1105                1110                1115 atc gtg tct cag gag ccc atc ctg ttt gac tgc agc att gcc gag aac      3412
Ile Val Ser Gln Glu Pro Ile Leu Phe Asp Cys Ser Ile Ala Glu Asn
        1120                1125                1130 att gcc tat gga gac aac agc cgg gtc gta tca cat gaa gag att gtg      3460
Ile Ala Tyr Gly Asp Asn Ser Arg Val Val Ser His Glu Glu Ile Val
    1135                1140                1145 cag gca gcc aag gag gcc aac ata cac cac ttc atc gag aca ctc cct      3508
Gln Ala Ala Lys Glu Ala Asn Ile His His Phe Ile Glu Thr Leu Pro
1150                1155                1160 gag aaa tac aac acc aga gta gga gac aaa gga acc cag ctc tct ggt      3556
Glu Lys Tyr Asn Thr Arg Val Gly Asp Lys Gly Thr Gln Leu Ser Gly
1165                1170                1175                1180 ggc cag aaa cag cgc att gcc ata gct cgc gct ctt gtt aga cag cct      3604
Gly Gln Lys Gln Arg Ile Ala Ile Ala Arg Ala Leu Val Arg Gln Pro
            1185                1190                1195 cat att ttg ctt ttg gat gaa gct aca tca gct ctg gat aca gaa agt      3652
His Ile Leu Leu Leu Asp Glu Ala Thr Ser Ala Leu Asp Thr Glu Ser
        1200                1205                1210 gaa aag gtt gtc caa gaa gcc ctg gac aaa gcc aga gaa ggc cgc acc      3700
Glu Lys Val Val Gln Glu Ala Leu Asp Lys Ala Arg Glu Gly Arg Thr
    1215                1220                1225 tgc att gtg atc gcc cac cgc ttg tcc acc atc cag aat gca gat tta      3748
Cys Ile Val Ile Ala His Arg Leu Ser Thr Ile Gln Asn Ala Asp Leu
1230                1235                1240 ata gtg gtg ttt cag aat ggc aaa gtc aag gag cat ggc aca cat caa      3796
Ile Val Val Phe Gln Asn Gly Lys Val Lys Glu His Gly Thr His Gln
1245                1250                1255                1260 cag ctg ctg gcc cag aaa ggc atc tat ttt tcc atg gtc agt gtc cag      3844
Gln Leu Leu Ala Gln Lys Gly Ile Tyr Phe Ser Met Val Ser Val Gln
            1265                1270                1275 gct gga gca aag cgc tagtgaactg tggccatatg agctgttaaa tattttttaa      3899
Ala Gly Ala Lys Arg
            1280 tatttgtgtt aaaacatggc atttaatcaa agttaaaagg tgagcactta ctggaaaaac      3959 tatgtagaac tacctgttta acatttcttg ctgcaactga agatcattcc accaagttca      4019 gagtcttcag attttataat taaggaacc aaaagaaaca ttatctgatg gaataaaata      4079 ctggtgttaa ttgcattata aaattataga gtaattcaaa gtagattttg ttaataaatt      4139 gtataatttt tgtttatatt ttatttgtaa cttactgctt tgctgaaaga ttatagaagt      4199 ggtaaaaagt actgaatgtt tgaataaagt gctagctata ataaaactaa acttttatat      4259 caaaaaaaaa aaaaaaaaaa                                                  4279
```

<210> SEQ ID NO 27
<211> LENGTH: 1281
<212> TYPE: PRT
<213> ORGANISM: Canis familiaris

<400> SEQUENCE: 27

```
Met Asp Pro Glu Gly Gly Arg Lys Gly Ser Ala Glu Lys Asn Phe Trp
1               5                   10                  15

Lys Met Gly Lys Lys Ser Lys Lys Glu Lys Lys Glu Lys Lys Pro
            20                  25                  30

Thr Val Ser Thr Phe Ala Met Phe Arg Tyr Ser Asn Trp Leu Asp Arg
        35                  40                  45

Leu Tyr Met Leu Val Gly Thr Met Ala Ala Ile Ile His Gly Ala Ala
```

-continued

```
              50                  55                  60
Leu Pro Leu Met Met Leu Val Phe Gly Asn Met Thr Asp Ser Phe Ala
65                   70                  75                  80

Asn Ala Gly Ile Ser Arg Asn Lys Thr Phe Pro Val Ile Ile Asn Glu
                85                  90                  95

Ser Ile Thr Asn Asn Thr Gln His Phe Ile Asn His Leu Glu Glu Glu
            100                 105                 110

Met Thr Thr Tyr Ala Tyr Tyr Ser Gly Ile Gly Ala Gly Val Leu
            115                 120                 125

Val Ala Ala Tyr Ile Gln Val Ser Phe Trp Cys Leu Ala Ala Gly Arg
130                 135                 140

Gln Ile Leu Lys Ile Arg Lys Gln Phe His Ala Ile Met Arg Gln
145                 150                 155                 160

Glu Ile Gly Trp Phe Asp Val His Asp Val Gly Glu Leu Asn Thr Arg
                165                 170                 175

Leu Thr Asp Asp Val Ser Lys Ile Asn Glu Gly Ile Gly Asp Lys Ile
            180                 185                 190

Gly Met Phe Phe Gln Ser Ile Ala Thr Phe Phe Thr Gly Phe Ile Val
                195                 200                 205

Gly Phe Thr Arg Gly Trp Lys Leu Thr Leu Val Ile Leu Ala Ile Ser
210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
            260                 265                 270

Lys Lys Glu Leu Glu Arg Tyr Asn Lys Asn Leu Glu Glu Ala Lys Gly
            275                 280                 285

Ile Gly Ile Lys Lys Ala Ile Thr Ala Asn Ile Ser Ile Gly Ala Ala
            290                 295                 300

Phe Leu Leu Ile Tyr Ala Ser Tyr Ala Leu Ala Phe Trp Tyr Gly Thr
305                 310                 315                 320

Ser Leu Val Leu Ser Ser Glu Tyr Thr Ile Gly Gln Val Leu Thr Val
                325                 330                 335

Phe Phe Ser Val Leu Ile Gly Ala Phe Ser Ile Gly Gln Ala Ser Pro
            340                 345                 350

Ser Ile Glu Ala Phe Ala Asn Ala Arg Gly Ala Ala Tyr Glu Ile Phe
            355                 360                 365

Lys Ile Ile Asp Asn Lys Pro Ser Ile Asp Ser Tyr Ser Lys Ser Gly
            370                 375                 380

His Lys Pro Asp Asn Ile Lys Gly Asn Leu Glu Phe Lys Asn Val His
385                 390                 395                 400

Phe Ser Tyr Pro Ser Arg Lys Glu Val Lys Ile Leu Lys Gly Leu Asn
                405                 410                 415

Leu Lys Val Gln Ser Gly Gln Thr Val Ala Leu Val Gly Asn Ser Gly
            420                 425                 430

Cys Gly Lys Ser Thr Thr Val Gln Leu Met Gln Arg Leu Tyr Asp Pro
            435                 440                 445

Thr Asp Gly Met Val Cys Ile Asp Gly Gln Asp Ile Arg Thr Ile Asn
            450                 455                 460

Val Arg His Leu Arg Glu Ile Thr Gly Val Val Ser Gln Glu Pro Val
465                 470                 475                 480
```

-continued

```
Leu Phe Ala Thr Thr Ile Ala Glu Asn Ile Arg Tyr Gly Arg Glu Asn
            485                 490                 495
Val Thr Met Asp Glu Ile Glu Lys Ala Val Lys Glu Ala Asn Ala Tyr
        500                 505                 510
Asp Phe Ile Met Lys Leu Pro Asn Lys Phe Asp Thr Leu Val Gly Glu
        515                 520                 525
Arg Gly Ala Gln Leu Ser Gly Gln Lys Gln Arg Ile Ala Ile Ala
    530                 535                 540
Arg Ala Leu Val Arg Asn Pro Lys Ile Leu Leu Leu Asp Glu Ala Thr
545                 550                 555                 560
Ser Ala Leu Asp Thr Glu Ser Glu Ala Val Val Gln Val Ala Leu Asp
                565                 570                 575
Lys Ala Arg Lys Gly Arg Thr Thr Ile Val Ile Ala His Arg Leu Ser
                580                 585                 590
Thr Val Arg Asn Ala Asp Val Ile Ala Gly Phe Asp Asp Gly Val Ile
            595                 600                 605
Val Glu Lys Gly Asn His Asp Glu Leu Met Lys Glu Lys Gly Ile Tyr
    610                 615                 620
Phe Lys Leu Val Thr Met Gln Thr Arg Gly Asn Glu Ile Glu Leu Glu
625                 630                 635                 640
Asn Ala Thr Gly Glu Ser Lys Ser Glu Ser Asp Ala Leu Glu Met Ser
                645                 650                 655
Pro Lys Asp Ser Gly Ser Ser Leu Ile Lys Arg Arg Ser Thr Arg Arg
                660                 665                 670
Ser Ile His Ala Pro Gln Gly Gln Asp Arg Lys Leu Gly Thr Lys Glu
            675                 680                 685
Asp Leu Asn Glu Asn Val Pro Pro Val Ser Phe Trp Arg Ile Leu Lys
    690                 695                 700
Leu Asn Ser Thr Glu Trp Pro Tyr Phe Val Val Gly Ile Phe Cys Ala
705                 710                 715                 720
Ile Ile Asn Gly Gly Leu Gln Pro Ala Phe Ser Ile Ile Phe Ser Arg
                725                 730                 735
Ile Ile Gly Ile Phe Thr Arg Asp Glu Asp Pro Glu Thr Lys Arg Gln
                740                 745                 750
Asn Ser Asn Met Phe Ser Val Leu Phe Leu Val Leu Gly Ile Ile Ser
            755                 760                 765
Phe Ile Thr Phe Phe Leu Gln Gly Phe Thr Phe Gly Lys Ala Gly Glu
    770                 775                 780
Ile Leu Thr Lys Arg Leu Arg Tyr Met Val Phe Arg Ser Met Leu Arg
785                 790                 795                 800
Gln Asp Val Ser Trp Phe Asp Asp Pro Lys Asn Thr Thr Gly Ala Leu
                805                 810                 815
Thr Thr Arg Leu Ala Asn Asp Ala Ala Gln Val Lys Gly Ala Ile Gly
                820                 825                 830
Ser Arg Leu Ala Val Ile Thr Gln Asn Ile Ala Asn Leu Gly Thr Gly
            835                 840                 845
Ile Ile Ile Ser Leu Ile Tyr Gly Trp Gln Leu Thr Leu Leu Leu Leu
    850                 855                 860
Ala Ile Val Pro Ile Ile Ala Ile Ala Gly Val Val Glu Met Lys Met
865                 870                 875                 880
Leu Ser Gly Gln Ala Leu Lys Asp Lys Lys Glu Leu Glu Gly Ala Gly
                885                 890                 895
```

```
Lys Ile Ala Thr Glu Ala Ile Glu Asn Phe Arg Thr Val Val Ser Leu
                900                 905                 910

Thr Arg Glu Gln Lys Phe Glu Tyr Met Tyr Ala Gln Ser Leu Gln Val
            915                 920                 925

Pro Tyr Arg Asn Ser Leu Arg Lys Ala His Ile Phe Gly Val Ser Phe
        930                 935                 940

Ser Ile Thr Gln Ala Met Met Tyr Phe Ser Tyr Ala Gly Cys Phe Arg
945                 950                 955                 960

Phe Gly Ala Tyr Leu Val Ala Asn Glu Phe Met Asn Phe Gln Asp Val
                965                 970                 975

Leu Leu Val Phe Ser Ala Ile Val Phe Gly Ala Met Ala Val Gly Gln
            980                 985                 990

Val Ser Ser Phe Ala Pro Asp Tyr Ala Lys Ala Lys Val Ser Ala Ala
        995                 1000                1005

His Val Ile Met Ile Ile Glu Lys Ser Pro Leu Ile Asp Ser Tyr Ser
    1010                1015                1020

Pro His Gly Leu Lys Pro Asn Thr Leu Glu Gly Asn Val Thr Phe Asn
1025                1030                1035                1040

Glu Val Val Phe Asn Tyr Pro Thr Arg Pro Asp Ile Pro Val Leu Gln
                1045                1050                1055

Gly Leu Ser Leu Glu Val Lys Lys Gly Gln Thr Leu Ala Leu Val Gly
            1060                1065                1070

Ser Ser Gly Cys Gly Lys Ser Thr Val Val Gln Leu Leu Glu Arg Phe
        1075                1080                1085

Tyr Asp Pro Leu Ala Gly Ser Val Leu Ile Asp Gly Lys Glu Ile Lys
    1090                1095                1100

His Leu Asn Val Gln Trp Leu Arg Ala His Leu Gly Ile Val Ser Gln
1105                1110                1115                1120

Glu Pro Ile Leu Phe Asp Cys Ser Ile Ala Glu Asn Ile Ala Tyr Gly
                1125                1130                1135

Asp Asn Ser Arg Val Val Ser His Glu Glu Ile Val Gln Ala Ala Lys
            1140                1145                1150

Glu Ala Asn Ile His His Phe Ile Glu Thr Leu Pro Glu Lys Tyr Asn
        1155                1160                1165

Thr Arg Val Gly Asp Lys Gly Thr Gln Leu Ser Gly Gly Gln Lys Gln
    1170                1175                1180

Arg Ile Ala Ile Ala Arg Ala Leu Val Arg Gln Pro His Ile Leu Leu
1185                1190                1195                1200

Leu Asp Glu Ala Thr Ser Ala Leu Asp Thr Glu Ser Glu Lys Val Val
                1205                1210                1215

Gln Glu Ala Leu Asp Lys Ala Arg Glu Gly Arg Thr Cys Ile Val Ile
            1220                1225                1230

Ala His Arg Leu Ser Thr Ile Gln Asn Ala Asp Leu Ile Val Val Phe
        1235                1240                1245

Gln Asn Gly Lys Val Lys Glu His Gly Thr His Gln Gln Leu Leu Ala
    1250                1255                1260

Gln Lys Gly Ile Tyr Phe Ser Met Val Ser Val Gln Ala Gly Ala Lys
1265                1270                1275                1280

Arg

<210> SEQ ID NO 28
<211> LENGTH: 52
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: Unsure
<222> LOCATION: (1)..(2)
<223> OTHER INFORMATION: n = a, c, g, or t/u

<400> SEQUENCE: 28 nnttttttt tttttttttt tttttttttt ttcgccggcg acttaagatc tt         52

<210> SEQ ID NO 29
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 29
ccatcctaat acgactcact gtagggc                                    27

<210> SEQ ID NO 30
<211> LENGTH: 34
<212> TYPE: DNA
<213> ORGANISM: Canis familiaris

<400> SEQUENCE: 30
gcaaatgctt caatgcttgg ggatgcctgt ccaa                            34

<210> SEQ ID NO 31
<211> LENGTH: 33
<212> TYPE: DNA
<213> ORGANISM: Canis familiaris

<400> SEQUENCE: 31
gagctgggtt cctttgtctc ctactctggt gtt                             33

<210> SEQ ID NO 32
<211> LENGTH: 23
<212> TYPE: DNA
<213> ORGANISM: Canis familiaris

<400> SEQUENCE: 32
gcaaatgctg gttgcaggcc tcc                                        23
```